（12）United States Patent
Narayan et al.

(10) Patent No.: US 12,336,804 B2
(45) Date of Patent: *Jun. 24, 2025

(54) SYSTEM AND METHOD FOR DIAGNOSING AND TREATING BIOLOGICAL RHYTHM DISORDERS

(71) Applicant: PhysCade, Inc., Palo Alto, CA (US)

(72) Inventors: Sanjiv M. Narayan, Palo Alto, CA (US); Miguel Rodrigo Bort, Valencia (ES); Mahmood I. Alhusseini, Menlo Park, CA (US)

(73) Assignee: PhysCade, Inc., Palo Alto, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 18/088,523

(22) Filed: Dec. 24, 2022

(65) Prior Publication Data

US 2023/0200676 A1 Jun. 29, 2023

Related U.S. Application Data

(63) Continuation of application No. 17/708,991, filed on Mar. 30, 2022, now Pat. No. 11,564,591.
(Continued)

(51) Int. Cl.
*A61B 5/277* (2021.01)
*A61B 5/00* (2006.01)
(Continued)

(52) U.S. Cl.
CPC .............. *A61B 5/068* (2013.01); *A61B 5/277* (2021.01); *A61B 5/287* (2021.01); *A61B 5/7267* (2013.01); *A61B 5/742* (2013.01); *G16H 50/70* (2018.01)

(58) Field of Classification Search
CPC ......... A61B 5/068; A61B 5/277; A61B 5/287; A61B 5/367; A61B 5/6858; A61B 5/6885;
(Continued)

(56) References Cited

U.S. PATENT DOCUMENTS 5,476,495 A 12/1995 Kordis et al.
6,231,570 B1 5/2001 Tu et al.
(Continued)

FOREIGN PATENT DOCUMENTS

EP 3777743 A1 2/2021
EP 3791816 A2 3/2021
(Continued)

OTHER PUBLICATIONS

Invitation to Pay Additional Fees, Patent Cooperation Treaty Application No. PCT/US2022/022609, Jun. 3, 2022, 3 pages.
(Continued)

*Primary Examiner* — George Manuel
(74) *Attorney, Agent, or Firm* — Fenwick & West LLP

(57) ABSTRACT

A heart treatment system is disclosed capable of diagnosing one or more critical regions of interest for a biological rhythm disorder by sensing signals from biological tissue. If a critical region is not present at the current location of sensed signals, the system is capable of indicating a guidance direction in which to navigate to reach one or more critical regions. Ablation energy is delivered to treat said region of interest. Signals are again sensed and analyzed to assess the impact of treatment. This process is repeated until all critical regions of interest are treated. In some embodiments, all functionality is provided by a single sensing and treating catheter with display device and analytical software.

21 Claims, 19 Drawing Sheets

Related U.S. Application Data

(60) Provisional application No. 63/283,901, filed on Nov. 29, 2021.

(51) Int. Cl.
   *A61B 5/06* (2006.01)
   *A61B 5/287* (2021.01)
   *G16H 50/70* (2018.01)

(58) Field of Classification Search
   CPC ...... A61B 5/7267; A61B 5/742; G16H 20/30; G16H 30/40; G16H 40/63; G16H 50/20; G16H 50/30; G16H 50/70
   See application file for complete search history.

(56) References Cited

U.S. PATENT DOCUMENTS

| | | |
|---|---|---|
| 7,300,438 B2 | 11/2007 | Falwell et al. |
| 7,850,685 B2 | 12/2010 | Kunis et al. |
| 8,715,199 B1 | 5/2014 | Macneil et al. |
| 8,880,158 B2 | 11/2014 | Spector |
| 9,033,892 B2 | 5/2015 | Su et al. |
| 9,050,006 B2 | 6/2015 | Narayan et al. |
| 9,078,583 B2 | 7/2015 | Nguyen et al. |
| 9,101,333 B2 | 8/2015 | Schwartz |
| 9,186,081 B2 | 11/2015 | Afonso et al. |
| 9,271,680 B2 | 3/2016 | Dubois et al. |
| 9,282,910 B2 | 3/2016 | Narayan et al. |
| 9,332,915 B2 | 5/2016 | Narayan et al. |
| 9,370,329 B2 | 6/2016 | Tun et al. |
| 9,427,169 B2 | 8/2016 | Zeng et al. |
| 9,474,491 B2 | 10/2016 | Li et al. |
| 9,554,847 B2 | 1/2017 | Govari et al. |
| 9,687,166 B2 | 6/2017 | Subramaniam et al. |
| 10,016,233 B2 | 7/2018 | Pike |
| 10,070,795 B2 | 9/2018 | Macneil et al. |
| 10,105,179 B2 | 10/2018 | Harlev et al. |
| 10,136,829 B2 | 11/2018 | Deno et al. |
| 10,143,374 B2 | 12/2018 | Ruppersberg |
| 10,194,994 B2 | 2/2019 | Deno et al. |
| 10,524,684 B2 | 1/2020 | Fay et al. |
| 10,568,686 B2 | 2/2020 | Lee |
| 10,617,467 B2 | 4/2020 | Viswanathan et al. |
| 10,864,031 B2 | 12/2020 | Mazor et al. |
| 10,912,472 B2 | 2/2021 | Finlay et al. |
| 10,980,602 B2 | 4/2021 | Deno et al. |
| 11,051,867 B2 | 7/2021 | Babkin et al. |
| 2002/0095151 A1 | 7/2002 | Dahla et al. |
| 2002/0107511 A1 | 8/2002 | Collins et al. |
| 2003/0204185 A1 | 10/2003 | Sherman et al. |
| 2008/0281310 A1 | 11/2008 | Dunning et al. |
| 2009/0318749 A1 | 12/2009 | Stolen et al. |
| 2010/0291521 A1 | 11/2010 | Simon |
| 2011/0257563 A1 | 10/2011 | Thapliyal et al. |
| 2013/0282084 A1 | 10/2013 | Mathur et al. |
| 2013/0296679 A1 | 11/2013 | Condie et al. |
| 2014/0114204 A1 | 4/2014 | Narayan et al. |
| 2014/0128859 A1 | 5/2014 | Lee |
| 2014/0276712 A1 | 9/2014 | Mallin et al. |
| 2015/0254419 A1 | 9/2015 | Laughner et al. |
| 2015/0282729 A1 | 10/2015 | Harlev et al. |
| 2016/0067448 A1* | 3/2016 | Blacker .................. A61B 34/25 604/95.01 |
| 2017/0156791 A1 | 6/2017 | Govari |
| 2017/0202515 A1 | 7/2017 | Zrihem et al. |
| 2017/0202521 A1 | 7/2017 | Urman et al. |
| 2017/0232263 A1 | 8/2017 | Narayan et al. |
| 2017/0332971 A1 | 11/2017 | Macneil et al. |
| 2019/0076179 A1 | 3/2019 | Babkin et al. |
| 2020/0085311 A1 | 3/2020 | Tzvieli et al. |
| 2020/0138319 A1 | 5/2020 | Spector |
| 2020/0229866 A1 | 7/2020 | Harlev et al. |
| 2020/0345261 A1 | 11/2020 | Haeusser et al. |
| 2020/0352652 A1 | 11/2020 | Amit et al. |
| 2021/0085204 A1 | 3/2021 | Auerbach et al. |
| 2021/0106249 A1 | 4/2021 | Schmidt et al. |
| 2021/0259765 A1 | 8/2021 | Narayan |
| 2021/0315627 A1 | 10/2021 | Babkin et al. |
| 2022/0015682 A1 | 1/2022 | Spector et al. |
| 2022/0051091 A1 | 2/2022 | Ravuna et al. |
| 2022/0338923 A1 | 10/2022 | Bort et al. |
| 2023/0277112 A1 | 9/2023 | Weiss et al. |
| 2023/0363643 A1 | 11/2023 | Tran |

FOREIGN PATENT DOCUMENTS

| | | |
|---|---|---|
| WO | WO 2013/013098 A1 | 1/2013 |
| WO | WO 2013/106557 A1 | 7/2013 |
| WO | WO 2017/165830 A1 | 9/2017 |
| WO | WO 2017/165846 A1 | 9/2017 |
| WO | WO 2017/192617 A1 | 11/2017 |
| WO | WO 2024/003509 A1 | 1/2024 |

OTHER PUBLICATIONS

Alhusseini, M., et al., "Two Independent Mapping Techniques Identify Rotational Activity Patterns at Sites of Local Termination During Persistent Atrial Fibrillation," Journal of Cardiovascular Electrophysiology, vol. 28, Issue 6, Jun. 2017, pp. 615-622.

Anfinsen, O. G., et al., "Bipolar radiofrequency catheter ablation creates confluent lesions at larger interelectrode spacing than does unipolar ablation from two electrodes in the porcine heart," European Heart Journal, vol. 19, Issue 7, Jul. 1, 1998, pp. 1075-1084.

Atteberry, J., "How 2-D Bar Codes Work," HowStuffWorks.com, Mar. 3, 2011, [Online][Retrieved Feb. 21, 2023], Retrieved from the internet <URL:https://science.howstuffworks.com/innovation/repurposed-inventions/2d-barcodes.htm>.

Baykaner, T., et al., "Clinical Implications of Ablation of Drivers for Atrial Fibrillation," Circulation: Arrhythmia and Electrophysiology, vol. 11, Issue 5, May 2018, e006119. 10 pages.

Binkowski, B. J., et al., "How to avoid unnecessary RF applications in cavo-tricuspid isthmus: common atrial flutter ablation using 8-mm-tip mini-electrode-equipped catheter," *Journal of Interventional Cardiac Electrophysiology*, vol. 60, Issue 1, pp. 109-114.

Buist, T. J., et al., "Efficacy of multi-electrode linear irreversible electroporation," EP Europace, vol. 23, Issue 3, Mar. 2021, pp. 464-468.

Clarnette et al., "Outcomes of persistent and long-standing persistent atrial fibrillation ablation: a systematic review and meta-analysis," EP Europace, vol. 20, Issue FI_3, Nov. 2018, pp. f366-f376.

Dekker, L. R., "Last call on nMARQ safety," EP Europace, vol. 18, Issue 8, Aug. 2016, pp. 1119-1120.

Glashan, C. A., et al., "Multisize Electrodes for Substrate Identification in Ischemic Cardiomyopathy: Validation by Integration of Whole Heart Histology," JACC: Clinical Electrophysiology, vol. 5, Issue 10, Oct. 2019, pp. 1130-1140.

Haines, DE, et al., "Microembolism and Catheter Ablation I: A Comparison of Irrigated Radiofrequency and Multielectrode-phased Radiofrequency Catheter Ablation of Pulmonary Vein Ostia," Circulation: Arrhythmia and Electrophysiology, Feb. 2013, vol. 6, Issue 1, pp. 16-22.

Hummel, J., et al., "Evaluation of stroke incidence with duty-cycled multielectrode-phased radiofrequency ablation of persistent atrial fibrillation results of the Victory AF Study," *Journal of Cardiovascular Electrophysiology*, vol. 31, Issue 6, Jun. 2020, pp. 1289-1297.

International Search Report and Written Opinion, Patent Cooperation Treaty Application No. PCT/US2022/029630, Oct. 26, 2022, 31 pages.

International Search Report and Written Opinion, Patent Cooperation Treaty Application No. PCT/US2022/039873, Jan. 30, 2023, 21 pages.

Iwasawa, J., et al., "Temperature-Controlled Radiofrequency Ablation for Pulmonary Vein Isolation in Patients with Atrial Fibrillation," Journal of the American College of Cardiology, vol. 70, Issue 5, Aug. 2017, pp. 542-553.

(56) References Cited

OTHER PUBLICATIONS

Kardos, A., et al., "Cavotricuspid isthmus ablation with large-tip gold alloy versus platinum-iridium-tip electrode catheters," *Pacing and Clinical Electrophysiology*, vol. 32, Suppl 1, Mar. 2009, pp. S138-S140.

Koruth, J. S., et al., "Feasibility, safety, and durability of porcine atrial ablation using a lattice-tip temperature-controlled radiofrequency ablation catheter," *Journal of Cardiovascular Electrophysiology*, vol. 31, Issue 6, Jun. 2020, pp. 1323-1331.

Kowalewski, "Interaction of Localized Drivers and Disorganized Activation in Persistent Atrial Fibrillation," Circulation: Arrhythmia and Electrophysiology, vol. 11, Issue 6, Jun. 2018, e005846, pp. 1-12.

Lee, J.M., et al., "The Electrical Isolation of the Left Atrial Posterior Wall in Catheter Ablation of Persistent Atrial Fibrillation," JACC: Clinical Electrophysiology, vol. 5, Issue 11, Nov. 2019, pp. 1253-1261.

Lewalter, T., et al., "Gold vs. platinum-iridium tip catheter for cavotricuspid isthmus ablation: the AURUM 8 study," EP Europace, vol. 13, Issue 1, Jan. 2011, pp. 102-108.

Lewalter, T., et al., "Gold-Tip Electrodes—A New "Deep Lesion" Technology for Catheter Ablation? In Vitro Comparison of a Gold Alloy Versus Platinum-Iridium Tip Electrode Ablation Catheter," *Journal of Cardiovascular Electrophysiology*, vol. 16, Issue 7, Jul. 2005, pp. 770-772.

Lin et al., "Comparison of phase mapping and electrogram-based driver mapping for catheter ablation in atrial fibrillation," Pacing and Clinical Electrophysiology, Author manuscript; available in PMC May 30, 2019, published in final edited form as: Pacing and Clinical Electrophysiology, vol. 42, Issue 2, Feb. 2019, pp. 216-223.

Linhart, M., et al., "Superiority of Gold versus Platinum Irrigated Tip Catheter Ablation of the Pulmonary Veins and the Cavotricuspid Isthmus: A Randomized Study Comparing Tip Temperatures and Cooling Flow Requirements," *Journal of Cardiovascular Electrophysiology*, vol. 23, Issue 7, Jul. 2012, pp. 717-721.

Mahida, S., et al., "nMARQ Ablation for Atrial Fibrillation: Results from a Multicenter Study," Journal of Cardiovascular Electrophysiology, vol. 26, Issue 7, Jul. 2015, pp. 724-729.

Michaud, G. F., "Asymptomatic Cerebral Emboli with the PVAC Gold: Worth Another Look?" JACC: Clinical Electrophysiology, vol. 5, Issue 3, Mar. 2019, pp. 327-329.

Michaud, G. F., et al., "Rapid Point-by-Point Pulmonary Vein Isolation," JACC: Clinical Electrophysiology, vol. 5, Issue 7, Jul. 2019, pp. 787-788.

Nazer, B., "Feasibility of Rapid Linear-Endocardial and Epicardial Ventricular Ablation Using an Irrigated Multipolar Radiofrequency Ablation Catheter," Circulation: Arrhythmia and Electrophysiology, Mar. 2017, vol. 10, Issue 3, e004760, pp. 1-9.

Parameswaran et al., "Clinical impact of rotor ablation in atrial fibrillation: a systematic review," EP Europace, vol. 20, Issue 7, Jul. 2018, pp. 1099-1106.

Petersen, H. H., et al., "Tissue temperatures and lesion size during irrigated tip catheter radiofrequency ablation: an in vitro comparison of temperature-controlled irrigated tip ablation, power-controlled irrigated tip ablation, and standard temperature-controlled ablation." *Pacing and Clinical Electrophysiology*, vol. 23, Issue 1, Jan. 2000, pp. 8-17.

Ramirez et al., "Efficacy and safety of driver-guided catheter ablation for atrial fibrillation: A systematic review and meta-analysis," *Journal of Cardiovascular Electrophysiology*, vol. 28, Issue 12, Dec. 2017, pp. 1371-1378.

Reddy, V. Y., et al., "Pulmonary Vein Isolation with Very High Power, Short Duration, Temperature-Controlled Lesions: The QDOT-FAST Trial," Journal of Cardiovascular Electrophysiology, vol. 5, Issue 7, Jul. 2019, pp. 778-786.

Scharf, C., et al., "Ablation of Persistent Atrial Fibrillation Using Multielectrode Catheters and Duty-Cycled Radiofrequency Energy," Journal of the American College of Cardiology, vol. 54, Issue 15, Oct. 2009, pp. 1450-1456.

Swerdlow, M., et al., "Comparing phase and electrographic flow mapping for persistent atrial fibrillation," Pacing and Clinical Electrophysiology, Author manuscript; available in PMC May 1, 2020, published in final edited form as: Pacing and Clinical Electrophysiology, vol. 42, Issue 5, May 2019, pp. 499-507.

United States Final Office Action, U.S. Appl. No. 17/884,220, filed Mar. 15, 2024, 18 pages.

United States Final Office Action, U.S. Appl. No. 17/884,220, filed May 12, 2023, 17 pages.

United States Non-Final Office Action, U.S. Appl. No. 17/884,220, filed Jan. 10, 2023, 24 pages.

United States Non-Final Office Action, U.S. Appl. No. 17/884,220, filed Oct. 19, 2022, 23 pages.

United States Non-Final Office Action, U.S. Appl. No. 17/884,220, filed Sep. 25, 2023, 17 pages.

United States Non-Final Office Action, U.S. Appl. No. 18/418,043, filed Apr. 16, 2024, 31 pages.

Wijffels, M., et al., "Characterization of In Vitro and In Vivo Lesions Made by a Novel Multichannel Ablation Generator and a Circumlinear Decapolar Ablation Catheter," Journal of Cardiovascular Electrophysiology, vol. 20, Issue 10, Oct. 2009, pp. 1142-1148.

Woodford, C., "Barcodes and barcode scanners," ExplainthatStuff. com, 12 pages, last updated: Jun. 14, 2022, [Online][Retrieved Feb. 21, 2023], Retrieved from the internet <URL:https://www.explainthatstuff.com/barcodescanners.html>.

Zaman, JAB, et al., "Identification and characterization of sites where persistent atrial fibrillation is terminated by localized ablation," Circulation: Arrhythmia and Electrophysiology, Jan. 2018, vol. 11, Issue 1, e005258, pp. 1-12.

United States Office Action, U.S. Appl. No. 18/418,043, filed Aug. 22, 2024, 29 pages.

\* cited by examiner

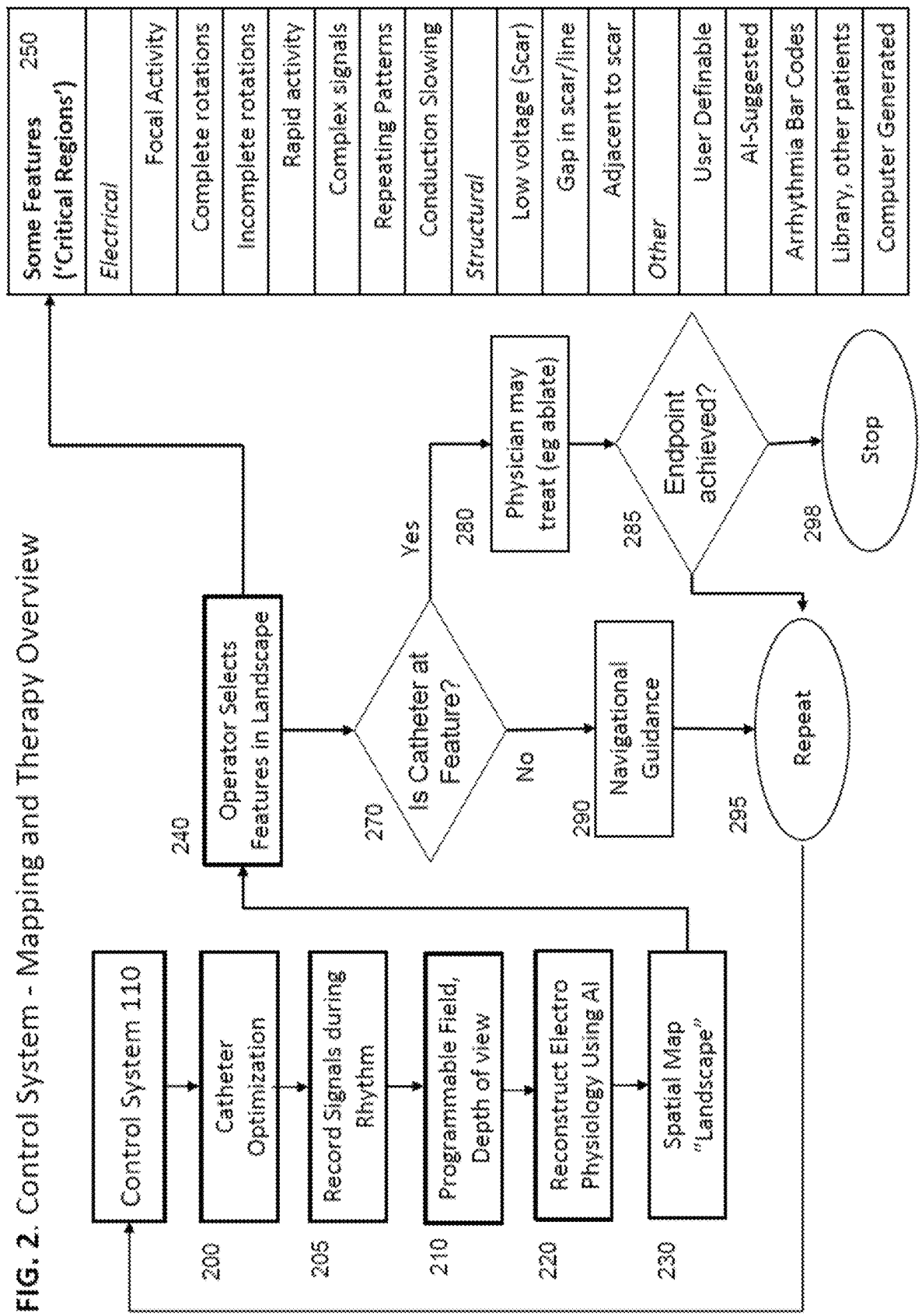
FIG. 2. Control System – Mapping and Therapy Overview

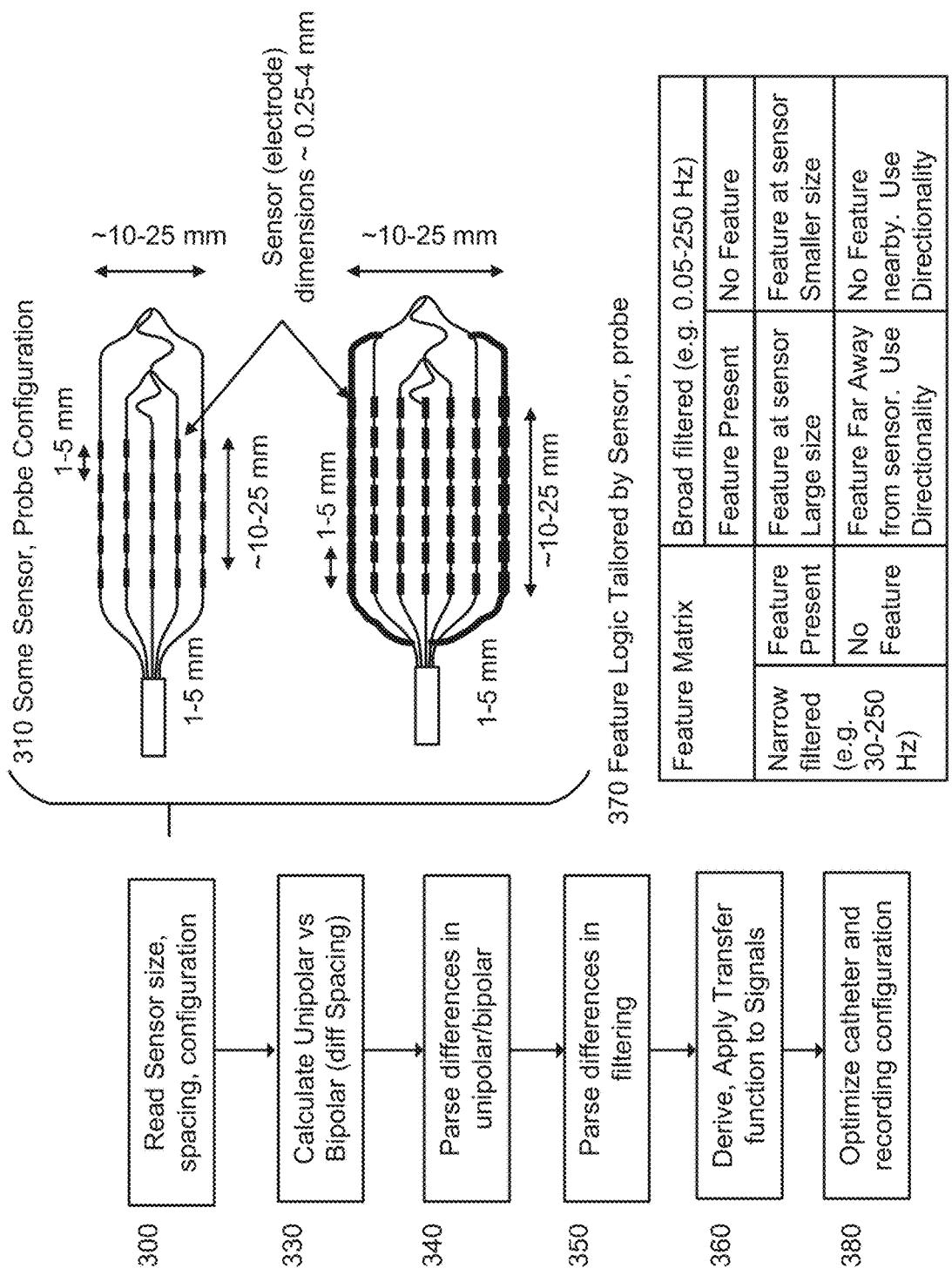
FIG. 3. Control System – Optimizing Catheter, Programmable Field and Depth of View

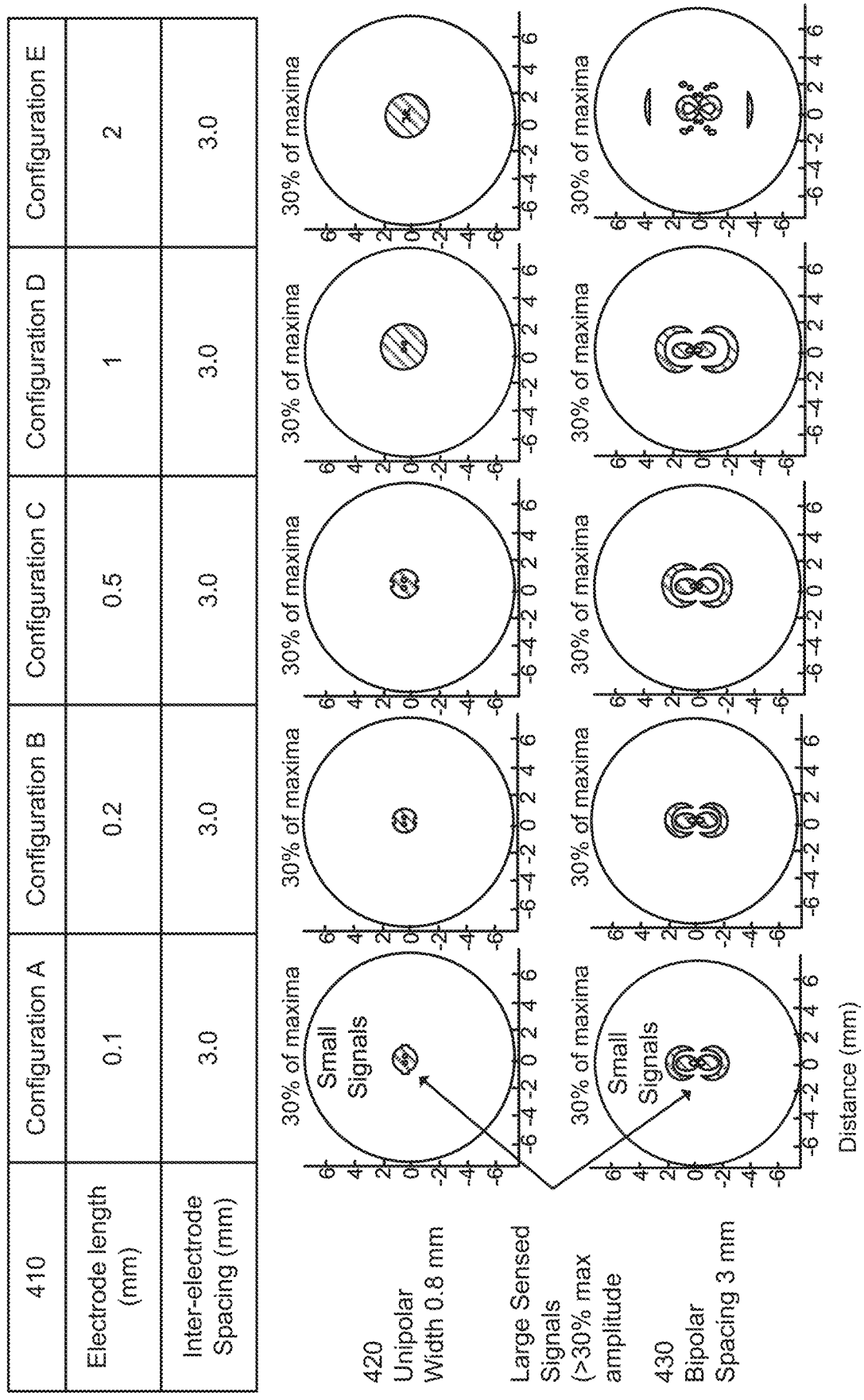

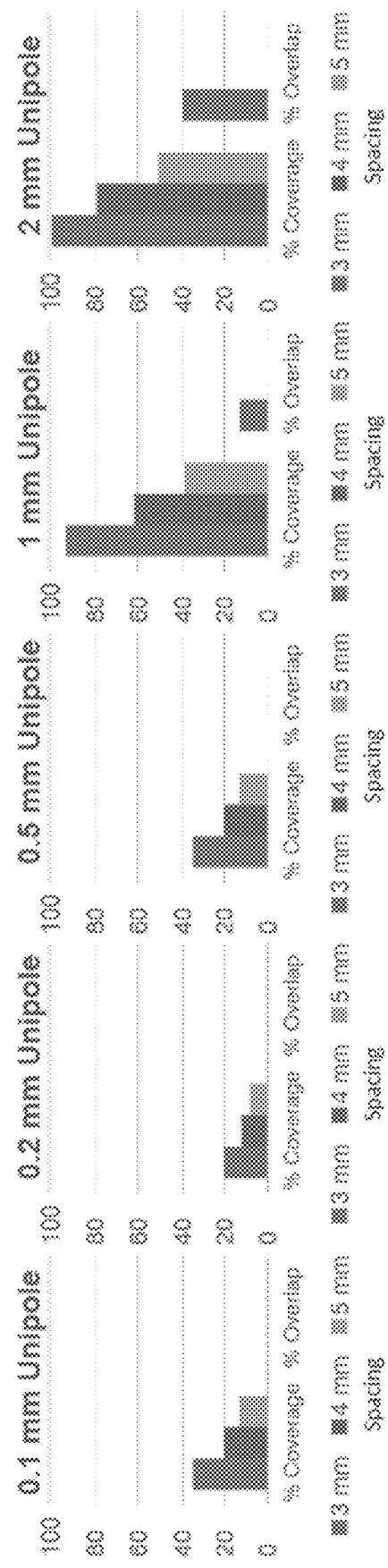
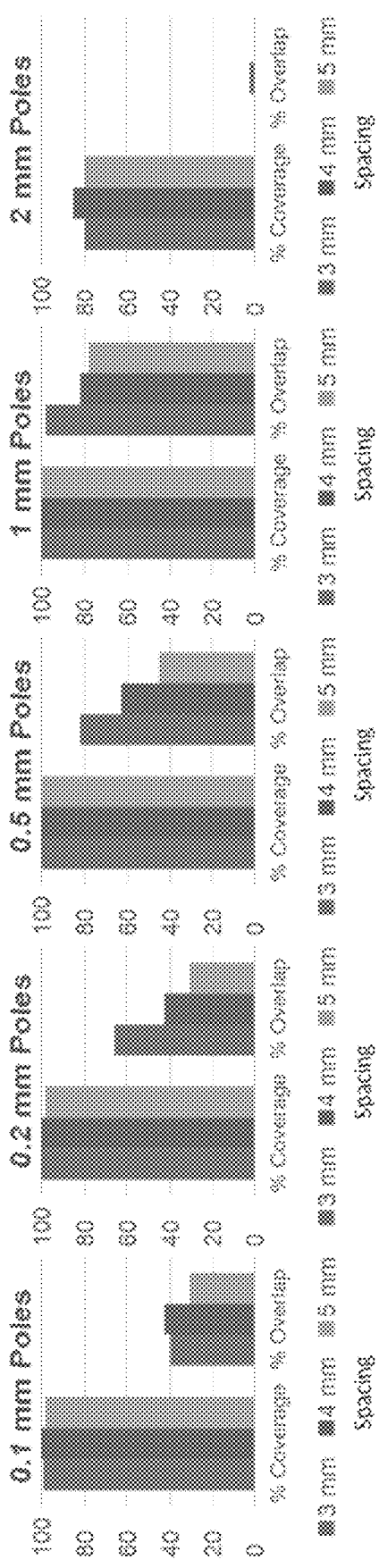
FIG. 4B. Impact of Varying Electrode Configuration on Field of View

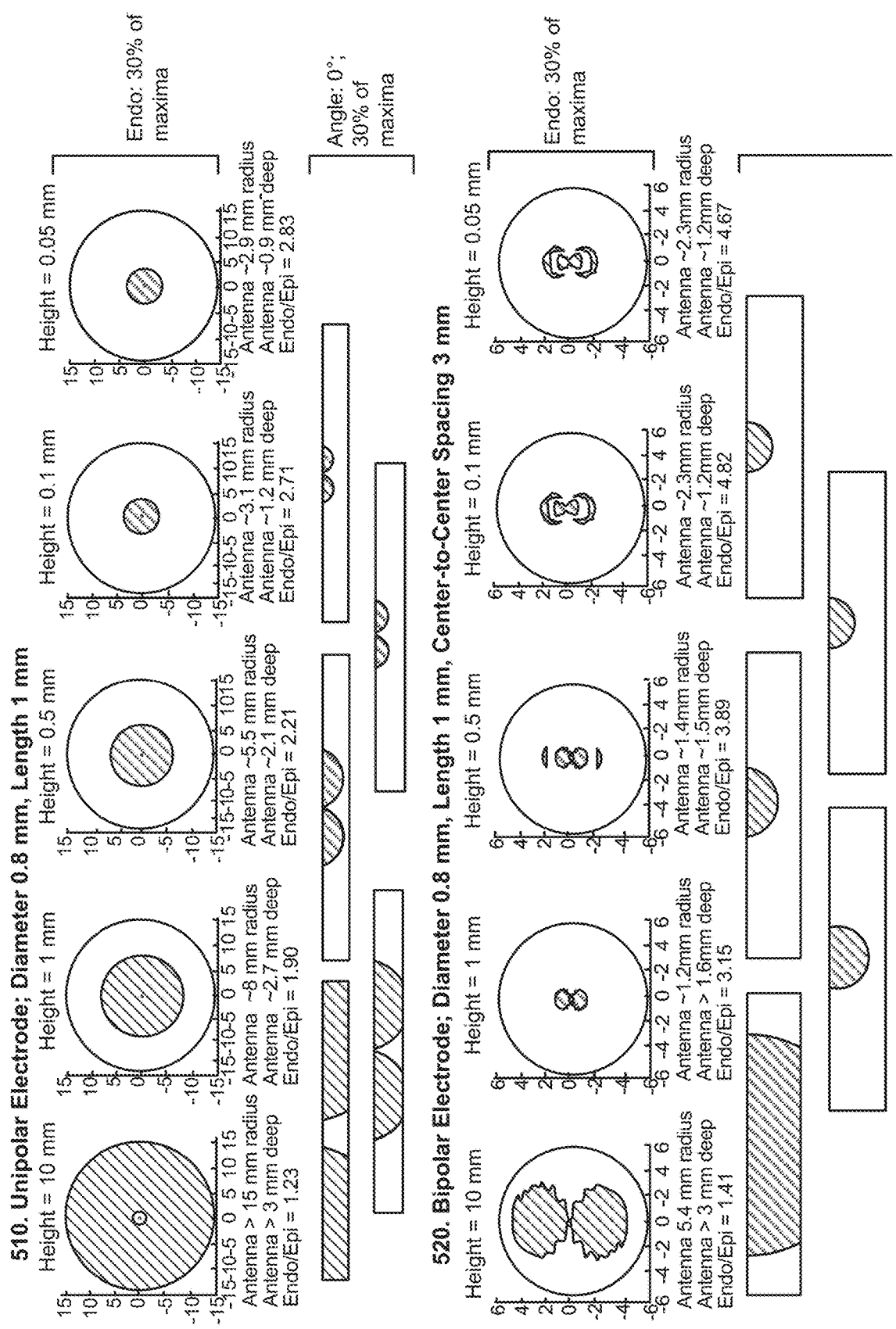

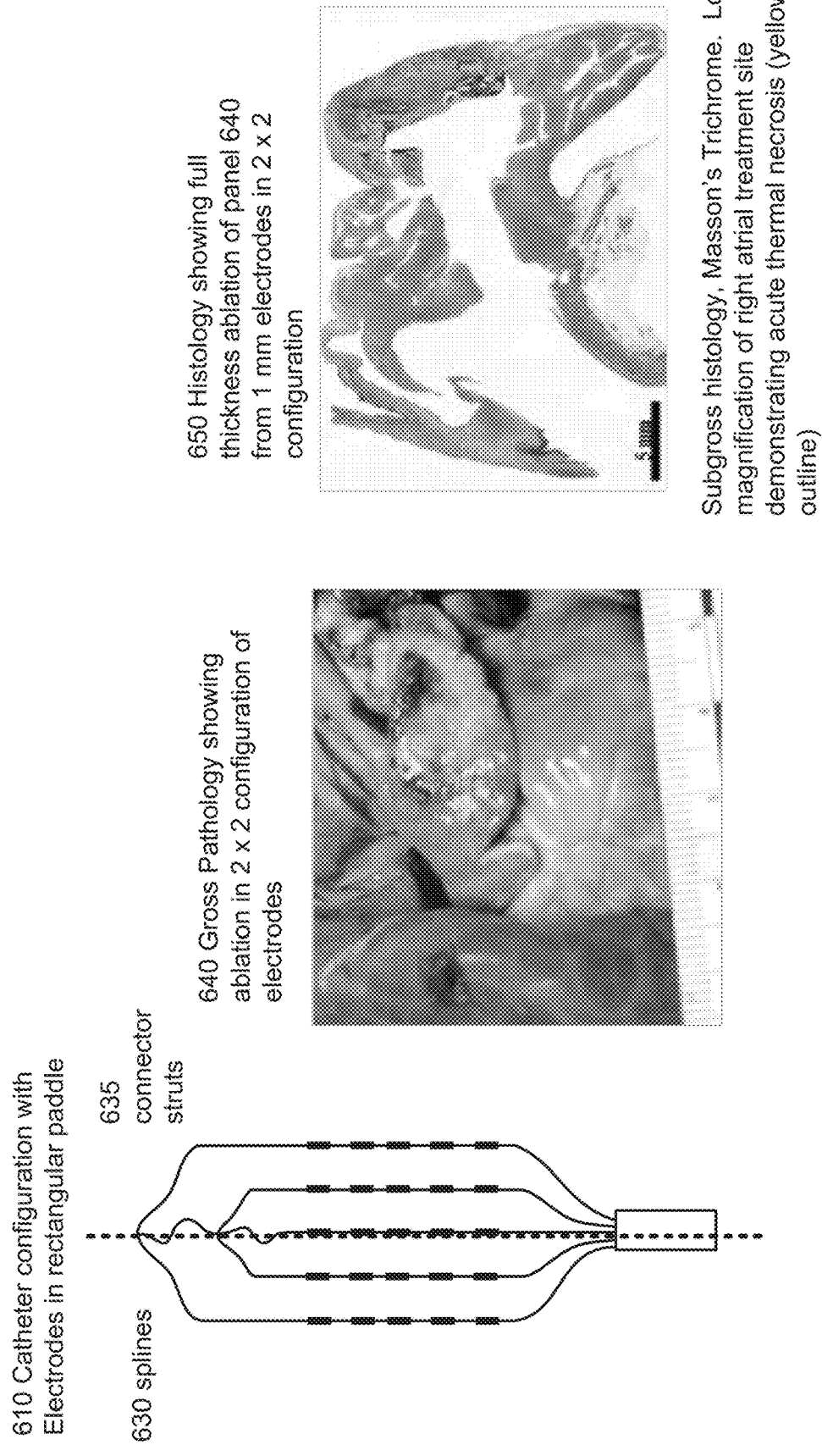
FIG. 6. Ablation from Array of Small Electrodes

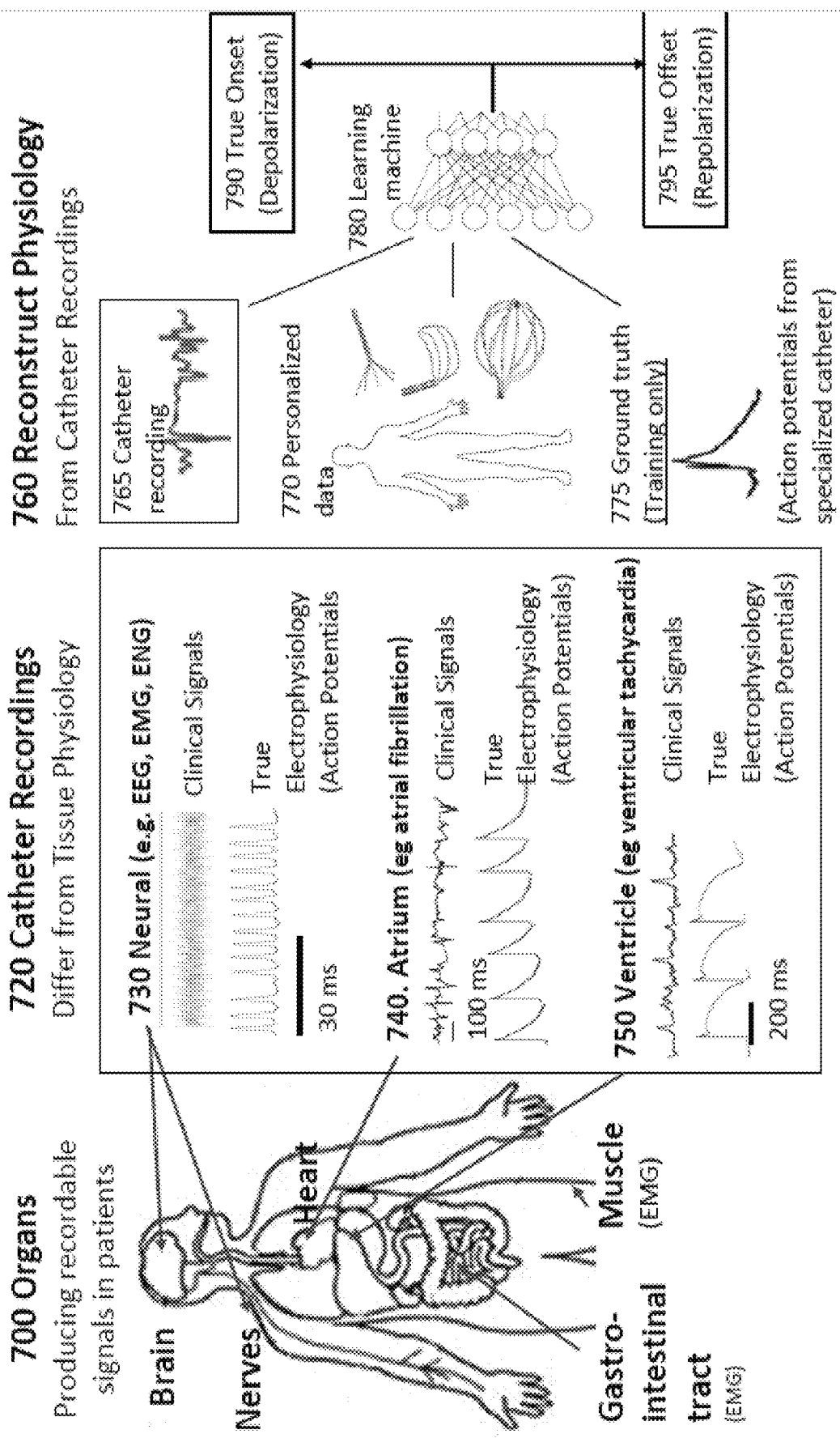
FIG. 7. Accuracy of Mapping - Reconstruct Physiological Signals from Catheter Recordings

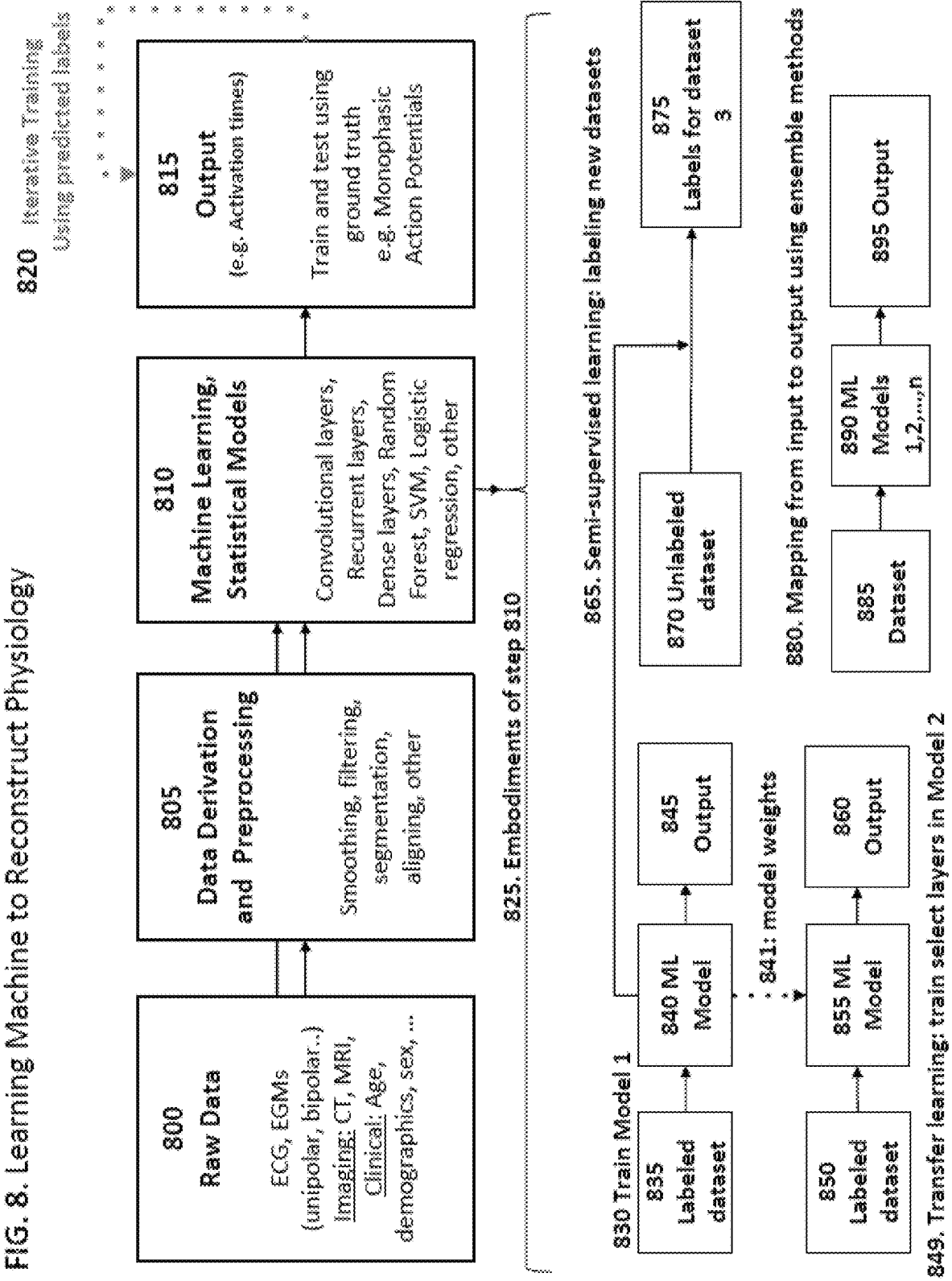
FIG. 8. Learning Machine to Reconstruct Physiology

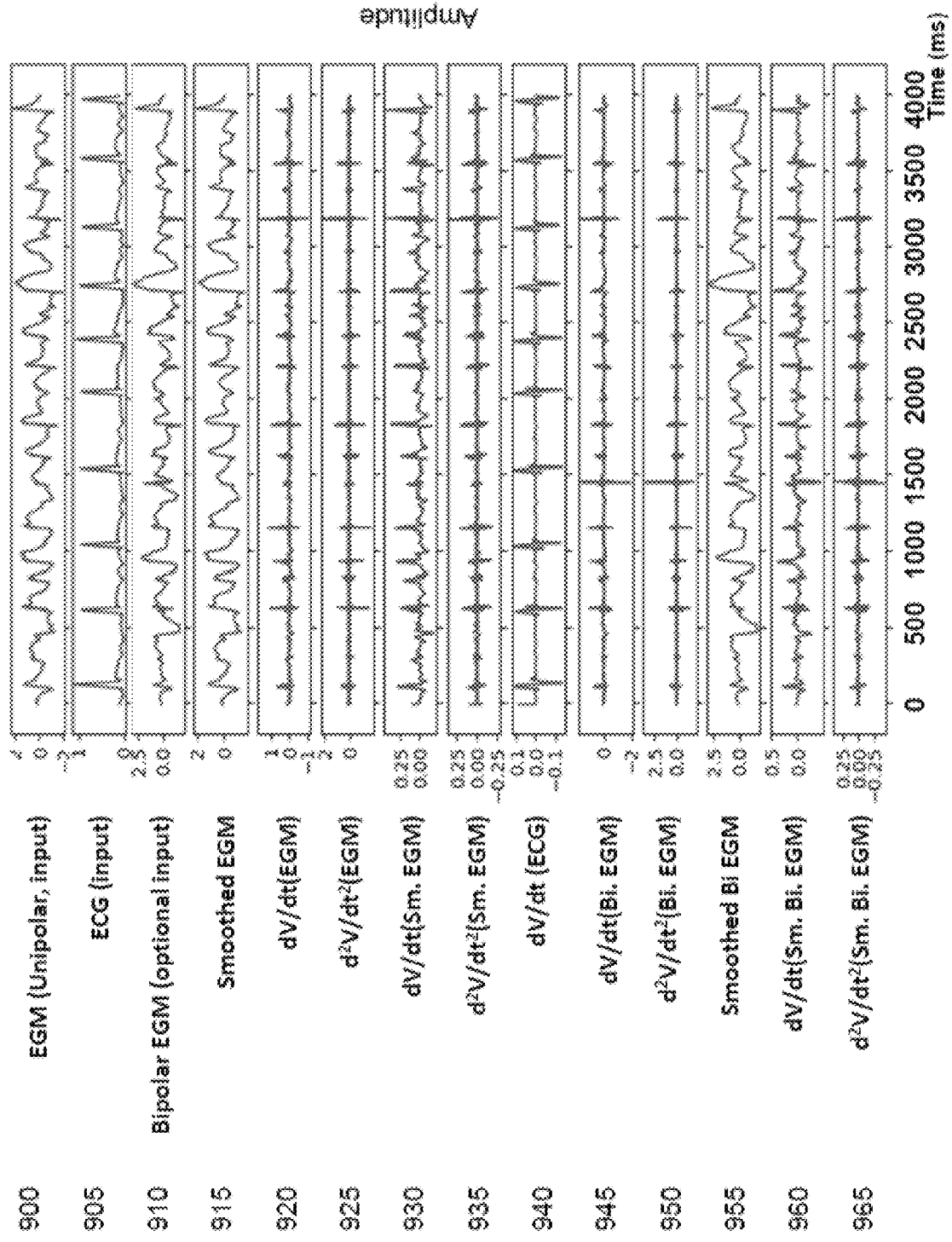

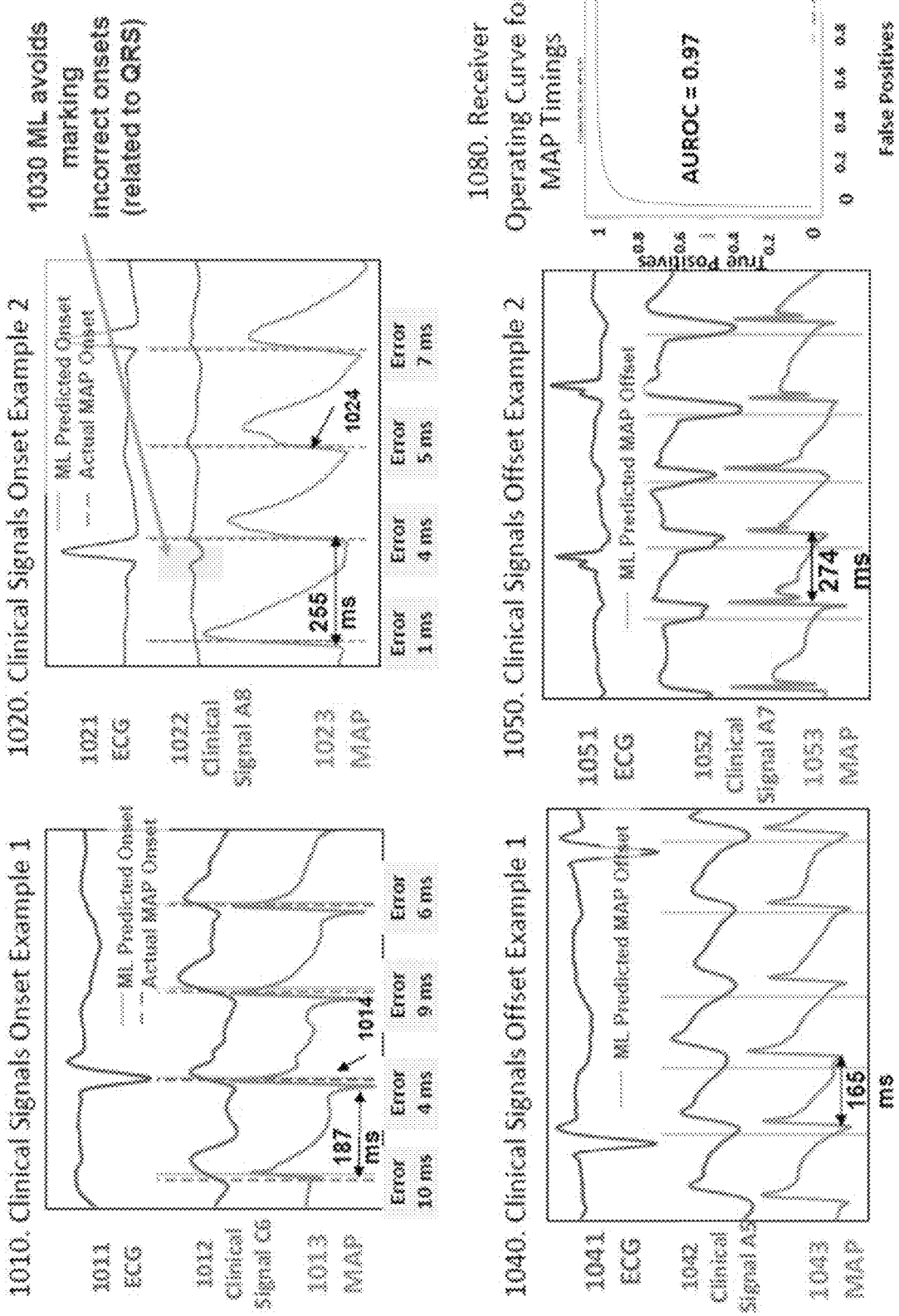
FIG. 10. Reconstruct Tissue Electrophysiology from Clinical Signals (Atrial Fibrillation)

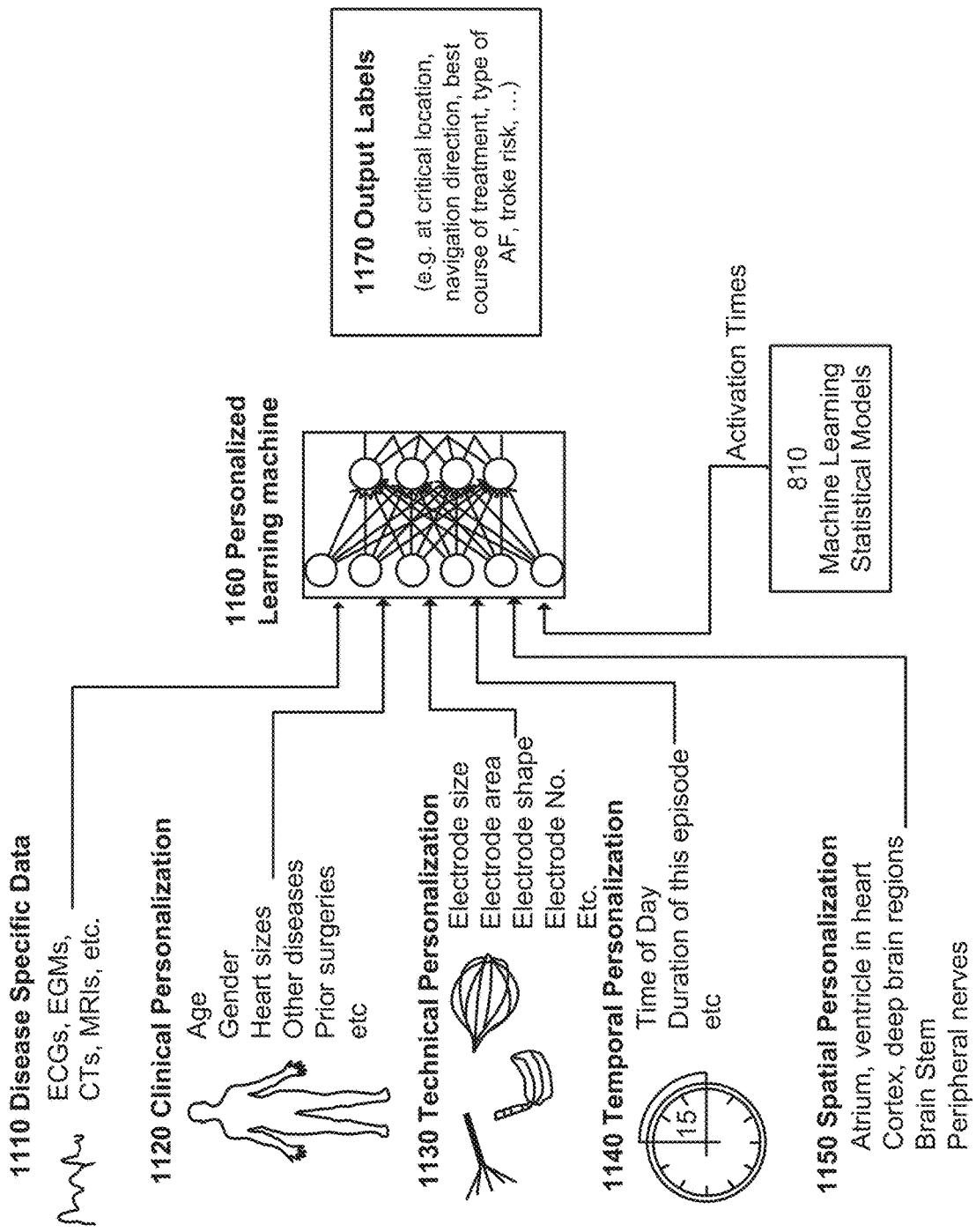

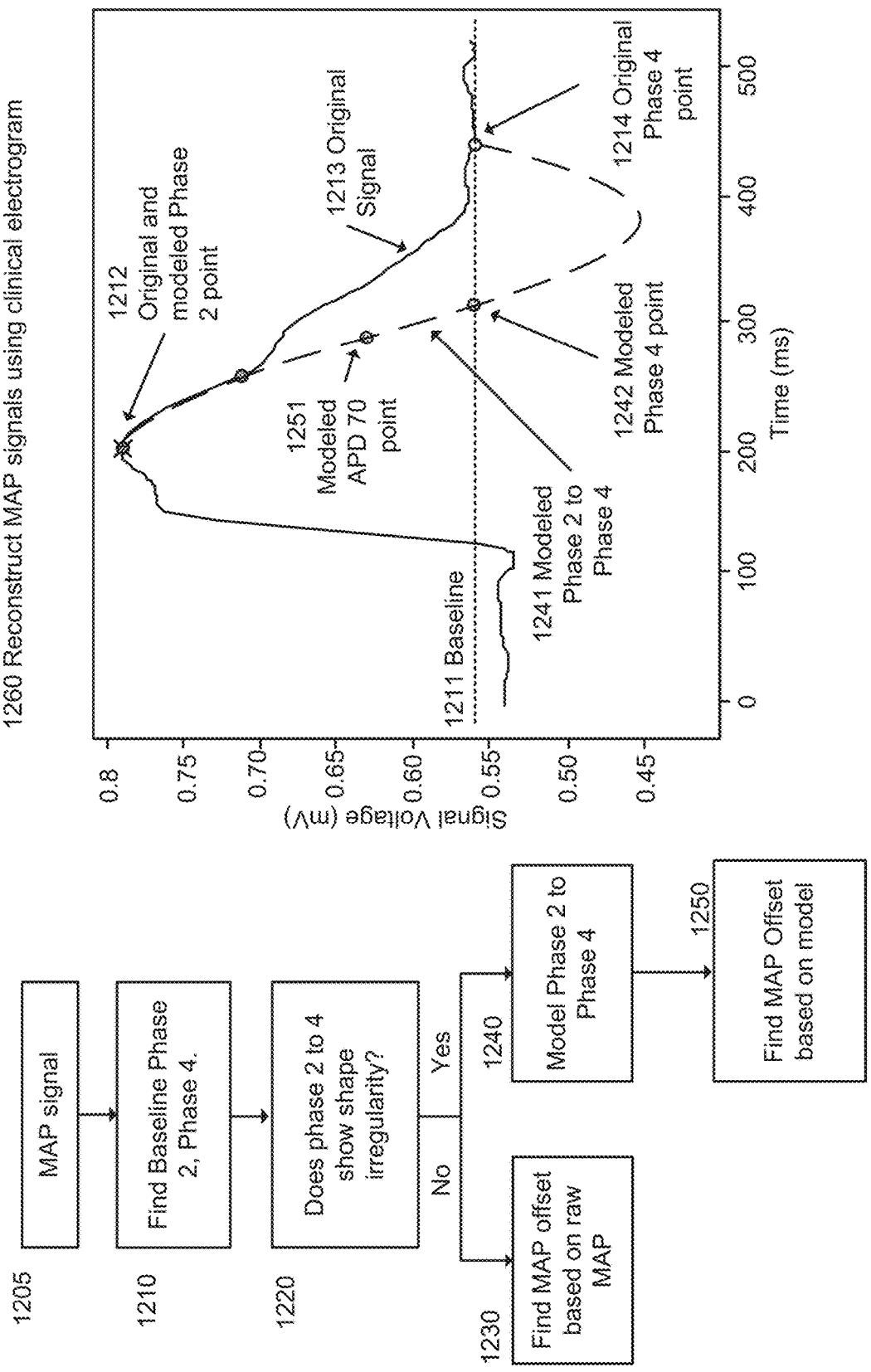
FIG. 12. Computational Reconstruction of Tissue Physiology Signals

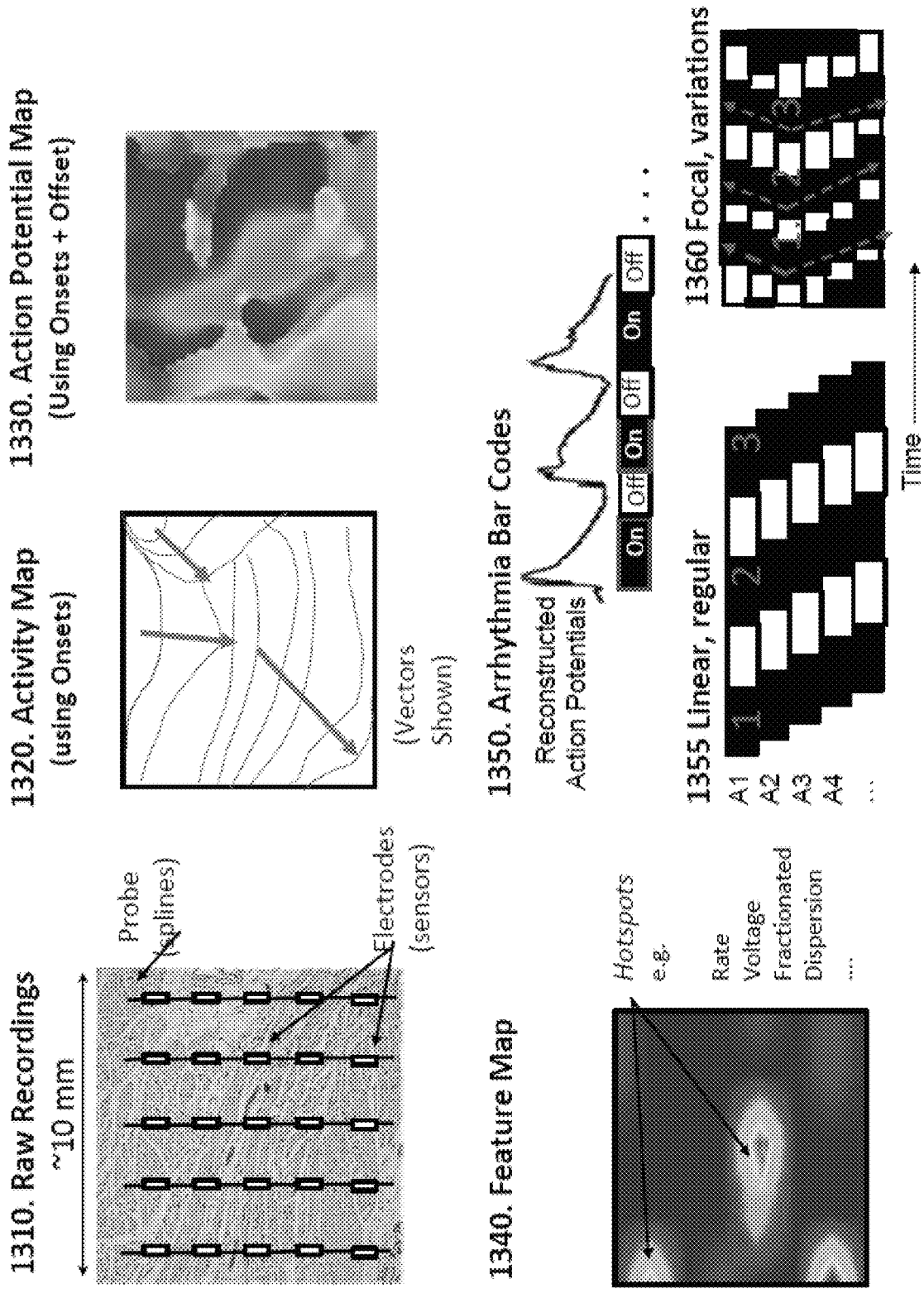

FIG. 14. Types of Spatial Feature that can be identified

1400. Focal
1405. Complete Rotation(s)
1410. Incomplete Rotation(s)
1415. Rapid Rate
1420. Complex Signal
1430. Conduction Slowing
1435. Repeating pattern
1440. Scar, Gap
  gap
  scar
1460. User Definable (e.g. draw on smartphone)
  Define
  + Clinical
1465. AI personalized for that patient (e.g. clusters)
1470. Feature Library
  • This Patient
  • Different patient
  'Similar' profile

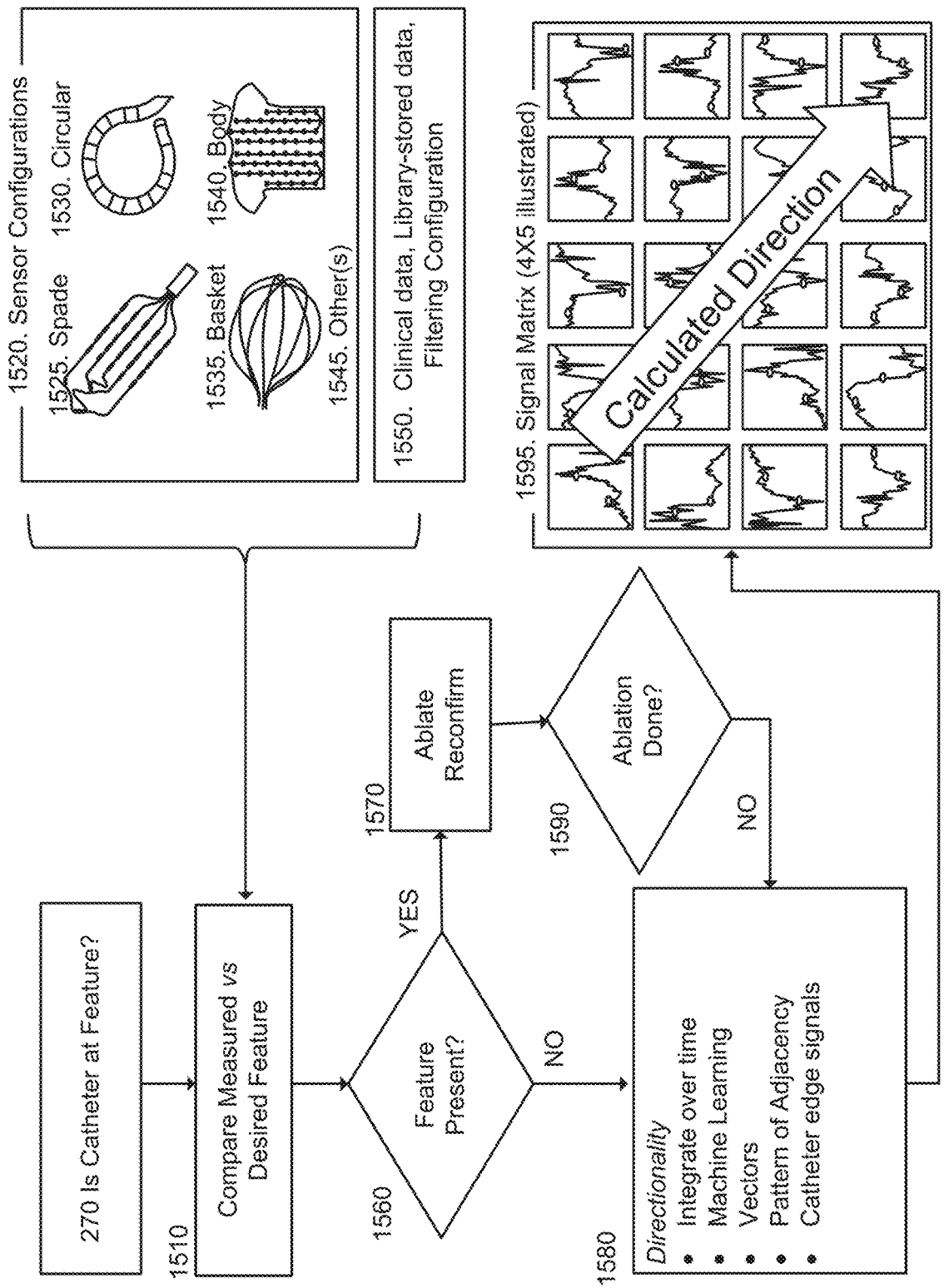
FIG. 15. Directional Guidance Logic

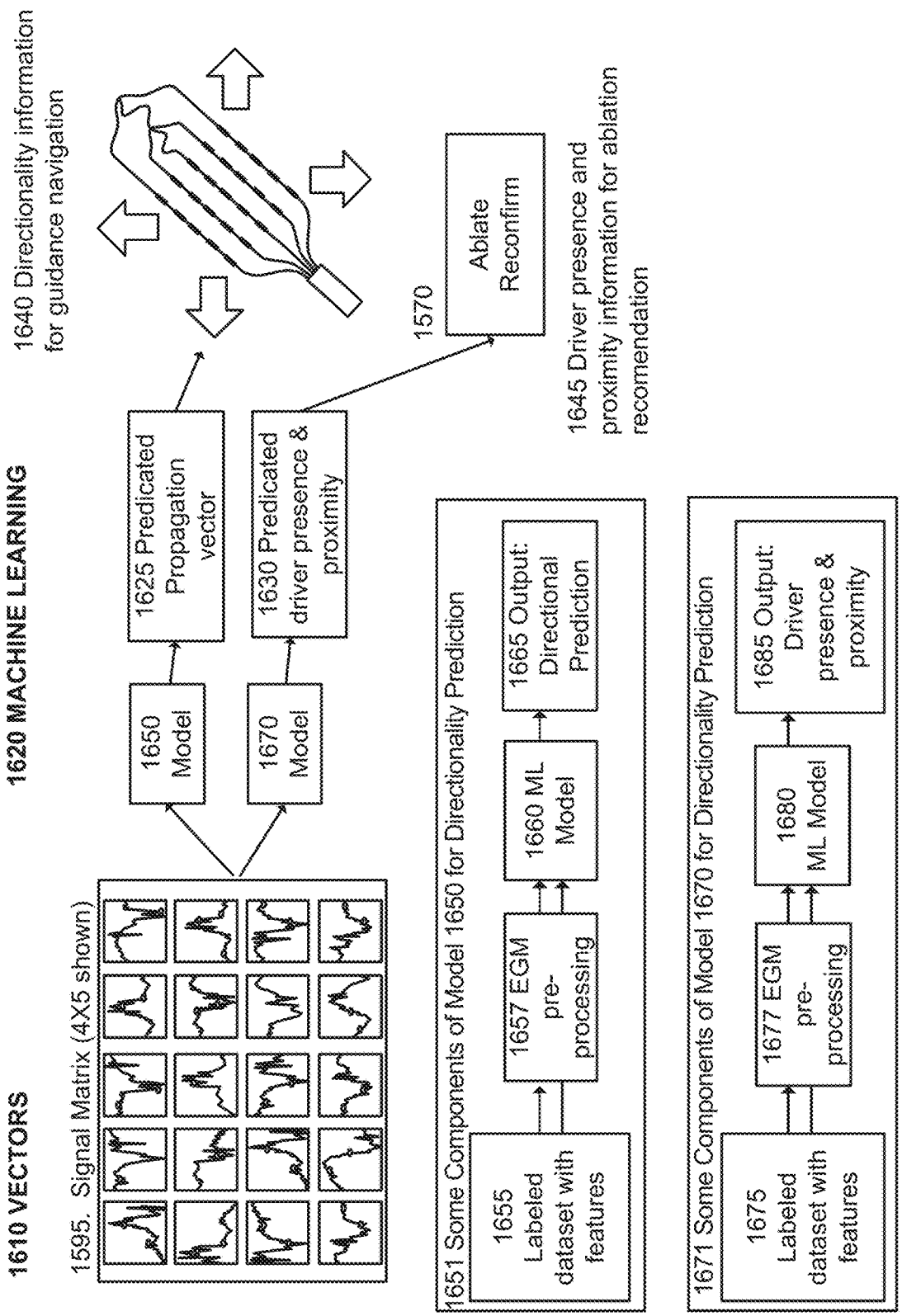
FIG. 16. Control System – Details of Directional Guidance Algorithm

SYSTEM AND METHOD FOR DIAGNOSING AND TREATING BIOLOGICAL RHYTHM DISORDERS

CROSS REFERENCE TO RELATED APPLICATIONS

The present application is a continuation of U.S. application Ser. No. 17/708,991 filed on Mar. 30, 2022, which claims the benefit of U.S. Provisional Application No. 63/283,901 filed on Nov. 29, 2021, both which are incorporated by reference in their entirety.

BACKGROUND

Field of the Art

This present disclosure generally relates to systems for the diagnosis and treatment of biological rhythm disorders in patients, including dual purpose catheters that both sense biological signals and deliver therapy to critical regions to treat the rhythm disorder, and algorithms and software that identify critical regions of the rhythm disorder and provide navigational guidance to direct a device towards such regions.

Conventional diagnosis and treatment of biological rhythm disorders uses a suite of tools to sense signals, to build a map that can be interpreted to identify critical regions of the disorder, and to deliver therapy to critical regions to treat the rhythm disorder. This typically requires using several hardware and software tools which must be exchanged through the limited number of patient access sites during a procedure. The need for several tools introduces inefficiencies in time and cost, and may also introduce errors and reduce procedural success. These issues are amplified if multiple cycles of mapping, diagnosis and therapy are repeated. There is a need for a system that integrates these functions to improve efficiencies of time and cost, and to raise the accuracy of diagnosis and effectiveness of therapy.

SUMMARY

The present invention relates to a heart treatment system and method to diagnose and treat complex or simple biological rhythm disorders in patients. The invention comprises a device (e.g. catheter) to sense signals with sufficient spatial and temporal resolution to map critical regions for complex rhythm disorders, and deliver therapy (e.g. ablation) to eliminate said critical regions. The invention further comprises software to calculate a guidance direction to move a device towards one or more critical regions, and diagnose when said device has reached said critical region. In one or more embodiments these functionalities are combined into a single catheter with associated software. In one or more embodiments, the physician can use the device to determine the adequacy of therapy immediately, and choose to repeat therapy, move the device to a subsequent region, or end the procedure. In one or more embodiments, critical regions can be defined by the operator, calculated by the invention or obtained from a library of prior successful cases. The invention introduces efficiencies of time and cost, and improves the success of therapy for complex and simple rhythm disorders.

In one or more embodiments, the catheter comprises a housing that contains one or more electrodes for sensing electrical signals and/or for delivering ablation energy to tissue. The catheter can be optimized to treat biological rhythm disorders. In one embodiment, the components or housing is designed as a plurality of splines on which an electrode array is disposed. The electrode array comprises a plurality of electrodes, wherein each electrode can be configured to sense electrical signals or to deliver ablation energy to tissue or both. Alternatively, there may be some electrodes for sensing electrical signals and some to deliver ablation energy. Thus, the device can be designed with individual electrodes that have a single function or that have a dual function, or a combination of both types of electrodes—and in either case, the overall electrode array itself may provide dual functionality. The dual functionality of the electrode array for sensing and therapy delivery simplifies the treatment process, as it enables the catheter to be guided towards a critical region for the rhythm disorder including a source by software system or logic, based on optimal sensing and interpretation of patterns of electrical signals, and enables the same catheter to deliver ablation energy in a pattern or patterns optimized for the biological rhythm disorder in this specific patient. The catheter is further described in U.S. Provisional Application No. 63/231,669 filed on Aug. 10, 2021, which is incorporated herein by reference.

In other embodiments, the catheter comprises sensing elements for mechanical motion of the heart such as ultrasound or piezoelectric sensors, and therapy elements that can use focused mechanical therapy such as ultrasound or shock wave therapy. As will be apparent from one skilled in the art, elements may be mixed across modalities, such as sensing mechanical motion by ultrasound and delivering electromagnetic ablation energy for therapy.

In one or more embodiments, the catheter comprises splines that may take the shape of a straight line, the arc of a circle, a zig-zag, or other shape as optimal for the specific biological rhythm disorder under consideration in each patient. In one or more embodiments, the catheter includes a plurality of connector struts attached to the splines. The connector struts are composed of a substantially rigid but deformable material including one or more pre-shaped bends designed to store compressive energy. When the splines are retracted into a sheath or introducer tool (henceforth referred to as sheath), they collapse in proximity to one another enabling the catheter to be accommodated within a guide catheter of smaller dimensions to be advanced into the organ or withdrawn from it. Collapsing the splines deforms the connector struts so that the splines oppose geometrically in the sheath without the need for undue force, thereby storing compressive energy in the bends. When the splines are extended from the sheath, the compressive energy stored in the connectors is released, returning the connector struts to a relaxed state where the splines are spaced apart from one another in their sensing and ablating configuration. The implementation of the connector struts provides for a creative solution for easy expansion and collapse of the catheter from the sheath.

In one or more embodiments, the catheter includes a plurality of irrigation pores that may be associated with the electrode array, for example interlaced within the electrode array. The irrigation pores provide controlled irrigation of saline or other solvents during ablation by the catheter. Irrigation while ablating tissue reduces and prevents charring of tissue from the ablation, enables delivery of power deeper within tissue due to cooling, and may enhance ablation by the chemical properties of the irrigating solution.

In one or more embodiments, a method is disclosed for optimizing the configuration of the electrode array for a particular patient. The method includes sensing signals of the patient (e.g., via an invasive or a non-invasive diagnostic device) and selecting an optimized portion of sensing elements from those on the array based on sensed signals for that patient. In a different embodiment, a physician selects one catheter that best matches the optimal array size and configuration for this patient, from a range of catheters with different sensing array configurations. Having selected the optimal catheter configuration, the physician can select, or the software can suggest, the optimal filtering, combination of sensing elements, for electrical signals whether to use unipolar or bipolar recording mode, and tailored mapping and directional elements, to enable best treatment for the patient's biological rhythm disorder.

In some embodiments, the system can identify and locate critical regions for rhythm disorders in the heart. The one or more biological signal patterns that can be selected by the physician include, but are not limited to, a focal source of a complex rhythm disorder such as atrial fibrillation or ventricular tachycardia, a localized reentrant site for a complex rhythm disorder such as atrial fibrillation or ventricular tachycardia, a focal source for a simple rhythm disorder such as atrial tachycardia, a reentrant source for a simple rhythm disorder such as atrial tachycardia, regions of scar or fibrosis or regions bordering sites of scar or fibrosis, which may be important for rhythm disorders in the atrium or ventricle.

The one or more desired patterns may represent specific features of electrogram shapes (fractionated, complex or simple electrograms), voltages (low voltage indicating scar or borderzone of scar), high rate (or dominant frequency or other frequency patterns), temporal relationship of electrograms in the recorded area (electrograms spanning a larger or smaller proportion of the cycle length), spatial arrangement of electrograms (such as indicating a pattern of spatial dispersion, rotation or centrifugal spread), or machine learned patterns that indicate the presence of a critical region.

The system provides guidance towards critical regions for the rhythm disorder. Such guidance may include, but is not limited to, a spatial direction along the tissue, a spatial direction to a different portion of the chamber or a different chamber entirely (for instance the right atrium rather than left atrium), a spatial direction towards or away from tissue to provide more or less contact force, changing the physical configuration of the catheter, changing the configuration of the catheter against tissue (e.g. rotation, or bending), or swapping out a more suitable catheter. Guidance could also be an indication that this rhythm is highly treatable or not treatable (i.e. a display of confidence in therapy).

In one embodiment, spatial directional guidance is provided by computer model. The computer model may identify the pattern of electrical activity recorded at the current position of the catheter, may determine if this matches one or more patterns desired by a physician and, if it does not, may calculate the direction required to move the catheter towards said one or more desired patterns. In various embodiments, directionality is determined by an analysis of spatial vectors, of patterns of rate across the organ, by machine learned patterns that indicate adjacency to a critical region, or machine learned patterns that indicate direction to a critical region. Several methods for directionality are disclosed herein.

In some embodiments, diagnosis and treatment can be estimated based on knowledge of how patients with similar signal patterns respond to therapy, in addition to or instead of the actual patterns recorded in this patient at this specific time. A library of stored patterns (also termed "arrhythmia landscapes") can be developed that includes recorded electrical data, electrode configuration, features identified from these recordings, patient demographics (including but not limited to age, gender, type of rhythm disturbance, cardiac structure and function), and success of therapy. The library can include data from this patient recorded at different procedures that were successful or unsuccessful. The library can also include data from multiple individuals, which creates a digital classification that can be updated using strategies such as crowd-sourcing, or manual addition of cases with both successful and unsuccessful outcomes. This enables learning on an ongoing basis.

Estimated diagnosis can be provided in several ways. Actual patterns recorded in that patient can be compared against stored patterns using several techniques including machine learning, statistical association, similarity measures such as correlation coefficients, computer models based on the physics of how rhythm patterns will change in response to altered cellular, organ-level or patient-level characteristics, and other techniques. The comparison against stored patterns can be used to estimate which critical sites should be treated to achieve a successful outcome, or which sites should not be treated to avoid an adverse outcome. Comparison against stored patterns may be used to reduce uncertainty in assigning a mapped feature, calculating directionality or recommending therapy. For instance, if sensed signal patterns in a patient indicate similar probabilities for two or more choices, comparison against stored patterns can be used to select between these choices. The comparison against stored patterns can also be used to optimize hardware use in that patient: selecting an optimal subset of electrodes from an array for signal detection, an optimal subset of electrodes to deliver therapy, or an entirely different catheter.

This same catheter can then be used to directly deliver treatment to regions of interest (or critical regions). In some embodiments, the spatial configuration of ablative electrodes enables the physician to deliver therapy in shapes tailored to the specific rhythm in a patient. Such shaped ablation may comprise a circle of ablation that isolates a critical region or ablates around a sensitive structure, an ablation arc of varying curvatures (from linear to curved) such as to connect regions of scar, a pattern that ablates electrodes only detecting viable tissue and skips those overlying scar, a scattered pattern or ablation in a block or 'cluster' of lesions covering some or all electrodes in the catheter configuration.

In some embodiments, a process can identify individuals amenable to therapy for treating complex rhythm disorders, provides directional guidance in 3 dimensions to move a sensor device towards optimal locations for therapy, and enable therapy to tissue at this location. In some embodiments, a non-invasive wearable device may be used by the patient at home, without hospital visits, to determine if ablation is likely to be successful or if drug therapy should be continued. This greatly improves outpatient workflow, and reduces unsuccessful procedures by better patient selection. Another embodiment is a system providing a personalized diagnosis of rhythm disorders and a 'single shot' sensor/therapy tool. Some embodiments, which are not intended to be limiting, include cardiac applications in heart rhythm disorders, coronary artery disease and in heart failure.

The system and method described herein thus provide a process for personalized therapy for biological rhythm disorders. The process is simplified and expedited because the same apparatus provides high-resolution mapping of the rhythm disorder, navigational guidance to critical regions of interest, and delivers therapy in a fashion tailored to the patient. This can increase efficiency of the procedure. The system can be used in conjunction with other therapy which may include a combination of lifestyle changes, medications, electrical or mechanical therapy, surgical or minimally invasive ablation from other catheter systems, genetic or stem cell therapy or other options which will be familiar to one skilled in the art.

BRIEF DESCRIPTION OF THE DRAWINGS

FIG. 2 illustrates an overall operation of the control system, in accordance with one or more embodiments.

FIG. 3 illustrates a methodology for optimizing a catheter, in accordance with one or more embodiments.

FIG. 4A illustrates the varying impact that electrode configurations of the catheter have on field of view, in accordance with one or more embodiments.

FIG. 4B illustrates the varying impact that electrode configurations of the catheter have on field of view, in accordance with one or more embodiments.

FIG. 5 illustrates the varying impact that electrode configurations of the catheter have on depth of view, in accordance with one or more embodiments.

FIG. 6 illustrates results of an example ablation procedure performed by the heart treatment device on a pig heart, in accordance with one or more embodiments.

FIG. 7 illustrates a reconstruction model for recreating electrophysiological signals from electrical signals sensed by the catheter of the heart treatment device, in accordance with one or more embodiments.

FIG. 8 illustrates implementation of the reconstruction model as a machine-learned model, in accordance with one or more embodiments.

FIG. 9 illustrates sample input features for the reconstruction model from atrial fibrillation of the heart, in accordance with one or more embodiments.

FIG. 10 illustrates reconstruction results of the reconstruction model from atrial fibrillation, in accordance with one or more embodiments.

FIG. 11 illustrates a personalization model for personalizing treatment for an individual, in accordance with one or more embodiments.

FIG. 12 illustrates implementation of the reconstruction model using computational techniques, in accordance with one or more embodiments.

FIG. 13 illustrates possible spatial maps that may be generated by a featurization model, in accordance with one or more embodiments.

FIG. 14 illustrates possible spatial features that may be identified by a featurization model, in accordance with one or more embodiments.

FIG. 15 illustrates a guidance model for determining a guidance direction for the catheter of the heart treatment device, in accordance with one or more embodiments.

FIG. 16 illustrates implementation of the guidance model as a machine-learned model, in accordance with one or more embodiments.

Figure 1A:
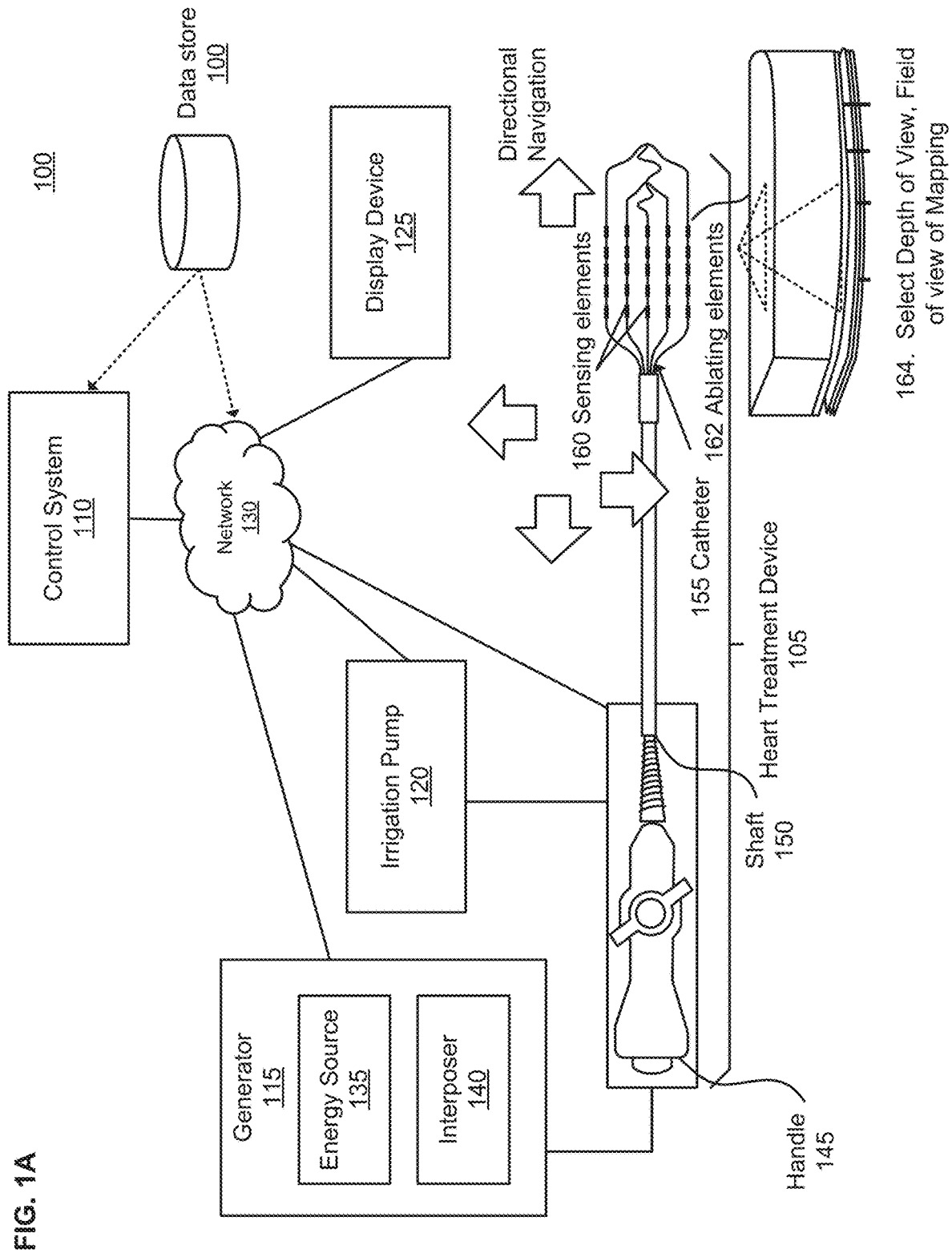
FIG. 1A is an overview of a heart treatment system, in accordance with one or more embodiments.

In each figure, there can be more or fewer components and/or steps than shown, or certain components and/or steps can be replaced with others or can be organized or ordered in a different manner than is shown.

DETAILED DESCRIPTION

Overview

The present invention relates to a heart treatment system for use in a diagnostic and/or treatment device for the management of biological rhythm disorders, comprising a catheter and a control system for mapping and identification of important regions of a biological rhythm disorder (also termed critical regions, sources) for therapy. The catheter is capable of both sensing electrical signals in tissue and treating selected regions. The control system is a computing device that implements analytical software capable of detecting multiple types of critical regions, selectable by the physician for the patient being treated. The analytical software provides the ability to indicate direction towards a critical region or source, if the catheter is not currently at such a region.

The system and method described herein thus provide a process for personalized therapy for heart rhythm disorders, that is also simplified because it combines high-resolution mapping of the biological rhythm disorder, navigational guidance to critical regions of interest, then tailored therapy for the rhythm disorder from the same apparatus. This can also increase efficiency of the procedure.

The treatment system is an improvement over conventional systems by implementing a small and efficient probe to identify localized critical regions within a 'global' problem such as treatable regions for fibrillation within the entire heart, or treatable sources of seizures within the entire brain. Uniquely, the device can diagnose a critical region for the biological rhythm disorder if present at the current device location but also, if it is not present, provide a guidance direction to a critical region. This functionality dispenses with the need for wide-area 'global' mapping as used in conventional systems. A useful analogy for this invention is that it directs the physician to a critical region similar to the way that satellite navigation or global positioning systems can direct the driver to a desired location without requiring an entire map of the world (i.e. a global map) or requiring the operator to estimate directions mentally.

In terms of recording apparatus, many systems for recording or mapping biological rhythm disorders in the prior art fall short in various respects. Some conventional utilize non-ideal recording probe shapes such as linear probes, spheres or other shapes that cannot conform well to the internal or external surface of organs. Some conventional recording systems do not provide high spatial resolution because they distribute recording elements over a wide area. Therefore, they cannot readily be adapted to diagnose critical regions of a rhythm disorder or deliver therapy with the precision and uniformity of smaller therapy devices. Wide area recordings in conventional systems have also been achieved by non-contact mapping with electrical signals inferred by so-called 'inverse solution' mathematics, but those systems have been shown to introduce spatial errors in finding critical regions, and temporal errors on the order of tens of milliseconds compared to signals from a contact probe, which may limit their ability to accurately diagnose or delivery therapy.

The current invention provides a high resolution recording probe that can confirm to curved or planar internal or external surfaces of organs such as the heart, or bladder, or other organs. The spatial resolution is sufficiently high to record and diagnose critical regions with accuracy. The spatial resolution is sufficiently high that therapy from treating elements on the device will be delivered with spatial precision and will not miss regions or lead to gaps. This applies to therapies such as ablation for the heart.

In terms of diagnostic functionality, the current invention provides the diagnostic ability to identify patients who will respond to specific therapy. An example of this embodiment is to identify patients with atrial fibrillation who are likely or unlikely to benefit from ablation by pulmonary vein isolation (PVI). If critical regions for a patient's AF arise near the pulmonary veins, then PVI is likely to work. If critical regions (or sources) lie in other regions, PVI is less likely to work. The device can then identify these other regions. Such critical regions may be amenable to therapy such as ablation, which can be delivered by this device. The same logic applies to other biological rhythm disorders.

In terms of diagnosis, further advantages of this invention are its ability to record and map the presence of critical regions for simple as well as complex rhythm disorders, and to indicate directionality to such regions if the recording probe is not currently at such a site.

For simplicity of discussion, the device is discussed in relation to embodiments for heart rhythm disorders such as atrial fibrillation (AF). However, the discussion may be applied to other types of biological rhythm disorders arising from misaligned electrical signals in biological tissue. Other heart rhythms include focal tachycardia, macro-reentrant tachycardia, micro-reentrant tachycardia, or fibrillation. Each of these can apply to the atrium or ventricle or other structures such as the aortic cusps, sinuses of Valsalva, venous structures such as the superior or inferior vena cava, pulmonary veins, or coronary sinus.

The process may apply to other disorders of the heart including mechanical contraction, of heart failure, of abnormalities of the coronary blood vessels that supply the heart with blood, or of nerve-related function ("the autonomic nervous system"). Other exemplary applications include electrical disorders of the brain including seizure disorders, diseases of gastro-intestinal rhythm such as irritable bowel syndrome, and bladder disease including detrusor instability. The process may apply to chaotic disorders in these organs, such as atrial fibrillation in the heart or generalized seizures in the brain, as well as simple rhythm disorders. These examples are in no way designed to limit the scope of the disclosure for other conditions. This can be applied to organized sources or drivers for a heart rhythm disorder such as atrial fibrillation or ventricular fibrillation. This also applies to the one or more sources driving tonic/clonic seizures in the brain. This also applies to a focus that drives irritable bowel syndrome. These features of critical regions for the heart rhythm disorder are used to design the size and configuration of electrodes for optimal detection, and the configuration and pattern of ablation therapy delivery for optimal treatment planning.

Treatment may also include, in addition to ablation therapy: immunosuppression therapy, stem cell therapy, gene therapy, drug therapy, other types of medical therapies, or any combination thereof. The system can be used in conjunction with other therapy which may include a combination of lifestyle changes, medications, electrical or mechanical therapy, surgical or minimally invasive ablation from other catheter systems, genetic or stem cell therapy. In some embodiments, the system and process has the ability to deliver personalized therapy using data from the current individual but also to estimate therapy using machine learning of data from other individuals with similar profiles.

Definitions

In some embodiments, "associative learning" may refer to a process of linking input data with measurable physiology or clinical outcome. Associative learning may be iterative, enabling associations to be modified ("learned") based upon patterns of change between input and measured output (physiological or clinical endpoints).

In some embodiments, "biological signal" may refer to a signal produced by the body of a subject, and may reflect the state of one or more bodily systems. For instance, the heart rate reflects cardiac function, autonomic tone and other factors.

In some embodiments, "biometric signals" may refer to signals that provide metrics of human characteristics. Biometric identifiers can be physiological or behavioral. Physiological biometrics include, but are not limited to, DNA, fingerprints or palm prints, mouth swabs, tissue or urine samples, retinal images, facial recognition, the geometry of hands or feet, recognition of the iris or odor/scent of an individual. Physiological biometrics may also include signals such as vital signs, the ECG, the EEG, EMG, and so on. Behavioral biometrics include patterns such as gait during walking or typing rhythm. Embodiments described in this disclosure may use dynamic patterns of combined physiological and behavioral biometrics over time, which adapt to changes in the individual and are thus robust to forgery from prior "versions" of a person's signature.

In some embodiments, "body" may refer to the physical structure of a human or an animal for veterinary work.

In some embodiments, "critical region" or "regions" refers to a physician's desired treatment target for a biological rhythm disorder. This may be one or more sources for the rhythm disorder, where therapy can terminate said rhythm, or one or more regions where therapy could modulate said rhythm, for instance by slowing it down, or converting it to a less troublesome form (for instance converting atrial fibrillation to atrial flutter, or slowing the rate of a tachycardia). Critical regions may also be sites where therapy may not have a clear immediate impact yet make next treatment steps easier. In some embodiments, 'critical region' is equivalent to 'source' or 'region of interest'. In other embodiments, 'critical region' is a region to avoid during therapy, such as a sensitive structure near the heart (the phrenic nerve, esophagus or blood vessels).

In some embodiments, multiple critical sources can be identified. This will depend on the field of view of the sensing array. In cases where global mapping is available, sites can be identified within the entire organ. By way of example, this may be achieved with a basket catheter that covers the majority of a heart chamber, using body surface mapping of the heart (e.g., as described in U.S. Provisional Application No. 63/175,986 filed on Apr. 16, 2021, which is incorporated herein by reference), using surface mapping of the brain or a large multipolar catheter in the bladder. In cases where mapping is regional, sites will be identified within this field of view relative to that position of the recording array in the organ.

In some embodiments, when the invention identifies multiple sources, critical sites can be ranked by their priority for therapy within the recording field of view. Several ranking approaches can be used as discussed below.

In some embodiments, "data streams" or "stream(s) of data" or "data" may refer to biological data sensed by one or more sensors that can provide real-time or near-real-time information on the biological process being sensed. Sensors in the heart may provide data comprising the electrocardiogram (ECG), Electrogram (EGM), pulse rate, pulse waveform and cardiac hemodynamics. Other data may include cardiac acoustics, including analysis of heart sounds, murmurs and sophisticated analyses of hemodynamics related to the heart. Lung function may be sensed as chest movement, auscultatory sounds and nerve firing associated with breathing. Gastrointestinal disease may be sensed as sounds (borborygmi), movement on the abdominal wall, and electrical signals related to smooth muscle activity of the gut. Central and peripheral nervous system activity may be sensed as nerve activity on the scalp (electroencephalogram, EEG), remote from the scalp but still reflecting the EEG, and from peripheral nerve firing.

In some embodiments, "demographics" may refer to personal information which may include, but is not limited to, age, gender, family history of disease, ethnicity, and presence of comorbidities and which may be clinically relevant.

In some embodiments, "digital classification" may refer to a partition of different states of disease or health based on mathematical indexes. Traditional disease classifications are qualitative, such as "atrial fibrillation is more common in the older individuals, those with heart comorbidities such as valvular lesions or heart failure, those with metabolic syndrome". A digital classification translates this broad dataset into quantifiable primary and secondary data elements (data vectors). The likelihood that a disease entity $D_n$ is present in a specific individual is approximated by the probability $p(D_n)$:

$$p(D_n) = \sum_{i=1}^{m} \frac{(k_n p(V_{n,i}))}{k_n}$$

Where m is the number of available data input types, n is the disease being considered, and $p(V_{n,i})$ is the probability that data vector $V_{n,i}$ contributes to disease n for input i, and $k_n$ is a weighting constant for disease n. These elements are integrated into the classification, which computes probabilities that a specific data input contributes to disease. Probabilities can be obtained from population data, in which the profile of a specific person is matched to the most-similar individuals or profiles in that population. The probability can also be obtained from data in this individual alone, compared to times of health (self-reported or adjudicated) and times of disease (self-reported or adjudicated). These calculations can be performed by traditional estimating equations but may also by statistical techniques and machine learning. A digital classification (i.e. a classification) represents a disease entity stochastically by the aggregate of abnormalities in multiple related data inputs. This process is dynamic since the equation reflecting disease will change when data is added, when data changes, and when the state of health or disease is updated. This is an approach to integrate massive amounts of data from traditional data sources as well as wearable devices in an individual, or massive amounts of data from several individuals as a crowd-sourced paradigm.

In some embodiments, "electrocardiographic imaging (ECGI)" is a data source that refers to a process that records body surface potentials on the chest then uses mathematics to calculate electrical activity at precise regions of the heart. The inverse solution develops mathematical transforms that may need detailed knowledge of anatomy inside the chest, typically provided by computed tomography (CT) or magnetic resonance imaging (MRI), or from standardized anatomical databases, and make assumptions about their conductivity, resistance and other electrical properties. In this way, body surface potentials can be mapped to the heart.

In some embodiments, an "electrocardiographic (ECG) patch" may refer to a device that includes electrodes to sense cardiac rhythm. The ECG patch may be a data source. The ECG patch may be placed in regions of the body, such as on the back. Depending on the body placement and approaches used to analyze data generated by the ECG patch, the ECG patch can discriminate heart rhythm activation patterns of interest. In some embodiments, an ECG patch on the back can record atrial activation to guide AF therapy, which can be tailored to best record activity in women versus men, and for different rhythm applications. The ECG patch does not necessarily require CT or MM imaging for analysis, and is a form of body surface potential mapping without mapping the entire body torso.

In some embodiments, "electrogram" (EGM) refers to an electrical signal, such as that recorded by a sensor in the sensing array on the catheter.

In some embodiments, 'guidance direction' indicates a calculated spatial direction in which to move the recording array to reach a desired target, in particular a critical site for therapy for a biological rhythm disorder. This guidance can include both a spatial directionality as well as estimated distance. This is useful for determining which critical site is a priority for therapy as discussed below.

In some embodiments, "historical data" may refer to stored data, which may include reports from medical imaging, e.g., magnetic resonance imaging (MRI), computed tomography (CT), radiological, or other scans of an organ, data from genetic testing analyses (e.g., presence of one or more genomic variants), previously-obtained ECG reports, pathology, cytology, information on genomic variants (genetic abnormalities and non-disease causing variations), and other laboratory reports. This also includes clinical demographics such as age, gender, other conditions present in the individual, and a family history of diseases. Historical data may further include additional personal historical details that could be relevant to generating the personal digital record, for example, socioeconomic status including income strata, mental illness, employment in a high-stress profession, number of pregnancies (in women), engaging in high-risk behaviors such as smoking, drug or alcohol abuse, etc.

In some embodiments, the term "landscape" may refer to characteristics and patterns of activity present within the biological rhythm disturbance in that patient. In a simple landscape, one site drives biological rhythm in the entire chamber. Examples include the sinus node driving sinus rhythm, which can rarely be a target for therapy such as in inappropriate sinus tachycardia. Another example is a focal site driving atrial tachycardia or ventricular tachycardia, or premature contractions in the atrium or ventricle. Another example is the isthmus that maintains an organized reentrant circuit for atrial flutter or ventricular tachycardia. Moderately complex landscapes may involve a few (~2-3) discrete sites of interest, such as 2 competing atrial flutters maintained by distinct isthmuses (sites). A more complex landscape still may involve multiple competing and asynchronous sites which may drive AF (sources, regions of interest), of which one or more may be rotational or focal or other features (see 250 in FIG. 2), within intervening complex and disordered activity. Another source site for sinus node related arrhythmia or AF, in particular, is ganglionated plexus locations. These typically arise near the right and left pulmonary veins in the left atrium, near the sinus node in the right atrium, and at other patient specific locations. Landscape analysis (FIG. 2) is followed by identification of spatial features which may be used to classify the rhythm disturbance in that patient, and also as targets for personalized ablation therapy. For instance, AF initiated by triggers at the pulmonary veins may be treated by pulmonary vein ablation. Alternatively, AF maintained by driver sites elsewhere in the left or right atrium may be considered a different type (phenotype) of atrial fibrillation.

In some embodiments, "machine learning" (ML) may refer to analytic methods and algorithms that can learn from and make predictions on data by building a model. Machine learning can refer to deep learning or traditional machine learning methods. Machine learning is a branch of artificial intelligence (AI) that focuses on the development of computer programs that can automatically update and learn to produce predictions when exposed to data. In some embodiments, machine learning is one tool used to create the digital network and personal digital records linking sensed or recorded data with a specific output such as response to therapy, or ability to maintain normal rhythm. For applications in the brain, outputs could include absence of seizure activity. Machine learning techniques include supervised learning, transfer learning, semi-supervised learning, unsupervised learning, or reinforcement learning. Several other classifications may exist.

In some embodiments, "reinforcement learning" may refer to a form of machine learning which trains an agent to take actions in a specific environment to maximize cumulative reward. Reinforcement learning is often used in game theory, operations research, swarm intelligence, and genetic algorithms and has other names such as approximate dynamic programming. One implementation in machine learning is via formulation as a Markov Decision Process (MDP). Reinforcement learning may differ from supervised machine learning in that it may not use matched inputs and labeled outputs, and actions that result in sub-optimal rewards are not explicitly corrected (unlike supervised learning which may correct suboptimal rewards via e.g., back propagation algorithms in a perceptron).

In some embodiments, "semi-supervised machine learning" may refer to a process that combines techniques from supervised and unsupervised machine learning to address cases where a large amount of data is available but only a portion of the data is labeled. One approach is to impute or infer labels from similar data, based on a comparison of the data under consideration to other data within the database. Another approach is to generate labels for an unlabeled dataset based on the portion of data that is labeled. Yet another approach is to use training from a different problem or a different dataset to generate labels for these data. Such techniques are used to improve the learning accuracy of models by creating "pseudo labels" for the unknown labels (an approach known as transductive learning) and to improve model learning by adding in more input to output examples (inductive learning).

In some embodiments, "sensing array" refers to a configuration of sensors such as electrodes (for electrical signals), thermocouples (for thermal signals) or other types. This may also be referred to as sensing apparatus, recording probe, recording system and other terms which will be familiar to one familiar with the art.

In some embodiments, "supervised machine learning" may include methods of training of models with training data that are associated with labels. Techniques in supervised machine learning may include methods that can classify a series of related or seemingly unrelated inputs into one or more output classes. Output labels are typically used to train the learning models to the desired output, such as favorable patient outcomes, accurate therapy delivery sites and so on. Supervised learning may also include a technique known as 'transfer learning', where a pretrained machine learned model trained on one set of input or task, is retrained or fine-tuned to predict outcomes on another input or task.

In some embodiments, "unsupervised machine learning" may include methods of training of models with training data without the need for training labels (which are often obtained from experts, computationally, or crowd sourced). Techniques in unsupervised machine learning may include cluster analysis that may be used to identify internal links between data (regardless of whether data is labeled or unlabeled). In some embodiments, patterns (clusters) could be identified between clinical data (such as diagnosis of atrial fibrillation, or presence of heart failure, or other disease), family history, data from physical examinations (such as regularity of the pulse, low blood pressure), data from sensors (such as altered temperature, altered skin impedance), electrical data (atrial waveforms on the ECG), imaging data (enlarged left atrium or reduced), biomarkers, genetic and tissue data as available. Another technique is to use autoencoders, to featurize and compress input data. Autoencoders are sometimes described as 'self-supervised' since the model input and output are the same.

One branch of Machine learning (ML) is Deep Learning. In deep learning, Neural Network are used to develop the ML model. Neural Networks may be deep (more layers) or shallow (less layers) and may include convolutional layers, recurrent layers, dense layers, pooling layers, activation layers, or a combination of different layers. Neural networks are unique in that they can automatically extract relevant features from raw or minimally processed input data to map input data to output data (predicted data). Convolutional layers are particularly well suited to extract local spatial or time dependent features (from a specific part of the input) since they process local parts of the input one at a time. Convolutional layers can be 1D, 2D or 3D layers to process different input types. Dense (also known as fully connected) layers are particularly well suited to extract global features since the layer process the entire input. Dense layers are often placed towards the later layers of the model to predict the output of the model. Recurrent layers (e.g. LSTM, GRU) are a specific type of layers that are designed to extract temporal features since they keep a memory component of features from earlier (or later if bidirectional) parts of the input. In these feature extraction layers, the weights in the layers are adjusted such that the most relevant feature are extracted. The process of optimizing the weights is performed by minimizing loss functions that compare the predicted output with the true output. Different optimization techniques can be used to minimize the loss function, including but not limited to stochastic gradient descent, RMSprop, Adam, Adadelta, Adagrad, or Adamax. Other layers can be used such as activation layers (e.g. ReLU, Sigmoid, or others), pooling (max, average, or others), normalization, regularization (e.g. dropout), attention, reshaping, merging, and locally connected layers can be also be use separately or in combination.

Traditional Machine Learning, other types of artificial intelligence and statistical inference models can map inputs to outputs. However, they often require manual feature engineering to be used as the input, in addition to raw input data. While manual feature engineering can be seen as a disadvantage of traditional machine learning, it usually requires less data than neural networks—making it particularly useful for tasks with small or limited datasets. Traditional Machine Learning can be supervised, unsupervised, or semi-supervised learning. Traditional supervised Machine learning include different algorithms including Naïve Bayes classification, linear regression, K nearest neighbor, support vector machines, decision trees, and random forests. Naïve Bayes has the advantage of being fast because of the simplicity of the algorithm—making it well suited for getting quick results. Similarly, linear regression also has the advantage of being fast, but also provide an easy method to interpret the features that are most important using the trained model's coefficient. K nearest neighbor is a simple algorithm and can be used when similar data points are being grouped into k groups. Support Vector Machine (SVM) is a powerful algorithm especially when dealing with small datasets. This is because SVM only requires a few training examples to build the support vectors that perform the prediction. Random forests are non-parametric and ensemble methods that are based on decision trees, allowing prediction based on majority vote, which is often better than the prediction from a single model.

In some embodiments, the invention can use synthetic or computational data to train machine learning. Synthetic data refers to data which is generated by computational means, which can be derived from biological data, or entirely mathematical.

Synthetic or computational data can address one limitation of many machine learning applications: that they require large training data which are often difficult to obtain. For instance, it is difficult to obtain training data at the source of a biological rhythm disorder and away from the source of a biological rhythm disorder, particularly in different patients. In this case, large amounts of synthetic data can be generated of expected signals near a source, and expected signals away from a source. If the synthetic data is accurate, then the ML model can be effectively trained in this way. One limitation of synthetic data is that it may not allow the ML model to generalize during training, compared to true biological data. For this reason, synthetic data in the invention can be derived from large databases. For instance, synthetic data can be derived or modeled using data from the current patient at prior successful or unsuccessful procedures, or from patients with similar profiles (steps 115 or 1470).

In some embodiments, a "medical device" may refer to an instrument, apparatus, implement, machine, contrivance, implant, in vitro reagent, or another similar or related article, including a component part, or accessory, which is intended for use in the diagnosis of disease or other conditions, or in the cure, mitigation, treatment, or prevention of disease, in man or other animals.

In some embodiments, "neural networks" may refer to a class of machine learning models that include interconnected nodes that can be used to recognize patterns. Neural networks can be deep or shallow neural networks, convolutional neural networks, recurrent neural networks (gated recurrent units, GRUs, or long short term memory, LSTM, networks), generative adversarial networks, and auto-encoders neural networks. Artificial neural networks can be combined with heuristics, deterministic rules and detailed databases.

In some embodiments, "personal digital records" may include data related to health or disease of an individual. The personal digital records or personal clinical data may integrate several data streams which may or may not include cellular, genomic, proteomic, metabolomic or other data. The personal data may be stratified, partitioned or separated by desired groups, such as response to specific therapy, presence of a heart rhythm disorder, presence or seizure activity of the brain, good health or other attribute in that person. The personal digital record for an individual can be compared to a digital classification of data from a large group to identify individuals with 'similar' profiles. This comparison to similar profiles may be done mathematically and, once done, may enable predictions or selection of optimal therapy based on the successful response of those similar individuals. In some embodiments, the comparison may take the form of a mathematical 'best estimation' since all required data may not be available in the personal digital record of a given patient or in the digital classification.

Personal digital data enable personalized medicine in an individual. This is an alternative to the 'one size fits all' approach that commonly applies one therapy or approach to all patients of a subjective 'type'. Data elements used to create the personal digital record may represent the individual's health state, weighted by their likely contribution to the specific disease or index of health being considered. Personal digital records may be matched to a digital classification by algorithms that take into account the calculated or documented probability of the impact of each data type on health or disease. This may use deterministic algorithms or iterative processes including machine learning. For example, a personal digital record for heart rhythm may primarily consider heart rate and electrographic signals (surface ECG and intracardiac), and then consider heart function, prior history of heart rhythm issues, prior therapies, and so on. Greater mathematical weighting may be given to these data elements. Data from other organ systems can also then be included, and can enable a more comprehensive assessment and a closer match to other individuals in a digital classification. Such other data streams may include changes in breathing rate (e.g., lung sensors), changes in nerve firing rate (e.g., nerve function). Other data elements may include abnormal cardiac ejection fraction, location and presence of structural abnormalities of the heart. Historical data including age, gender, medication use, family history, laboratory values and genetic data can also be included in the personal digital record.

In some embodiments, "population data" may refer to a determinant of the accuracy of a process. This is to create a digital classification of patients in the population. The classification may include some or all data elements in the personal digital record of the individual under consideration. Mathematical analyses are used to compare the personal digital record of the individual to the digital classification and calculate the best match. If the index individual is very different from the reference population then the digital classification may not adequately represent this individual. In this case, data may be derived primarily from that individual, using prior data at times of adjudicated health or adjudicated illness. If the reference population is broad but has other limitations, such as not having sufficient data points for an accurate digital classification, or not having well-labeled data, the classification may be less useful. In some embodiments, the ideal data set may include data that are well labeled and from a large number of individuals that represent the entire population, which can be grouped by desired outcome to create a digital classification.

In some embodiments, "sensors" include devices that can detect biological signals from the body of an individual. A sensor may be in direct contact with the body or may be remote. When applied to a group of individuals, sensors may represent all or part of a defined population. Electromagnetic sensors can sense electromagnetic signals relating to the electromyogram (EMG), electroencephalogram (EEG), electrocardiogram (ECG), electrocardiographic imaging (ECGI), nerve firing, electromagnetic light (visible or invisible such as near infrared or infrared) or other emitters. In some cases, the term "sensor", especially when describing certain cardiac applications in which electrical information is detected, may be used interchangeably with "electrode", "electrode catheter", "probe" or "catheter." Electrical sensors can also detect bioimpedance, such as conductance across the skin that decreases in the presence of electrolyte solutions such as sweat when a person perspires, and that may occur during times of sympathetic nervous system predominance. Sensors can also detect other chemical changes via current flows. Sensors also include devices that detect temperatures, such as a thermistor or other thermal detector. Sensors can detect light such as changes in the color of reflected or emitted light from heart activity (photoplethysmography), changes in peripheral oxygenation (e.g., cyanosis, anemia, vasodilation on the skin). Sensors can detect sound via a microphone. This can be used to sense sounds from the heart, lungs or other organs. Sensors can detect contact force, pressure, or other vibrations or movement via piezoelectric elements. Sensors can detect chemicals directly, using specialized sensors for hormones, drugs, bacteria and other elements that are typically transduced on the device to an electrical signal. Examples include motion sensing of chest wall movement from a breath or heartbeat, chest wall vibrations from certain types of breath (e.g., a loud obstructive breathing sound) or heart sound (e.g., a so-called "thrill" in the medical literature). Breath sensors can detect movement of the chest wall, abdomen or other body parts associated with ventilation, or acoustic data (sound) associated with breaths, or oxygenation associated with breathing. Chemical sensors can detect chemical signals on the skin or other membranes that reflect body chemistry such as oxygenation and deoxygenation, acidosis (pH), stress (catecholamines), glucose levels, certain drugs or other states that will be familiar to those skilled in the biochemistry arts. Sensors can also detect images using a camera or lens requiring contact from the fingerprint or other body part, or sense movement from specific muscles, or sense iris dilation or oscillations from photosensors in a contact lens. Positional sensors can identify positions of body parts and changes over time (including gait) or contact sensing of the position of certain body parts at one point in time or over time (e.g., a facial droop, a facial tick or another idiosyncratic movement). In exemplary embodiments of the inventive system, multiple sensors may be used in communication with a central computing device or which may form a network linked via cable, BLUETOOTH, WI-FI, or other protocol to form an intranet or internet of things (IoT) of biological sensors.

In some embodiments, "sensors" can include information from non-invasive body surface potential mapping or even versions of the ECG to provide a 'global view' to complement to even replace intracardiac catheters inside the heart. Non-invasive body surface potential mapping is further described in U.S. Provisional Application No. 63/175,986 filed on Apr. 16, 2021. The relative sizes of these fields of view can be complementary, such as a global map from the body surface and a catheter inside the heart to provide a focused field of view at high spatial resolution. An application in an electronic device such as a smartphone, smart tablet, or smart device can help guide the user and record the necessary positions of the patches using its optical camera, Lidar sensor (infrared, ultraviolet, or other), or both (only location of electrodes will be recorded relative to anatomy, photos will not be saved or transmitted to the Cloud). Appropriate attached and location recording will ensure proper processing of data. Alternatively, the device might have a built-in indicator to ensure proper positioning and attachment of the device.

In some embodiments, "sensor element" refer to a sensor or portion of a sensor that can be independently addressed. Sensor elements may be arranged as arrays of multiple dimensions. A 1-dimensional array could take the form of a linear or curvilinear multi-electrode catheter. A 2-dimensional array could be a grid configuration. A 3-dimensional array could take the form of a sphere or ellipsoid. Other configurations will be self-evident to one skilled in the art.

In some embodiments, "signal" may include electronic, electromagnetic, digital or other information that can be sensed or acquired. Sensed signals are detected unaltered from their natural form (e.g., recorded) with no transformation. Sensed signals are typically biological signals. Sensed signals can be detected by humans (e.g., sound, visual, temperature) but also machines such as microphones, auditory recorders, cameras, thermometers. Acquired signals are detected in a transformed state, such as an ECG recording. Such signals may be biological, since cardiac bioelectricity generates the ECG, or non-biological signals, e.g., vibration sensed after application of sonic or ultrasonic energy, or a haptic signal transduced from a sensed electrical, sonic or another signal. Signals may be sensed via physical contact with a sensor.

In some embodiments, a "site of origin" of a heart rhythm disorder is defined as the first beat or beats (within the first 30 seconds, typically the first 5-10 beats) which initiate the heart rhythm from normal rhythm. For instance, AF often initiates by a small number of premature beats of the heart. If these beats arise from the pulmonary veins, ablation to isolate the pulmonary veins and eliminate these triggers may be effective. In another patient in whom many or most trigger beats do not arise from the pulmonary veins, PVI may not be effective.

In some embodiments, a "source" of a biological rhythm disorder (which can also be a critical region, or a region of interest) maintains the heart rhythm disorder once it has initiated. This can often be different from the site of origin. Source regions can be identified as patches of organized activity within chaotic disorders such as atrial fibrillation, or from which activation emanates in organized rhythms such as atrial tachycardia or ventricular tachycardia. Sources for the biological rhythm disorder may present several forms of expected pattern of activity. These may include rotational activity, partial rotational activity (partial circle or partial rotational circuit), focal activity, repetitive or repeating activity in other patterns, regions of irregular activity, activity associated with structural abnormality such as scar or fibrosis, or other patterns. For atrial fibrillation (AF), sources may be any of these patterns. In some biological rhythms, a series of sources may exist. The control system is capable of identifying and directing the operator to successive sources for AF. This can accelerate procedures and avoid treatment at less-critical regions that is time consuming, adds complexity, and may have adverse effects. In some embodiments, this device can identify important source regions for the rhythm disorder by quantifying their size or area, or by using other features such as rate or stability over time.

In some embodiments, "therapy element" refers to an independently addressable component to deliver therapy. In some embodiments, this may be an electrode to deliver ablation energy, a diode to deliver light or heat, a nozzle to deliver fluid including steam or irrigant or cooling fluid, an element to deliver proton therapy, or other therapy elements. Therapy elements may be arranged as arrays of multiple dimensions. A 1-dimensional array could take the form of a linear or curvilinear multi-electrode catheter. A 2-dimensional array could be a grid configuration. A 3-dimensional array could take the form of a sphere or ellipsoid. Other configurations will be self-evident to one skilled in the art.

The following description and accompanying figures provide examples of applications of the inventive system and method for personalizing treatment by analyzing personal digital records of health and disease, to detect regions of interest for biological rhythm disorders and treat such regions of interest. The examples described herein are intended to be illustrative only. As will be evident to those of skill in the art, additional variations and combinations may be formed employing the inventive principles disclosed herein.

Diagnostic and Treatment System

FIG. 1A illustrates a treatment system 100 for the operation of a heart treatment device 105, according to one or more embodiments. The treatment system 100 includes the heart treatment device 105, the control system 110, a data store 112, a generator 115, an irrigation pump 120, and an input/output device 125. The various components of the treatment system 100 are connected via a network 130. Additional or fewer components may be implemented in the treatment system 100. For example, another non-invasive device comprising a wearable electrode array can be utilized in conjunction with the other components shown in FIG. 1.

The heart treatment device 105 is used for invasive access and treatment of heart rhythm disorders. The heart treatment device 105 includes, among other components, a handle 145, a shaft 150, and a catheter 155. The handle 145 is where a physician or automated control system controls movement of the shaft 150 and the catheter 155. The handle 145 also includes interfaces for connection to other components in the treatment system 100, e.g., the generator 115, the irrigation pump 120, and the network 130. The shaft 150 is inserted into a patient via a vascular access point and often through a guiding sheath. The shaft 150 is directed to the tissue requiring treatment. In one embodiment, the shaft is deflectable to steer to required tissue. The catheter 155 is deployed from the shaft 150. The catheter 155 is configured to sense electrical signals from sensing elements 160, which enable software in the control system 110 to enable guidance of the catheter, and then to deliver ablation energy from ablating elements 162 to one or more source regions identified in the tissue. The various components of the heart treatment device 105 will be further described in FIGS. 2-10.

Prior to insertion into the patient, the catheter 155 is sheathed within the shaft 150. The shaft 150 is inserted into the patient via a vascular access device, such as an introducing sheath, and directed to the heart tissue with the catheter 155 in a compact state. Upon reaching the heart tissue, the catheter 155 is unsheathed, transitioning from the compact state to an expanded state as shown in FIG. 1. In the expanded state, the catheter 155 can be moved by steering of the shaft 150. The handle 145 provides ability to (1) control transitioning of the catheter 155 between the compact state and the expanded state and (2) control movement of the catheter 155.

Collapse of the catheter within an introducer sheath should be smooth without undue force. It also should not inadvertently trap tissue as it is pulled into the sheath. The closed design of the electrode array catheter in many embodiments prevents such events. Catheter shapes in other embodiments may include the ability to deliberately 'attach' to structures for stability, such as for ablation of the papillary muscles which is typically limited by catheter slippage.

Tailoring of depth and breadth (width) of view 164 is achieved by altering sensing or ablating element configuration, namely a single element or specified combinations, as well as filter settings and power delivery. Similarly, ablating elements can be tailored to provide greater depth of ablation (such as higher power for shorter durations) or greater depth (such as modest power for longer durations) as deemed appropriate for the specific biological rhythm, thickness of tissue, and patient. Tailoring the depth and/or breadth of view is further described in FIG. 5.

Figure 1B:
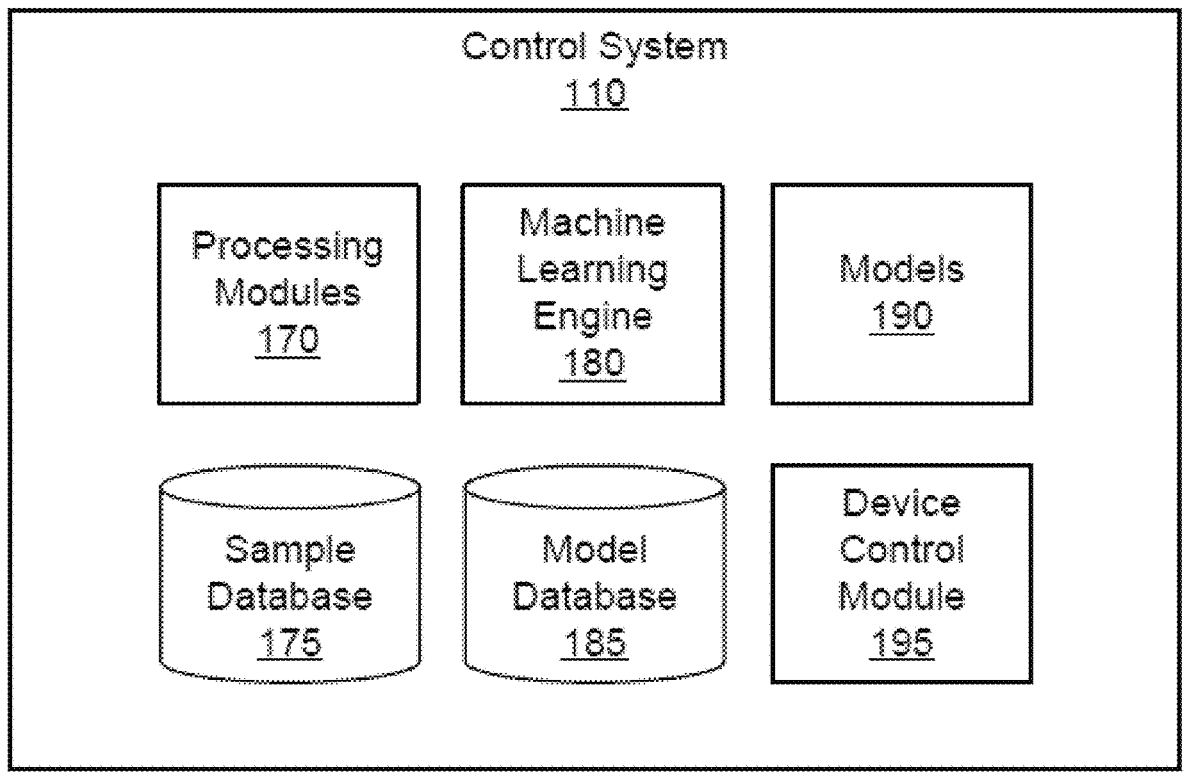
FIG. 1B is an example architecture of the control system, in accordance with one or more embodiments.

The control system 110 controls the various components of the treatment system 100. The control system 110, further described in FIG. 1B, is configured to receive data from the various components and provide instructions to the various components. For example, the control system 110 receives electrical signals sensed by the heart treatment device 105. The control system 110 may process and analyze the electrical signals to determine guidance controls for the heart treatment device 105. The control system 110 may provide the guidance controls for movement of the catheter 155 when deployed and in contact with the patient's heart. The control system 110 may further determine an optimal ablation procedure upon identifying the location of a source region in the patient's heart that is a contributor to the heart rhythm disorder. The control system 110 may provide instructions for carrying out the ablation procedure to the generator 115, the irrigation pump 120, and the heart treatment device 105. The control system 110 may also receive inputs from a user, e.g., a physician, to aid in the treatment procedure. The control system 110 may also provide real-time data and/or updates to the input/output device 125 for displaying such data and/or updates during the treatment procedure.

The data store 112 stores all the various data of the control system 110. The data store 112 may be one or more computing devices that include memories or other storage media for data related to the patients, e.g., in patient profiles such as data measured by the heart treatment device 105. Some of the data may take the form of personal digital records. The data may be routed by the control system 110. The data store 112 may be a network-based storage server (e.g., a cloud server). The data store 112 may be part of the computing server or may be a third-party storage system such as AMAZON AWS, AMAZON S3, DROPBOX, RACKSPACE CLOUD FILES, AZURE BLOB STORAGE, GOOGLE CLOUD STORAGE or ENGINE, etc.

The generator 115 provides electrical energy to the heart treatment device 105 for performing an ablation procedure. The generator 115 may comprise an energy source 135 and an interposer 140. The energy source 135 generates the electrical energy for use in the ablation procedure. The energy source 135 may in turn fetch the electrical energy from another energy source (e.g., an electrical outlet, an electricity generator, a battery, etc.) for conversion into the electrical energy for use in the ablation procedure. For example, the ablation procedure may require a particular energy frequency, a particular waveform, a particular duration, or other ablation procedure parameters. The energy source 135 can generate electrical energy at the appropriate frequency, with the appropriate waveform, and for the appropriate duration. The interposer 140 electrically connects the energy source 135 to the electrode array on the catheter 155. The interposer 140 controls connection to each electrode of the electrode array. For example, if the ablation procedure requires actuation of a subset of the electrodes in the electrode array, then the interposer 140 may switch off connections for the remaining electrodes not required during the ablation procedure. As another example, the interposer 140 may control which mode each electrode is operating in. As described above, the electrode array of the catheter 155 is advantageous in that each element or subsets of elements may be used for sensing and therapy. The interposer 140 may utilize switches connected to each sensing element, for switching between a sensing mode, an ablation mode, and an off mode (e.g., the electrode being connected to an electrical ground). As yet another example, the interposer 140 enables even a simple basic generator 135 to control subsets of electrodes, deliver different frequencies and power parameters.

The irrigation pump 120 controls pumping of irrigant to the heart treatment device 105. The irrigation pump 120 may include various vessels and fluid channels for directing stored irrigant to the heart treatment device 105. The types of irrigant that may be used include: a chemical buffer or a saline infusate. Delivery of irrigant during an ablation procedure prevents overheating of the heart tissue and the catheter 155, which avoids scarring of the heart tissue and potential damage to the catheter 155. Prevention of overheating also allows for deeper energy delivery without needing to prematurely stop the ablation procedure, providing greater efficacy in the ablation procedure. In some embodiments, half normal saline or other variants can be used; half-normal saline can improve depth of ablation for the same power delivery at the risk of higher temperature rise. These considerations can be balanced when tailoring the system for a specific biological rhythm disorder, organ chamber and patient.

The input/output device 125 is configured to display visual data to a user of the heart treatment device 105, e.g., a physician. The input/output device 125 may be a touch display capable of receiving user inputs. In such embodiments, the input/output device 125 may present a graphical user interface that a user is capable of interacting with. The user can provide inputs to the control system 110, e.g., inputs for adjusting operation of the various components. Example controls include steering of the heart treatment device 105 whilst in the patient, deploying and/or retracting the catheter of the heart treatment device 105 whilst in the patient, controlling a start of an ablation procedure, toggling parameters for the generator 115, toggling parameters of the irrigation pump 120, among other operations described herein this disclosure. The input/output device 125 can provide a real-time mapping of the patient's heart tissue as sensed by the electrode array of the heart treatment device 105. Upon identification of one or more source regions, the control system 110 may alert the physician via the input/output device 125. The input/output device 125 may provide further updates during treatment, e.g., during the ablation procedure.

The network 130 provides connections to the components of the treatment system 100 through one or more sub-networks, which may include any combination of local area and/or wide area networks, using both wired and/or wireless communication systems. In some embodiments, a network 130 uses standard communications technologies and/or protocols. For example, a network 130 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), and so on. Examples of network protocols used for communicating via the network 130 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 130 may be represented using any suitable format, such as hypertext markup language (HTML), extensible markup language (XML), or JSON. In some embodiments, all or some of the communication links of a network 130 may be encrypted using any suitable technique or techniques such as secure sockets layer (SSL), transport layer security (TLS), virtual private networks (VPNs), Internet Protocol security (IPsec), etc. The network 130 also includes links and packet switching networks such as the Internet.

Control System Overview

FIG. 1B is an example architecture of the control system 110, in accordance with one or more embodiments. The control system 110 may include one or more computing devices to control the components of the treatment system 100. The control system 110 utilizes one or more processing modules 170 and/or models 190 for performing the various analyses, e.g., that may dictate control of the components. The control system 110 comprises, among other components, one or more processing modules 170, a sample database 175, a machine learning engine 180, one or more models 190, and a model database.

The processing modules 170 process the data received by the control system 110. In one or more embodiments, the processing modules 170 may perform some processes to standardize data received from disparate components. Other processes may include, but are not limited to, denoising, partitioning, tagging, labeling, embedding, etc. Example processing modules include signal processing modules that may process the electrical signals measured by the heart treatment device 105.

The sample database 175 stores samples and/or other data that may be used by the control system 110. For example, the sample database 175 stores training samples of electrical signals measured by various sensing arrays (e.g., a catheter of a heart treatment device, an EKG machine, a body-surface sensing array, etc.). The training samples may be used to train one or more of the models 190. The sample database 175 may further cache outputs by one or more of the models 190, e.g., for use in tuning or updating the models 190.

The machine learning engine 180 performs one or more machine learning algorithms to train one or more of the models 190 and/or one or more of the processing modules 170. As such, one or more of the models 190 and/or one or more of the processing modules 170 may be machine-learned models. Generally, machine learning is a manner of training a model with training data to make predictions or decisions on new data. Generally, supervised learning utilizes training data with known or assigned labels, wherein the model is trained to predict the label of an unseen test sample. Unsupervised learning generally learns patterns from training data without a label. Other types of learning include reinforcement learning which utilizes an objective function that guides training of the model or semi-supervised learning where a subset of the training data is labeled.

The one or more models 190 analyze data received by the control system 110. The models 190 may be trained by the machine learning engine 180 with sets of training samples. Generally, the models 190 receive one or more inputs and provide an output based on a trained function and learned weights. Example models 190 include a catheter optimization model, a signal reconstruction model, a personalization model, a featurization model, a guidance model, a therapy model, etc. The catheter optimization model may input information of an individual to determine an optimal catheter design for use in the heart treatment device 105. The signal reconstruction model may input electrical signals detected or measured by a sensing array (e.g., on the catheter of the heart treatment device 105) to recreate or reconstruct true electrophysiological signals. The personalization model may input information of the individual to determine personalized treatment procedure for the individual. The featurization model may input recorded signals by a sensing array (e.g., electrophysiological signals) to determine features of the signals (e.g., a spatial map, spatial features, spectral features, etc.). The guidance model may input signals recorded by a catheter (and may further input other features derived by the featurization model) to determine (1) whether the catheter is located at a critical region and/or (2) a guidance direction for movement of the catheter towards the critical region. When the guidance model determines the catheter to be located at the critical region, the guidance model may further output information relating to the critical region. For example, information may include a type of critical region, a size and/or shape of the critical region, a strength of the critical region, etc. The guidance direction comprises at least a direction towards the critical region, and may also comprise a predicted distance of the critical region from a current location of the catheter. The guidance direction may be presented to a physician operating the heart treatment device 105. In embodiments with an automated heart treatment device 105, the device control module 195 may control movement of the heart treatment device 105.

The model database 185 stores model data relating to the models 190. The model data may include one or more functions for each model, one or more weights of the functions, one or more parameters of the model, one or more informative features of inputs, other information relating to the models, or some combination thereof. The model database 185 may further store architecture of the models 190, e.g., in context of a neural network: number of layers, nodes per layer, connections between layers, etc.

The device control module 195 determines control instructions for movement of the heart treatment device 105. In one or more embodiments, the control system 110 controls the heart treatment device 105. The control system 110 may control movement of the heart treatment device 105, sheathing and/or unsheathing of the catheter, sensing of electrical signals by the sensing array of the catheter, performing an ablation procedure by one or more ablating elements. In response to analyses performed by the models 190, the device control module 195 may generate control instructions that are provided to the heart treatment device 105 for automated operation. For example, in response to the guidance model providing a guidance direction towards a critical region, the device control module 195 may generate control instructions to move the heart treatment device 105 according to the guidance direction. As another example, in response to determining (e.g., by the guidance model) that the catheter is located at the critical region, the device control module 195 may generate control instructions to the perform the ablation procedure.

In various embodiments, the control system 110 may be a server computer that includes software and one or more processors to execute code instructions to perform various processes described herein. The control system 110 may also be a pool of computing devices that may be located at the same geographical location (e.g., a server room) or be distributed geographically (e.g., cloud computing, distributed computing, or in a virtual server network).

FIG. 2 illustrates an overall operation of the control system, in accordance with one or more embodiments. In particular FIG. 2 provides detail of mapping, diagnosis, directional guidance and therapy from the control system 110.

In some embodiments, catheter optimization 200 can be performed to determine optimal specifications for a catheter 155 to treat a given patient for a specific biological rhythm in a determined organ region. Catheter optimization can analyze data associated with the patient to determine optimal specifications for the catheter 155. For example, based on the electrical signals measured for a patient (e.g., by an electrode array of the heart treatment device 105 or another non-invasive sensing device), the catheter optimization step can determine an optimally sized catheter having an electrode array with a particular arrangement and a particular resolution. Catheter optimization 200 may be one of the models 190. Some or all of the other data described herein this disclosure can be considered in a model to determine the optimal specifications. In some embodiments, the model comprises a plurality of decision trees to determine the optimal specifications. In other embodiments, the model is a machine learned model. A catheter 155 may be specially manufactured according to the optimal specifications. In other embodiments, a catheter 155 may be selected from a set of manufactured catheters, each having unique specifications, wherein the selected catheter 155 has specifications that closely match to the optimal specifications determined. A physician implements the selected catheter 155 for use in the heart treatment device 105.

Step 205 records signals from the device in unfiltered mode. Typical settings for electrical recordings in the heart are 1 kHz sampling frequency, with signals bandpassed at 0.05 Hz to 500 Hz. A notch filter can be used to reduce AC electrical noise (50-60 Hz). Signals can be recorded continuously or for periods typically of minutes, and then transferred to the invention for further analysis.

Step 210 introduces programmable settings for sensing (element 180 in FIG. 1). Sensing elements can provide greater depth by keeping low frequency components, and can record nearer tissue by introducing a high-pass filter. High-pass filtering to remove far-field signals is typically in the range >20 Hz. Unipolar sensing is deeper and has wider field than bipolar sensing. As the spacing between electrodes in a bipole increases, the width of tissue recorded increases at the expense of missing (subtracting) small localized signals along the path of the bipolar electrodes. These settings can be programmed by the operator, with suggested guidance from the inventive system, within the physical limits of the selected probe. In some embodiments, step 210 and step 205 are interchanged so that filter selection and sensing are configured prior to recording. These steps are further detailed in FIG. 3.

In several embodiments, machine learning techniques are used at separate components of the invention. One component is the reconstruction of physiology (or action potentials) 220. Another component is 230, creation of a "landscape" of features. Other components of the invention in which machine learning can be applied, depending on the embodiment, are identification of features of a biological rhythm disorder 250, identification if a sensing probe (e.g. catheter) is located near a desired feature 270, determining a navigational guidance 290, determining of an endpoint is achieved (e.g. after therapy at a location in the biological organ) 285, determination of whether to repeat the process 295. Other areas in which machine learning can be applied to components of the invention will be familiar to one skilled in the art.

Reconstruction of physiology 220 (reconstruction of action potentials) from recorded catheter signals in patients is a critical step in some embodiments. Tissue physiology as recorded from single cells, or directly from tissue such as in animals when sick, often use tools that cannot be applied in human patients. Catheters applied in the clinic produce signals which are surrogates of direct tissue recordings, which may differ considerably from true tissue signals. For instance, clinical catheter signals in atrial fibrillation (AF) or in the brain from electroencephalography look very different from tissue signals (action potentials) and are often very difficult to interpret. This causes difficulty in interpretation and inaccurate therapy. Step 220 uses several data elements and analytical steps to reconstruct tissue signals to improve all elements of the invention. Reconstruction of physiology 220 may be one of the models 190. A reconstruction model is further described in FIGS. 7-12.

Construction of a spatial map 230 from reconstructed signals from the catheter array, also termed a "landscape" analysis of the biological rhythm, enables more precise diagnosis of the rhythm in that patient and identification of the sites to target for therapy by ablation. A landscape may comprise various types of spatial or temporal feature as outlined in item 240. These features can be represented in maps of the biological rhythm, or landscape analyses, or landscape maps, of which several types exist as illustrated later (FIG. 14). In some embodiments, identification of landscape features in 230 is performed by machine learning, rule based systems, or other computational approaches. Construction of the spatial map may be accomplished by a featurization model, which may be one of the models 190.

Feature selection 240 in the landscape enables identification of critical regions, regions of interest or sources, which vary between different biological rhythm disorders for different organ systems. This can be selected by the operator from a range 250, which is intended to be illustrative and not exhaustive of all features which can be identified by the invention.

Features 250 can be electrical, structural or other. Each feature detected in this patient may indicate a target that is likely to be successful, or a target that is likely to be unsuccessful and which should be avoided for therapy. Examples of targets which may be unsuccessful include targets which were treated at a prior yet unsuccessful procedure, those which have been unsuccessful targets in other patients with similar profiles to this patient or other combinations that will be familiar to one skilled in the art.

Electrical features 250 include but are not limited to focal activity (with centrifugal spread of activation from a small region), rotational or reentrant activity that is complete (one or more full rotations) or incomplete (less than a full rotation), rapid activity, complex signal shapes, repeating patterns of signals or evidence of conduction slowing (which can be associated with regions where rotational or reentrant activity can form). Structural feature include evidence of low voltage (indicating scar or ablated tissue), intermittent low voltage (suggesting gaps in scar or ablated lesion sets), or borderline voltage adjacent to scar or ablated tissue. Other features include a feature of biological rhythm bar codes, based on the onset and offset of tissue physiology reconstructed by the invention and illustrated in FIG. 14. Some other features are also illustrated in FIG. 14. Identification of the features may be accomplished by a featurization model, which may be one of the models 190.

Customizable user-definable targets 250 are a feature in some embodiments. providing the ability to identify and track features that are considered important to this patient by the operator (user, physician, scientist). User-definable features are akin to programmable 'soft keys' on a computer or programmable device, and represent a logical 'object' for one or more feature(s) for the rhythm disorder that can be mapped and tracked by the invention in that patient. User definable rhythm patterns can be based on operator experience, and can extend beyond those available in generic commercial systems. Patterns can be suggested by the invention using machine learning of that patient's data compared to stored data ('AI-suggested' in item 250). Stored data can be derived from this patient at a prior procedure, another patient with a similar profile determined by techniques such as machine learning, or from a library of patterns in a population of patients. For instance, in a patient with a previously successful and remote procedure, feature(s) treated at that time could be re-treated. This may include gaps in pulmonary vein isolation lines or driver sites, or sites of complex fractionated electrogram in a patient with AF. Conversely, in a patient with a prior procedure that was unsuccessful, for instance with early post-procedural recurrence, these or other features treated at that time may not be relevant to this patient and the operator may choose to avoid them at this procedure. Features may also be obtained from computer generated library of theoretical patterns, such as those predicted to represent slow conduction at a critical site maintaining the arrhythmia, or those arising close to a driver region.

User-definable features 250 are also shown in FIG. 14 (elements 1460-1470) and can be input by a user or downloaded from a database. User input may use specific devices, such as a dedicated console, or a consumer device such as a tablet or smartphone, or speech recognition or eye movements in a virtual reality or augmented reality headset. Downloaded features provide the ability for the invention to be updated with newly identified features in the clinical or scientific literature, or newly identified features by machine learning from a database, or other advances over time.

Step 270 compares if signals at the current recording site matches to being present at a critical region (e.g., to be treated). If the comparison is positive, instructions may be provided to the physician to treat at this location 290. If the comparison is negative, then directional guidance may be provided 290 towards or away from a specified feature pattern. Directional guidance by a guidance model (which may be one of the models 190) is detailed further in FIGS. 15 and 16. In some embodiments, step 270 is performed by machine learning, rule based systems, or other computational approaches.

At step 295, some or all of these steps are repeated. Depending on the physician preference and stage of a procedure, this may involve repeating the comparison steps 270-295. Alternatively, this may also involve steps from re-recording 205-210, re-optimizing signals 210-220 and/or redefining features 230-250.

Endpoint analysis 285 is the next operation in some embodiments if therapy is delivered 280. Endpoint analysis is used to determine the efficacy of therapy such as ablation, and some precise components are detailed in FIG. 15. Here, some elements of endpoint analysis are outlined. If a feature is treated such as by ablation, it may or may not remain present at this location. First, if the feature is still present, several options exist for the treating physician. Therapy may have been ineffective, in which case therapy may need to be repeated using this or another device. Alternatively, it may not be possible to eliminate this feature by therapy at this location. This may occur if less aggressive therapy is required at this location, such as sensitive regions in the heart (e.g. the atrioventricular node or sinus node) or in adjacent structures (e.g. the esophagus or phrenic nerve). A third possibility is that the feature is a false-positive detection. In cases, when the feature is still present, subsequent navigational guidance in some embodiments can take this into account and provide guidance to alternative or secondary sites away from the present location. Second, if endpoint analysis 285 shows that the feature is no longer present after ablation, different options exist. The physician may choose to apply therapy to this and neighboring locations to consolidate therapy in this anatomical region. This will depend upon the perceived safety and efficacy of applying more therapy to a successfully ablated site. Alternatively a different feature may now be present at this location. This may include scar (very low voltage from tissue elimination) or edema (attenuated voltage due to insulation of tissue from catheter by fluid) due to ablation. This may also include rotational activity, which may arise in patients with AF after ablation of a site of focal activity, or of complex fractionated activity, or that leaves a small gap (absence of scar). Upon detection of this feature, the operator may elect to ablate at this location, or repeat steps 240 to 285 before making this determination, or the physician may wish to repeat 295 from earlier steps. In some embodiments, endpoint determination is performed by machine learning, rule based systems or other computational approaches.

Endpoints will differ for each type of critical region in the arrhythmia landscape. For macro-reentrant activity, such as in atrial tachycardia or ventricular tachycardia, the ideal endpoint is complete elimination of reentry. For localized reentry in AF, one endpoint is reduction of rotational activity to absence of reentry, partial reentry, conduction block or other. For focal activity, in atrial tachycardia or ventricular tachycardia, one endpoint is complete elimination of focal activity. For focal activity in AF, one endpoint is a reduction of consistent focal activity from a circumscribed localized region. For focal activity in AF, one endpoint is heart rate slowing of the focal activation. For features of scar or gap, one endpoint is to completely homogenize scar, i.e. leave no gaps (i.e. no residual viable tissue). An alternative endpoint is to encircle viable tissue with scar, such as for pulmonary veins for AF, or to isolate regions that cannot be completely ablated for safety concerns. For the feature of complex signals in AF, one endpoint is complete elimination of signals; another is regularization of signals into less complex shapes such as passing waves or other; another is the absence of diastolic electrical activity. For the feature of repeating patterns in AF, one endpoint is elimination of consistent repetitive activity. For the feature of ganglionated plexus sites, several endpoints include loss of high frequency activity, loss of fractionated signals, heart rate slowing when therapy (ablation) is delivered that reflects a vagal effect, and attenuation of heart rate variability after ablation. This list is not intended to be exhaustive, and other endpoints will be self-evident to one skilled in the art.

Once the physician is satisfied that an endpoint has been achieved at this spatial location, they may choose to continue the procedure at other locations which includes repeating steps 295. Alternatively, the physician may choose to stop the procedure (step 298).

In one embodiment, each endpoint determination at step 285 made by the treating physician (or user, operator or entire treatment team). Software logic is provided in the invention to assist the physician in this determination, as discussed in FIG. 16, FIG. 17. In another embodiment, the endpoint determination is made automatically by the software logic such as machine learning, rule based systems or other computational approaches, with oversight by the treating professional.

Catheter Optimization

FIG. 3 provides detail on catheter optimization, programmable field and depth of view. Catheter optimization may be one of the models 190. Step 300 reads the sensor size and configuration for a probe. Element 310 shows two sample embodiments of probe configurations which further detail design elements in 155 (FIG. 1). In embodiments for the heart, typical sensor or electrode dimensions are 0.1-5 millimeter (mm) in length and width. Dimensions may be symmetrical, similar or different in length and width. Spacing between these sensors (e.g. electrodes) can vary. A typical range is 0.5-5 mm between electrodes. Shorter inter-electrode spacing may provide greater spatial resolution for more accurate sensing, although larger sized electrodes have a wider sensing antenna is wider and may overlap in sensing if they have a small inter-electrode spacing. Wider spacing can be used, but may miss small features such as gaps and may not provide accurate spatial targeting of features for ablation. These points are further detailed in FIG. 4. Based on these sizes and spacings, typical overall dimensions of a 2 dimensional catheter in the shape of a spade are in the range of 10 mm to 50 mm (1 to 5 cm) on axis, which could be in a rectangular, square, oval or other shape. A three dimensional cube or spherical catheter will thus be 10 mm to 50 mm (1 to 5 cm) in each of its three axes.

Step 330 calculates bipolar signals from unipolar recordings. Several bipolar pairs can be chosen depending on the physical configuration of the catheter. A catheter can thus be selected to optimize the desired electrode configuration and bipolar spacing. Step 340 then interprets (parses) the differences between unipolar and bipolar recordings, which can be useful for different biological rhythm disorders. Step 350 interprets (parses) differences between filter settings for these unipolar or bipolar electrode configurations. Typical filter settings are original recordings in wide-open settings (0.05-500 Hz), settings to minimize baseline noise (1-500 Hz), settings to reduce AC current noise (notch filter at 50-60 Hz), and settings to emphasize close-by ('near-field') signals (30-250 Hz). Other filter settings that can hone in on the true signal may be used. Step 360 uses transfer functions described below to these signal types.

Feature logic 370 can be applied to guide diagnosis and directionality (steps 220 onwards in FIG. 2). If a feature is present in near field recordings (i.e. close-by), it is likely close by the catheter. Near field recordings can often be obtained by filtering at 30-250 Hz. Said feature is likely to have larger spatial size if it is also seen on 'far-field' recordings, such as those filtered at a lower high-pass threshold (for instance, 0.05-250 Hz). Said feature is likely to be smaller if not present on far-field recordings. Conversely, if a feature is not present in near-field recordings but present in far-field recordings, it is not at the current sensing position. Its position may be indicated by a directionality guidance functionality. If a feature is neither present in near-field recordings nor in far-field recordings, then this feature is not currently detected and other aspects of directional guidance can be used to move the catheter, such as probability estimates of the location of a critical region by machine learning.

Step 380 optimizes the catheter for the biological rhythm disorder in the patient being treated. In one embodiment of the invention, optimization involves selecting one or more hardware catheters with one or more appropriate configurations. In another embodiment of the invention, optimization is performed in software and involves tailoring analysis to use specific electrodes or ignore specific electrodes in the hardware array to optimally map this biological rhythm.

FIG. 4 illustrates the impact of electrode configurations on field (width) of view. Mathematical simulations were applied to wavefronts detected by electrodes of 0.1 mm, 0.2 mm, 0.5 mm, 1 mm and 2 mm long, each separated by 3 mm (center-to-center) to the adjacent electrode (step 410). Experiments 420 examined the field of view for unipolar electrodes of each length (width 0.8 mm). The sensed field that recorded >30% of maximum signal (coded red) increased from diameter ~2 mm to diameter ~4 mm for progressively larger unipoles. Experiments 440 summarize the percentage of area covered and percentage of area overlap from 0.1 to 1 mm unipoles spaced at 3-5 mm uniformly across a square mapped field from each corner to each corner. As seen, >60% of mapped area is covered for 3 and 4 mm spacing. Overlap is essentially zero for many electrode configurations. These results can be used to customize catheter selection for desired rhythms. For rhythms such as AF where nearby sites may exhibit different electrical patterns, minimizing overlap and maximizing coverage is important and 3-4 mm spacing may be ideal while still keeping good overall coverage. Experiments 430 examined the field of view for bipolar electrodes of this same size, spaced at 3 to 5 mm with the same color scale. The sensed field recording >30% of maximum signal was peanut shaped and enlarged minimally from ~1×4 mm to ~2×4 mm for larger electrodes. Experiments 450 showed that bipolar combinations with electrodes spaced at 3-5 mm all showed ~100% coverage but with high overlap and may not be ideal for mapping AF. They may be advantageous for mapping organized rhythms with one predominant wavefront (spatially coherent) such as atrial flutter or tachycardia. The Control system of the invention is optimized from these data to suggest an optimal electrode configuration for the preferred catheter in each patient based on the type of biological rhythm disorder.

FIG. 5 examines the impact of electrode configuration and contact (height off tissue) on depth of view. This is shown for the embodiment of an electrode of diameter 0.8 mm, length 1 mm. Panel 510 shows the depth of field in a unipolar configuration, in which the electrode is compared to an indifferent remote electrode (typically the Wilson Central Terminal). The figure shows that width and depth of field are widest for catheters 10 mm off the surface with a depth of >3 mm, and in one embodiment would represent endocardium and epicardium of the atrium equally. At an electrode height off the tissue of 0.5-1 mm, sensing width is 5.5-8 mm, and depth is 2.3-2.7 mm. Pushing the electrode against tissue for very good contact (<0.1 mm off tissue), the field is ~3 mm wide and ~1 mm deep (i.e. only the opposed surface, such as the endocardium). Panel 520 shows depth of field for a bipolar configuration with 2 mm center-to-center spacing. As electrodes are 10 mm off tissue, the depth of sensing is >3 mm deep, which drops to ~1 mm deep as soon as electrodes are near tissue (~1 mm or less off tissue). Fields of view are narrower than for unipolar sensing as shown before. These results can be used to customize catheter selection for desired rhythms. In rhythms such as AF where endocardial and epicardial tissue may exhibit different electrical patterns, catheter and electrode design can be programmed to examine diagnose signal patterns in the endocardium or epicardium.

Heart Treatment Device

FIG. 6 provides an overview of the treatment aspect of the invention. This comprises a catheter as indicated in FIG. 1 items 105-165 with a handle, shaft, a distal catheter end 155, electrodes for sensing 160 and for ablation 162. In one embodiment, it comprises at least one electrode that can both sense electrical signals and ablate tissue, or at least two electrodes, where one can sense electrical signals and one can ablate tissue. Other embodiments comprise a combination of electrodes that can sense electrical signals, electrodes that can ablate tissue, or electrodes that can do both. In a preferred embodiment, the distal end or housing includes an electrode array to sense spatial patterns of signals and ablate spatial regions. As an example, the distal end or housing may be configured as a plurality of splines on which an electrode array is disposed. The electrode array comprises a plurality of electrodes, wherein each electrode can be configured to sense electrical signals and to deliver ablation energy to tissue. The bends of the splines 630 store energy when the catheter 610 is in a compact state, i.e., the catheter 610 is sheathed. As the catheter 610 is deployed, i.e., extended beyond the sheath, the stored energy is released causing the splines 630 to expand and to space apart in the expanded state. The catheter is further described in U.S. Provisional Application No. 63/231,669 filed on Aug. 10, 2021

The dual functionality of the electrode array coupled with appropriate logic or software simplifies the treatment process and makes it more efficient, as the same catheter can be used for both sensing the presence of important spatial patterns, or to guide the catheter towards a critical or source region based on sensed electrical signals, and then to deliver patterns of ablation energy to treat the biological rhythm disorder using all electrodes or subsets of electrodes from the same catheter.

In one or more embodiments, the catheter includes a plurality of connector struts 635 attached to the splines. The connector struts 635 are composed of a substantially rigid yet deformable material with one or more engineered bends that can store compressive energy. When the splines are retracted into a sheath, the splines collapse in proximity to one another. Collapsing the splines deforms the connector struts 635 so that the splines oppose geometrically in the sheath without the need for undue force, thereby storing compressive energy in the bends. When the linear splines are subsequently extended from the sheath, the compressive energy stored in the connector struts 635 are released, returning them to their relaxed state where the splines are spaced apart from one another for optimal sensing and ablation energy delivery. The implementation of connector struts 635 provides a creative solution for easy expansion and collapse of the catheter from the sheath.

In one or more embodiments, the catheter includes a plurality of irrigation pores that may be interlaced within the electrode array. The irrigation pores provide controlled irrigation during ablation by the catheter. Irrigation while ablating tissue prevents charring of tissue from the ablation, and enables ablation energy to penetrate deeper into tissue.

In one or more embodiments, a method is disclosed for optimizing the electrode (sensing element) array in FIG. 6 for a particular patient as indicated in FIG. 3.

The area covered by the electrode array will vary with the organ being treated. The size may be smaller for a device in the brain, where small size is at a premium to avoid destruction of tissue, than for a device in the heart, where larger mapping and ablation areas are sometimes needed. The therapy tool contacts the organ by conforming to its surface at a plurality of locations. Note that sub-regions can be sensed (i.e. 'sensing regions') within the overall area covered, and sub-regions can be treated (i.e. 'therapy region') within the overall covered region. This selection can be tailored to each individual and to the biological rhythm.

As shown in FIG. 6, the array may be a substantially rectangular array defined by a repeating rectangular grid with dimensions α×β, wherein a is the dimension perpendicular to the center axis 610 and β is the dimension parallel to the center axis, and wherein an electrode is placed at each vertex of the rectangular pattern. As a numerical example, this catheter illustrates a total of twenty-five electrodes in the array, with five electrodes on each of five splines, with rectangular grid dimensions: a is 2 mm and β is 2 mm.

The range of sensing elements (e.g. electrodes) for embodiments for heart rhythm applications within the heart is typically 4 to 128. In the embodiment in FIG. 6, the mapping electrode array (or 'waffle', or 'spade', or 'grid') is configured as a 2-dimensional array with dimensions of about 1.5 cm along each axis (W×L 1.5 cm×1.5 cm). The array does not have to be square, and could be rectangular or have multiple shapes. A typical useable size range for mapping heart rhythms would be 1 cm×1 cm (1 $cm^2$ area) at the small end to 5 cm×5 cm (25 $cm^2$) at the larger end. An electrode density may be at least 2-by-2 sensing elements in each area of 25 $mm^2$.

The small end of the size range is defined by the need of that patient and their biological rhythm disorder. The diameter of organized rotational domain for drivers of AF is typically ~5-20 mm. Identifying vectorial patterns or repeating electrogram patterns in AF may require a spatial mapping array of 10 mm or more diameter, to identify larger-scale organization without only seeing small-scale variations that are typical of fibrillation. Gaps in ablation lines or pulmonary vein isolation lesion sets are typically on the order of 2-5 mm. The array should be large enough to span a gap and define their boundary, so that the array should ideally also record from either side of a gap. Smaller arrays therefore may not cover sufficient tissue to map important patterns.

Larger arrays have the problem of spatial resolution and may be unwieldy to place. The electronics for all sensing elements must fit within the catheter shaft 150, which in many embodiments will be inserted through a blood vessel. This limits the size of the shaft and hence the number of electrodes (sensing elements) that can be supported. Thus, a larger electrode array will typically result in a lower spatial density of electrodes. This must be tailored to the rhythm being considered. Larger 2D arrays may also not oppose (sit) well along curvilinear surfaces of biological organs, and may require 3D configurations such as basket or ellipsoid shapes.

In one or more embodiments, sensor spacing in the device is derived from the concept of tissue wavelength in human organs which describes the minimum circumference of circuits of spatially linked activity. Wavelength is calculated as the product of minimum tissue refractoriness (or time needed for tissue to recover from the last activation), and the slowest conduction velocity (CV). In an embodiment for the heart, this is represented as the product of action potential duration (APD) with CV. In human atrium, minimum APD is on the order of 100 ms and slowest CV on the order of 10 cm/s. This provides a wavelength on the order of 1 cm and, if circular, a minimum diameter of 1/π or about 0.32 cm (3.2 mm). For organized rhythms such as sinus rhythm, atrial flutter, ventricular tachycardia and so on, the spatial scale of the rhythm is far larger than the minimum tissue wavelength, and can be mapped by widely separated electrodes. However, as rhythms become less organized, the spatial scale may shrink until critical regions that drive or influence the rhythm may approximate this tissue wavelength. Thus, even in spatially disordered rhythms such as AF, an electrode separation on the order of 3.2 mm should be sufficient to map sites with spatially coherent activity such as consistent repetition, rotational or focal sources or drivers, that may be present within disorganized activity in atrial fibrillation or ventricular fibrillation. It should be noted that tissue wavelength does not apply to activity that is not spatially coherent, such as noise, colliding wavefronts or fibrillatory (disordered) activity, in which adjacent sites are not functionally linked. Smaller electrode spacing <3.2 mm may thus be needed if it is desired to map the detail of spatially incoherent (unlinked) activity in fibrillation, or noise, or activity from rapidly changing sources.

A typical embodiment for mapping AF would be 16-64 electrodes in an area of 1 $cm^2$ to 3 $cm^2$. Different embodiments may require smaller or larger catheter designs depending on practical considerations and tailored to the biological organ under study. A typical embodiment for mapping gaps in a pulmonary vein lesion set or a linear ablation set ('line') would be in the range of ~9-25 electrodes in an area of 1-2 $cm^2$, since meaningful gaps are on the order of 1 to 10 mm in width. A typical arrangement for mapping critical regions for ventricular tachycardia would be ~9-36 electrodes in an area of 2-4 $cm^2$.

The size and shape of each sensor can also be personalized to the profile of the patient, as described in FIG. 3-5. This can be performed using tools such as trained machine learning or statistical models based on patients of similar clinical type and data. In one embodiment for mapping critical regions for AF, FIGS. 4A and 4B show that the ideal size of sensing elements is 1-2 mm diameter, spaced ~3 mm, and covering approximately 1-9 $cm^2$ of tissue or more. In another embodiment for mapping critical regions for VT, the ideal size of sensing elements is 1-2 mm diameter, spaced ~3-4 mm, and covering >~2-9 $cm^2$ of tissue.

FIG. 6 illustrates 5×5 electrodes in a uniform grid. The choice of an odd number of electrodes along each axis enables the device to provide a 'center point' with peripheral electrodes in a symmetrical design to map centrifugal activation from a focus or uniform circular re-entry around this central point. Embodiments with 4×4 electrode configurations are also possible but do not provide symmetry about the central axis. Other even combinations of electrodes require an off-center electrode at the center of rotation or focal activity, with an asymmetry of surrounding electrodes which may be wasteful of size and may encounter practical recording limitations in clinical electrophysiological amplifiers that have a fixed number of recording channels.

In other embodiments, the array may be non-uniform, i.e., the electrode spacing is not formed by repetition of one pattern. For example, the spacing between adjacent splines 630 can vary or the spacing between electrodes on a single spline can vary. Typically, the number of channels that can be sensed in a patient is limited by the recording amplifier. The advantage of a variably spaced array is this fixed number of electrodes can be distributed with a high-spatial solution in a central cluster to define ablation patterns, yet with peripheral electrodes to enhance directional navigation (for instance "move catheter left") In one or more embodiments, the characteristics of the electrode array 440, i.e., placement of each electrode within the electrode array 440, can be tailored and optimized for a particular patient, as will be further described in FIG. 16-17.

Each electrode of the electrode array in panel 610 is capable of sensing electrical signals of the heart tissue and for delivering ablation energy to the heart tissue. Each electrode is formed from a conductive material coupled circumferentially to the respective spline that the electrode is disposed on. Example materials that can be used to form the electrodes include, but are not limited to, gold, platinum, metal alloys containing gold, metal alloys containing platinum, gold-plated copper, other conductive metals, other conductive metal alloys, etc. In one or more embodiments, the electrode material is also safe for use in blood. For example, the size of each electrode in FIG. 6 is on the order of 0.8 mm diameter (it is a cylinder), measured along the center axis 620 and 1 mm along the spline. This small electrode sizing provides for very-high-resolution sensing by the electrode array 610. It is well understood that the size of a measurement device (in this case, an electrode of the array 610) limits the measurement resolution that can be achieved by the measurement device.

In some embodiments, the inventive process includes the ability to provide deep and durable tissue modification or destruction ("ablation") through small electrodes, which are also well suited to sense at high resolution. This enables very precise and specific ablation patterns to be delivered in regular, irregular and personalized shapes tailored to the specific rhythm disturbance in that patient. The ability to deliver ablation through these small electrodes is attributable to the materials used in the inventive process and the energy waveform approaches.

In a sensing configuration, each electrode can be configured to measure electrical signals and to provide the electrical signals to the control system 110. The electrical signals collected by each electrode can include: a voltage signal, a current signal, an impedance signal, another electrical parameter, etc. The spacing between adjacent electrodes in the electrode array 440 can be sufficiently small so as to provide high-resolution sensing of the electrical activity of the heart tissue. The electrical signals are used by the control system 110 to determine guidance instructions for movement of the catheter 400 towards a source region that requires ablation therapy.

In an ablation configuration, each electrode can be configured to deliver ablation energy to heart tissue. The ablation energy is in the form of electrical energy received from the generator 115. As noted above, the ablation energy may be tailored, e.g., at a particular frequency or wavelength, with a particular waveform, over a particular duration. This includes common 'moderate power, moderate duration' energy such as 30-50 W at 15-60 seconds, as well as 'high power short duration' energy such as 50-90 W at 5-15 seconds. This also includes very high powers associated with pulsed field ablation (to cause irreversible electroporation). Each electrode, in the ablation configuration, is capable of achieving >3 mm in depth of delivery of ablation energy. As each electrode is addressable independently, the electrode array 440 is capable of delivering ablation energy in a variety of ablation patterns that can be tailored to each critical region for the biological rhythm disorder identified by the control system 110. This is advantageous as the catheter 400 need not perform multiple ablation steps to achieve a particular pattern, which would otherwise be the case with singular ablation electrode catheters or even linear ablation catheters. For example, to create a cross pattern with a linear ablation catheter, the linear ablation catheter would need to perform at least two steps to ablate the two arms of the cross pattern with the additional movement necessary to change positions of the catheter. However, the electrode array 610 of the catheter 155 could achieve the cross pattern by selectively addressing all the electrodes in the middle spline and the middle electrodes in the other splines. The electrode array 610 could thus ablate with the cross pattern in a single step, without needing to reposition the catheter 155. In this fashion a circular, arc shaped or other ablation configuration can be readily delivered depending on the physician selection for that biological rhythm disorder in that patient.

In one or more embodiments, one or more temperature sensors may be implemented on the catheter 610. The temperature sensors measure a temperature of tissue in contact with the temperature sensors. Temperature sensors can be near multiple electrodes, on each spline or in other configurations. In one or more implementations, the temperature sensors measure a change in electrical resistance, electrical voltage, or another electrical metric within a circuitry having a temperature-sensitive material. Example temperature sensors include a resistance temperature detector, a thermocouple, a thermistor, etc. In other embodiments, non-contact temperature sensors may be used, e.g., infrared photoelectric sensor.

In one or more embodiments, one or more force-sensing elements may be implemented on the catheter 610. Force-sensing elements measure a contact force between the catheter 610 and the tissue. The measured contact force can be used to verify contact between the catheter 610 and the tissue during sensing and/or ablation. The force-sensing elements may be piezoelectric sensors, surface capacitance sensors, etc.

In one or more embodiments, one or more photoelectric sensors may be implemented on the catheter 610. The photoelectric sensors may be used to identify changes to tissue composition prior to, during, or after ablation. The photoelectric sensors may also be infrared sensitive to determine a temperature of the tissue.

Ablation in a preclinical model is shown in FIG. 6 panels 640 and 650. The catheter was passed through femoral veins into the right atrium of a 25 kg pig under general anesthesia. Segments of 2×2 electrodes were ablated while titrating power and duration. A selected experiment is shown. Panel 640 shows gross pathology on the right atrium for an area >1 cm×1 cm ablated, as expected slightly larger than the physical electrode subarray of 3.6 mm (0.8 mm diameter, with 3.0 mm center to center spacing) in one axis and 4.0 mm in the orthogonal axis (0.8 mm diameter, with 3.0 mm center to center spacing). Panel 650 shows full thickness (transmural) ablation, indicating depth >3 mm. Power of <40 W across 4 electrodes for 30 seconds (<10 W per electrode) can achieve varying depths of penetration. Irrigation prevents charring and minimizes safety issues from ablation.

Reconstruction of Physiological Signals

FIG. 7 provides detail for reconstruction of physiological data from clinical recordings in multiple organs in the body. In some embodiments, this is termed 'deriving' signals from the signals detected by the sensing array. Panel 700 indicates several organs in the body which may exhibit disturbance of biological organ, and from which electrical signals can be recorded (or detected, sensed). This includes the brain, heart, nerves, gastrointestinal system, bladder and skeletal muscles. The reconstruction described in FIG. 7 may be one of the models 190.

Panel 720 indicates how catheter recordings obtained in patients often do not faithfully represent actual tissue physiology. Panel 730 indicates nerve (neural) signals measured from the brain (electroencephalogram, EEG), muscle (electromyogram, EMG) or nerves (electroneurogram, ENG). Clinical signals often appear as very rapid, difficult to discern signals. However, actual nerve electrophysiology takes the form of action potentials of duration ~3-5 ms (indicated) which are quite different to clinical recordings. This difference is more marked in the heart (panels 740 and 750). In the atrium during AF 740, catheter signals often appear spiky, chaotic and varying in amplitude and duration from ~5-150 ms. Conversely, true tissue physiology comprises action potentials of duration ~100-140 ms. In the ventricle during ventricular tachycardia 750, catheter signals often comprise spiky large components and small fractionated signals (termed diastolic potentials). True ventricular electrophysiology comprises action potentials that are far more regular, and more 'square' than in the atrium, although with varying duration and rate.

Panel 760 summarizes the inventive reconstruction of true physiology from clinical signals. Catheter signals are input 765. Other personalized information 770 can be input, such as age, gender, heart structure, heart size, left atrial size, left ventricular ejection fraction, and other features relevant to the biological rhythm under consideration. This is then used in a learning machine 780, trained to matched ground truth labels 775 (output labels during training). In one embodiment, the ground truth labels represent action potentials that can be recorded in AF or other rhythms in patients using a specialized catheter, termed a monophasic action potential catheter which faithfully reflects tissue action potential durations. The learning machine is trained to indicate from the input catheter recordings what the onset and offset (end) of action potentials would be for each cycle of the biological rhythm disorder. Once trained, the learning machine does not need ground truths, and can reconstruct action potential onset and offset from catheter recordings 765, with or without personal data 770.

FIG. 8 provides detail for the learning machine designed to reconstruct tissue physiology from recordings in patients from a sensing device. In step 800 raw data is input, which can include clinical recordings from ECG or electrical signals from within the heart (electrograms, EGM), or non-invasively sensed signals such as from the body surface or from a magnetocardiogram (MCG), Imaging data from CT or MRI, or clinical data for personalization such as age and so on. The different types of data inputs can be used separately or using a combination of the data inputs. Data from step 800 can undergo data derivation or preprocessing in step 805 or feed directly to the model in step 810.

Step 805 is data derivation and pre-processing for physiology reconstruction. In some embodiments, pre-processing may include high-pass filtering above 0.5 Hz to remove baseline oscillation or other artifacts, but different high-pass filtering frequencies can be selected. In another embodiment, pre-processing can include low-pass filtering to remove electrical noise or other artifacts. Filtering can include also narrow-band pass filtering at spectral band determined by features of the signal under analysis or other signals. For instance, some important features of AF in the frequency domain can be identified in bands of 0-20 Hz, such as the frequency of the main or secondary spectral contributions, their width and relative amplitude as well as the relative spectral content for certain frequency bands compared to the total spectral content. A band-stop can also be used to process signals to remove high frequency noise such as 50 Hz or 60 Hz alternating current (AC) noise, or other background noise or unwanted signals with specific frequencies. A smoothing filter based on mean or median averaging can also be used to remove other artifacts from the signal such as sudden spikes from electrical components or sudden movement. Other pre-processing techniques may also include normalization (e.g. using the maximum and minimum values or using z-score normalization).

One embodiment applies ventricular activity cancellation when the aim is to identify signal patterns from the atrial chamber. In some embodiments, the ventricular cancellation algorithm is based on detection of the instant of ventricular depolarization using a combination of linear and non-linear filtering and identification of local maxima. The ventricular cancellation algorithm could be based on ventricular shape average and subtraction using one or more torso signals. The ventricular cancellation algorithm could be based on partial component analysis using different ventricular beats.

Electrical signal processing may comprise broad-use featuring libraries for signal processing, such as tsfresh. Electrical signal processing may comprise spectral analysis using the Fast Fourier Transform, the Welch Periodogram, Discrete Cosine Transform, Hilbert Transforms, Principal Components Analysis, convolutional-based transform, or the continuous wavelet transform. The spectral analysis could be also based on the combination of spectral transformations after different linear or non-linear filtering, such as low-pass, high-pass, band-stop, or band-pass filtering. In other embodiments, derived data can include spectral analysis of time series signals or images such as spectrograms in which information on frequency spectrum and how it varies with time can be found. Data derivation techniques presented can be applied to different data types including 1D inputs (e.g. voltage time series signals) or 2D signals (grayscale images), or 3D data (colored images or grey scale videos), or higher dimensionality signals as defined by user.

The spectral analysis could be used to detect the main spectral contribution using the following formula:

$$DF = \vartheta(s_{ECG})|_{\vartheta(s_{ECG}) = max(\|\vartheta(s_{ECG})\|)}$$

In the above equation, DF is the main spectral contribution or Dominant Frequency, $s_{ECG}$ is the signal under analysis and $\vartheta(s_{ECG})$ represents the spectral transform by Fast Fourier Transform or Welch Periodogram. The electrical signal processing module may perform identification or other secondary spectral contribution using the local maxima of the spectral transform. The electrical signal processing module may perform analysis of the spatial distribution of the DF values in order to identify regions with the same or different values of DF.

The electrical signal processing module may perform analysis of the phase of the electrocardiographic signal, using the following or other formula:

$$phase(t) = arctan(imag(hubert(s_{ECG}(t))), real(hilbert(s_{ECG}(t))))$$

In the above equation, phase(t) is the instantaneous phase transform of the signal under analysis $s_{ECG}$, and image( ), real( ) and hilbert( ) represents the imaginary- and real-part extraction and Hilbert transform functions respectively. The electrical signal processing module may perform the analysis of the phase from individual signals, by identifying the fiducial points such as local maxima or transitions from/to pi/−pi. The electrical signal processing module may perform the analysis of several instantaneous phase signals in spatial maps, using spatial interpolation of the phase signal in each instant and position to cover all the surface torso between electrodes of the electrode array. This spatial interpolation could be carried out using linear interpolation, cubic splines or other interpolation methods, and could be carried out without the use of torso anatomies and shapes extracted from medical image (MM, CT) techniques. The electrical signal processing module may perform the analysis of the instantaneous phase maps through the identification of the phase transitions, that is, the lines in which the phase map transits from pi to −pi.

The electrical signal processing module may perform the analysis of spatial phase singularities using the following formula:

$$\text{singularity}(t) = \oint_{0,D}^{2\pi} \text{phase}(s_{ECG}(t)_{x,y})$$

In the above equation, the operator $\oint_{0,D}^{2\pi}$ represents the spatial integral over a circle with radius D and $s_{ECG}(t)_{x,y}$ is the electrocardiographic signal at interpolated coordinates X and Y. The computing server may perform identification of instants and points in which the singularity(t) provides values different to 0 and summarize and cluster them to measure the spatial and temporal complexity of heart arrhythmia. The computing server may perform the analysis of the temporal features of the signal as the number of local maximal after band-pass filtering. The computing server may perform the analysis of the first and second derivatives of the torso surface signal in order to identify their percentiles and quartiles. The computing server may perform autocorrelation analysis of the electrocardiographic surface signals.

Step 810 involves building and training the machine learning and statistical models. Step 810 can comprise of one model or several models from Machine Learning models and statistical algorithms. Machine learning models include Deep learning with neural networks, traditional machine learning model, or statistical models.

One example embodiment of using traditional ML or statistical methods for model 810 is using features from time-series data (e.g. dominant frequency, mean voltage, etc.) or from clinical variables (e.g. age, gender, weight, etc.) to train a model to predict a specific outcome (e.g. presence of driver or success probability).

The output of the ML model 810 is represented in step 815. The output of the ML model 810 can be a single value or multiple values and can be binary or continuous depending on the application. The output 815 is used to optimize ML model 810 mapping input data 800 and 805 to output data 815. For heart rhythm disorders such as AF, physiology reconstruction outputs will be activation onset times and offset times validated using action potentials.

One embodiment is illustrated in step 820, where the predicted output in step 815 is used again as the output to retrain the ML model in 810. This method is particularly useful if the training dataset is large but also contains a small percentage of errors in the output or labeling. In large datasets, the ML model 810 learns to optimize for most of the correct labels in the dataset and thus can produce predicted outputs that have the correct labeling instead of the original faulty labels.

Several example embodiments are shown in FIG. 8. The first embodiment is shown in step 830, in which an ML model 840 is trained using input data 835 with labeled outputs 845. Transfer learning, a second embodiment shown in 849, a different ML model 855 is trained using the initial weights 841 of the trained ML model 840. ML model 855 is trained by continuing to optimize weights of partial layers (commonly for later feature extraction and prediction layers) and freezing weights in other layers (commonly earlier layers that extract simple features) in ML model 855. Transfer learning 849 is particularly useful for training small datasets but can also be used to improve computational speed if training a new model with a new dataset, since weights are already optimized to extract relevant features. Another embodiment is semi-supervised learning, in which a trained ML model 840 is used to generate labels 875 for an unlabeled dataset 870. Semi-supervised learning is commonly used for labeling datasets (transductive learning) or improving ML model input to output mapping (inductive learning). For example, in a dataset that is only half labeled, a model can be trained using only the labeled half of the dataset, the trained ML model can then be used to generate ML derived labels for the unlabeled half of the dataset. The complete dataset (half with original labels and half with ML derived labels) can then be used to train a new model. Another embodiment is shown in FIG. 880, in which a model is trained to map from input dataset 885 (e.g. EGMs) to output 895 using 1, 2, . . . , or $n^{th}$ ML models 890, where n>=1. Embodiment 880 is an example of an ensemble ML method. The input dataset to each of the ML models can contain voltage-time series data, imaging data, or clinical data in the raw, derived, or preprocessed form (800, 805). These techniques allow each individual model to optimize feature extraction from different inputs and the different output predictions is combined (e.g. using majority vote, average, or weighted averaged) to produce the final output.

In one preferred embodiment, The ML model 810 is trained to predict activation onset times using one or more of the input data structures in FIG. 9. In this embodiment, the ML model architecture 810 is a sequential model comprised of 1D convolution layer (filters=32, kernel size=20, and ReLU activation function), followed by 1D max pooling layer (pool size=2, strides=1), followed by a dense layer (units=3, ReLU activation function), followed by a GRU layer (units=4), followed by a dense layer (united=16, ReLU activation function), followed by a Dense layer (units=1, sigmoid activation function). In this ML model embodiment, a 1:1 input to output relationship can be implemented in order to preserve the temporal resolution (e.g. 2000 samples input and 2000 samples output). The model can be trained with a binary cross-entropy loss function and an optimization algorithm such as the Adam algorithm. Said embodiment architecture can be used with a different number or order of convolutional, recurrent, or other layers or adding different connections (e.g. residual connections). Moreover, different parameters values (e.g. filters, kernel size, activation functions), optimization functions, or loss functions can also be used to fine tune the ML model.

FIG. 9 indicates some types of signal features that may be useful for efficient training of learning machines. The signal features in FIG. 9 can be used separately or in combination of one another to train ML model 810 to map from input to output. Features in FIG. 9 can be in any order from top to bottom. One feature used is the EGM shown in 900, the EGM used can be raw or QRS subtracted to remove ventricular components. Another feature that can be used is the ECG shown in 905, which can be filtered, smoothed, scaled, or preprocessed using one of the techniques discussed in step 805. Panel 910 shows the Bipolar EGM, which can be obtained directly from clinical recordings or derived in step 805. Panel 915 shows the smoothed EGM, which is derived from the EGM 900 using techniques discussed in step 805 such as a smoothing filter. Panels 920 and 925 show the first and second derivatives of the EGM 900, derived in step 805.

Panels 930 and 935 show the first and second derivates of the smoothed EGM 915, derived in step 805. Panel 940 shows the first derivative of the ECG signal, which is preprocessed using techniques discussed in step 805. Panels 945 and 950 show the first and second derivatives of the bipolar EGM signal, which can be derived in step 805. Panels 955, 960, and 965 show a smoothed version of the signals in panel 910, 945 and 950. The features in FIG. 9 are useful for training ML models to detect important points in clinical signals such as onset and offset times in Atrial Fibrillation. Moreover, each feature in FIG. 9 can be preprocessed using methods such as filtering, smoothing, scaling, or other types as discussed in step 805.

FIG. 10 shows examples of the accuracy of finding tissue action onset and offset using one embodiment of the trained ML model (810) using clinical signals in AF as the input (800, 805) to the trained ML model (810). In Panels 1010, 1020, 1040, and 1050, three different signals are shown in each panel: the ECG signal (1011, 1021, 1041, 1051), the clinical EGM signal (1012, 1022, 1042, 1052), and the MAP signal (1013, 1023, 1043, 1053). In 1010, 1020, 1040, and 1050, the MAP signal (1013, 1023, 1043, 1053) was recorded simultaneously with the clinical EGM signal at the same location (1012, 1022, 1042, 1052). Panels 1010 and 1020, show two examples in which the trained ML model (810) predicted MAP action potential activation times (e.g. 1014, 1024) within an error ≤10 msec. In one embodiment, a separate testing data (not used for training or validation), the trained ML model (810) achieved an AUROC of 0.97 with a mean error of 6.7±4.4 msec (range 0-20 msec) for detecting onset times of verified activation events (true positives). In panel 1020, the ML model was able to predict onset times even in a lower quality clinical EGM 1022. Moreover, panel 1020 also shows the trained ML model 810 avoids tagging artifacts 1030 (non-local activation in this case). Panels 1040 and 1050 show the trained ML model (810) predicting offset times that agree with the offset of action potentials during AF. In 1040 and 1050, notice that the ML can predict offset times even when clinical EGM signals do not follow a typical action potential shape (1052). Panel 1080 shows accuracy of the learning machine for action potential onset timings with an area under the curve of 0.97, based on error in timing of ≤20 msec being a true positive. This 20 ms point was selected here because it is in the range of inter-observer variation of experts. In many cases, the error from the invention is considerably lower than this 20 ms threshold (in one embodiment, onset activation had a mean error of 6.7±4.4 msec for true positives).

FIG. 11 shows an example embodiment for training a learning model 1160 with personalized and non-personalized data. In one embodiment, the learning model 1160 takes in local or specific disease data 1110 such as standard data including electrograms or information on critical AF sites, as well as other patient specific features which may not otherwise be used to guide therapy, such as clinical personalization 1120, technical personalization 1130, temporal personalization 1140, spatial personalization 1150, or others. The combination of disease specific data 1110 and personalized features (1120 to 1150) allows the model 1160 to extract complex relationships that are not possible to extract with traditional methods.

Further considering FIG. 11, the learning machine 1160 can use one or more of the models described in 810 or other methods. For example, one current method to find critical AF sites is by analyzing intracardiac signals (EGMs), and their activations identified with prior ML models 810, which are a form of specific disease data 1110. However, this does not take into account variations that may occur due to clinical factors such as age, weight, arrhythmia type, atrium size, prior ablations or other data. A personalized learning machine 1160 can build relationships between several different input features—allowing personalization at several different levels by the ability to add additional features. For example, the addition of atria volume can enable the model to learn the relationships between critical treatment regions, heart voltage amplitude, and atrial volume. Another example is the addition of AF type and its relationships to EGM shapes in intracardiac signals. The learning machine 1160 can associate such relations if any exist. Moreover, input features to the learning machine 1160 are more comprehensive and can process data in different forms such as voltage-timeseries features (e.g. ECGs or EGMs), imaging data (e.g. CTs or MRIs) or other clinical features 1120 (e.g. age or weight).

FIG. 11 also shows embodiments in which the learning machine can personalize based on technical features 1130. This enables machine learning algorithms to be tailored to electrode type or size, their configuration in a 2-dimensional array in distinction to a 1-d array (a linear catheter), or factors relating to a 3-dimensional spherical or ellipsoidal array. Other technical factors for personalization include the shape of each sensor element, such as cylindrical, spherical, ellipsoid and so on. Other technical factors include the material of which sensor elements are made.

FIG. 11 shows that some embodiments may also personalize based on temporal features 1140. This can include the time of day that recordings are made, since some rhythms show a diurnal variation. For instance, some patients with AF experience episodes at night, or during peak exertion. Temporal personalization can also take duration of rhythm disturbance into account. Some episodes of AF, in particular, are of short duration while others may last days or weeks. Machine learning can be tailored separately for shorter and longer durations, which may indicate different mechanisms and may require different therapy.

FIG. 11 shows that personalization can also be based on spatial features 1150. This may include the chamber in question. In the brain, this may be the cerebral cortex, frontal lobe, parietal lobes, occipital lobe, cerebellum or brainstem, deep brain structures, peripheral nerves and so on. In the heart, this may be the right atrium, left atrium, right ventricle, left ventricle, aorta, other vessels and other structures that will be familiar to one skilled in the art.

In other embodiments, personalization of machine learning can include classifying an individual's personal data profiles based on patterns associated with response to therapy or lack of response to therapy. Machine learning may be trained by objective and clinically relevant labels such as successful response to therapy (e.g., elimination of AF by PVI ablation, elimination of VT by ablation, improvement in left ventricular ejection fraction by ablation of heart rhythm disorder), or adverse response to therapy (e.g., prolongation of the QT interval by pharmacological agents, failure from to ablation). The machine learning model can now make a prediction for an individual from their closest pattern match.

In one embodiment, the personalized ML model 1160 takes as input signals and derived features 900 to 965 in FIG. 9 (4 seconds sampled at 500 Hz, i.e. 2000 samples) as well as their activation times identified by the prior ML model 810. In one embodiment, output of the ML model can be the probability of the recorded intracardiac region to be a therapeutic target, defined as an AF driver, a site of AF termination or other electrophysiological and clinical features. In one embodiment, output of the ML model can be the probability of each spline or set of electrodes of the recording catheter 610 to be close to a therapeutic target outside the catheter recording area. In one embodiment, output of the ML model can be the relative distance of the recording catheter 610 to a therapeutic target outside the catheter recording area, or the probability to find a therapeutic target outside the catheter recording area closer than a defined distance. Said embodiments can also consider mixed architectures, including several inputs as images 1110 (MRI/CT), demographics 1120 (age, gender, heart size, etc.), electrode configuration 1130 (size, area, etc.), temporal aspects 1140 (time of day, etc.) and spatial personalization 1150 (atrium, ventricle, etc.). It should be noted that single features above can be used for ML model training and hence to guide diagnosis and therapy. For instance, ML based on features of the MRI such as delayed enhancement by gadolinium (which may reflect scar or prior ablated tissue) can be used the basis for an ML model alone. ML models based on other physiological features will be apparent to one skilled in the art.

By using machine learning, the system individualizes treatment and does not cater just to the statistical majority of individuals who respond to a therapy, or to populations most represented in the literature. This is a practical implementation of FAIR software methods (Findable, Accessible, Interoperable, and Reusable) to reduce bias—for instance, to cater therapy to an individual even if they differ demographically or physiologically from the 'average' patient in prior reported populations. This enables machine learning in this invention to be broadly generalizable to under-represented minorities even if training data is from a narrow population (e.g. Caucasians).

Personalization can be encoded by computer and analytical methods based on associative algorithms, data clusters including unsupervised machine learning, semi-supervised machine learning, and supervised machine learning and networks trained by labeled events in similar and dissimilar individuals. The tailoring of personal digital records to therapy is enabled by partitioning data with labels of 'healthful vs disease', 'responsive to therapy vs non-responsive', or multiclass response to therapies labeled such as 'therapy 1', 'therapy 2', . . . , 'therapy n'. Analysis can be one or more of supervised machine learning, neural networks, unsupervised machine learning, cluster analysis, correlation analyses, logistic regression analyses, decision trees, time domain analyses, frequency domain analyses, trigonometric transformations, and logarithmic transformations.

Personalization for heart rhythm may use signals that capture the rhythm. This may include electrical potentials (electrograms) from a non-invasive device or invasive device within or adjacent to the heart. Other signals that can be analyzed include heat (infrared), mechanical motion (piezoelectric or other sensors), chemical composition, blood flow and pressure (hemodynamics), wall tension (cardiac contractility and relaxation), Cardiac Images (magnetic resonance imaging, computed tomography), or other indices that may have diagnostic value. More detailed data includes three-dimensional anatomical and structural abnormalities. Clinical data can be extracted from history and physical examination, indices of pathophysiological comorbidities, blood and tissue biomarkers, and genetic and cellular makeup of an individual. Non-invasively, sensors may record the standard electrocardiogram, surface recordings from higher resolution body surface potential mapping (e.g., multiple ECG electrodes) or ECG imaging, cutaneous measures of nerve activity. Reflectance on the skin to visible light or other electromagnetic waveforms can be used to measure signals that indicate heart beats, either regular or irregular. This can be detected using photoplethysmography (PPG) or other forms of detecting reflectance. Visible light in the near-infrared portion of the spectrum may be useful for this. Other types of sensed signals that may be used will be apparent to one of skill in the art.

FIG. 12 shows another embodiment in which action potential tracings can be approximated or generated using computational techniques applied to clinical signals. In FIG. 12, from outputs from steps 800, 805, 810, 815, ML models (810) such as linear, quadratic, or cubic regression or other ML models are used to model action potential offset times. In the most simple form, a triangle can be used to approximate atrial action potential shape, a modified rectangle for the ventricular action potential, and other shapes for other types of action potentials. Steps 1200-1260 are useful in cases where the action potential shape is not regular.

In steps 1200-1205 in training, a single action potential is identified along with its start and end times. In 1210, the baseline 1211 of the action potential is found, and phases 2 (1212) and 4 (1214) are also found using traditional algorithms or ML models. In step 1220, the points from phase 2 (1212) to phase 4 (1214) are examined to find if any irregularities in shape are present. Irregularities in phase 2 to 4 shape (1213) can be found based on template matching, sudden changes in $$\frac{dV}{dt},$$

or ML models. It no irregularities are found in step 1220, the model proceeds to calculate the action potential offset time (APD 70, 80, or 90) based on the original raw MAP in step 1230. If irregularities are found in step 1220, phase 2 to phase 4 of the action potential is modeled in step 1240 using one of the ML models described in 810. The action potential offset time (APD 70, 80, or 90) is then calculated based on the modeled action potential phase 2 to phase 4 (1241) and modeled phase 4 (1242).

In another embodiment, the mathematical steps needed to approximate or model the action potential shape (1200-1242) can be used to generate an entire action potential shape as in step 1260. This case can be useful when the onset times are known, such as from the steps illustrated above in FIG. 11, but the offsets are less clear. Steps 1200-1260 can be used successively for each activation onset time to computationally reconstruct a series of action potentials at that electrode during the recorded rhythm. This can be useful for mapping as shown below in FIG. 13.

Spatial Map Generation

FIG. 13 indicates types of spatial map that can be generated by a featurization model based on sensed signals (corresponding to Step 230 in FIG. 2). Another term for this process is to determine the landscape for the biological rhythm. In each panel 1320-1350, the square corresponds to the configuration of sensing elements (electrodes). Panel 1310 indicates electrodes in a 5×5 grid of 2-dimensional array, from a catheter in a preferred embodiment with 1 mm electrodes arranged with spacing 2-3 mm. Other embodiments may be used including 1-dimensional and 3-dimensional configurations. Raw recordings from biological tissue are analyzed as in the specification to create spatial maps. Panel 1320 shows a sample embodiment in which activation times are plotted across tissue using activation onsets alone, either from tissue reconstructed physiology (step 220 in FIG. 2) or from raw data.

Virtual optical mapping can be achieved in step 1330 by a map of action potential timings. This map is a computerized reconstruction of a fluorescence-dye related optical map. This embodiment uses onset and offset times of reconstructed action potentials (tissue physiology) across the mapping field, or even reconstructed action potentials as in FIG. 12, and can be generated with or without spatial interpolation or temporal interpolation. This is a significant advance over the prior art, since optical mapping of action potentials using fluorescent dyes is not currently possible in patients due to dye toxicity (when dyes are used), difficulty in imaging dye fluorescence through blood (in animals, this is done through transparent infusions that replace blood), and difficulty in imaging the moving heart. This invention enables action potential maps of the type possible by 'optical imaging' to be accurately reconstructed by the clinical catheter in patients in any location.

Step 1340 shows a feature map, in which critical regions indicated in step 250 in FIG. 2 can be plotted as indicated. Hotspots in the color coding can represent rate, voltage or indices of dispersion.

Step 1350 indicates a map of Arrhythmia Bar Codes in which reconstructed action potential onset and offset times are used to code a binary "ON" or "OFF". This produces a series of ON/OFF signals at each electrode over time. Putting these together for all electrodes on the spade catheter can quickly indicate sequential activation (panel 1355) or focal activation (panel 1360) or other patterns.

FIG. 14 illustrates spatial features summarized in 250 of FIG. 2, which may also be termed regions of interest, sources, drivers, critical sites, critical regions, or targets for therapy. Several may be identified within a spatial map of a patient, and contribute to the arrhythmia landscape for that patient. It should be noted that spatial features derived from reconstructed tissue-based signals in this invention (see FIGS. 7-12) can be quite different from spatial features derived from signals initially detected from each sensor (see FIG. 7, 10), and have been shown to be more accurate. Example spatial features in FIG. 14 plot tissue activation (or tissue-based physiological signals, or MAPs) to show: 1400 is a focal activation; 1405 is complete rotational activity; 1410 is incomplete rotational activity; 1415 indicates rapid rates; 1430 shows a map in which equally timed contour lines 'crowd' or 'bunch' in one region, indicating conduction slowing which can be a critical site for arrhythmias; 1435 shows repetitive patterns, which may be repeating instances of any of these patterns; 1440 shows low amplitude (gray/black) in otherwise healthy voltages, which can indicate a gap; 1460 enables the physician to define a signal that they wish to map in this patient and rhythm; 1465 indicates a suggested feature, using AI from the device personalized for that patient; 1470 indicates use of a library from this or other patients, to indicate features where therapy may have success and features associated with lack of success of therapy.

A featurization model (e.g., one of the models 190) may identify the spatial features based on the sensed signals. In some embodiments, the featurization model inputs electrophysiological signals that are reconstructed by a reconstruction model. The featurization model may be a machine-learned model (e.g., a classification model) that inputs the sensed signals and output one of the types of spatial features.

Directional Guidance

FIG. 15 provides one embodiment for catheter guidance (an expansion of element 270 in FIG. 2). Element 1510 inputs signals measured by a probe or catheter. Catheters that can be used include 1525 (spade), 1530 (circular mapping catheter), 1535 (basket type catheter), or 1545 (other shape). Ultimately, the guidance direction is provided in the form of a vector (direction to move, and extent of movement).

In one or more embodiments, a non-invasive 1540 body surface mapping device or wearable can use a plurality of carefully placed electrodes on the body surface to map the heart rhythm disorder. Conventionally, anatomical information of the patient from detailed computed tomography (CT) or magnetic resonance imaging (MRI) data is needed. Of note, the spatial resolution needed to identify important patient groups or rhythm types can provided by this invention without the need for CT scan or MRI data. This increases the usability of the approach over existing methods based on CT or MRI, since the body surface device is suitable for fully outpatient use without hospital visits for imaging. In some embodiments, navigational guidance from the body surface is a spatial guide to assist navigation of a device inside the heart, such as a catheter 155. In a simple form, guidance can identify rhythms arising from the left side of the heart versus the right side of the heart. In a more advanced but still simple form, information is of sufficient spatial resolution to separate beats originating from pulmonary vein regions versus those arising from other regions of the atria. Of note, the pulmonary veins and posterior left atrium project to the back of the torso and are of known importance as treatment areas for patients with AF. This level of resolution can be achieved by body potential surface maps without CT or MRI data. This embodiment using the body surface can dispense with the need for cumbersome global 'basket' catheters which may be bulky, time consuming to use and expensive.

In some embodiments 1540, the device is a non-invasive ECG device that is artificial intelligence (AI) enabled, and simple enough to be applied to the chest or back by the patient at home. The single-use device will be worn for up to several days, will automatically detect the onset and then ongoing episodes of the heart rhythm disorder, and alert the user when sufficient data is recorded. Data is transmitted to the cloud for analysis, from which results can be available via electronic health records for review. Analysis can indicate if that patient will respond to ablation near the pulmonary veins, for instance, or to ablation on the left or right side of the heart. If results suggest that a patient does not have these sources or triggers for their biological rhythm disorder, a decision may be made to treat them with medications. The physician can thus make a fully remote care plan, without the need for in-hospital evaluation or invasive testing. This is useful to streamline costs, provide access to patients in rural areas, and minimize hospital contact during public health emergencies such as the COVID pandemic. One target indication is whether to refer an AF patient directly to pulmonary vein isolation (PVI), advanced ablation, or drug therapy.

In some embodiments, the guidance system uses additional inputs 1550, such as clinical data, library patterns and filtering patterns used in this signal acquisition. Signals may be raw or processed by one or more data processing techniques discussed. Clinical data includes a library of profiles for a plurality of patients. Each patient profile may include identifying information and medical records. Identifying information may include name, biological sex, age, one or more current and/or prior medical conditions (e.g., asthmatic, diabetic, etc.). The medical records may include one or more prior diagnoses, one or more types of heart rhythm disorders that the patient has, one or more prior procedures, drug allergies, prior data streams, prior electrical signal data associated with a prior procedure, a current diagnosis, etc. The patient profile may be routinely updated upon the completion of a procedure.

Step 1560 determines if a desired feature is present at this catheter position, which is an important diagnostic step in many embodiments. Logic is based on whether signals match expected patterns of the desired or suggested feature of interest. Several features of interest exist, and a different form of navigational guidance will apply to each. Here, features are referenced back to FIG. 2 features 250. Each feature can be identified from its predicted activation patterns, but also by machine learning of verified patterns used to train models in our invention, as detailed further in FIG. 16.

Step 1560 activity patterns can be identified using activation times from reconstructed tissue signals (FIGS. 7-12), also termed "virtual action potential mapping", or "virtual optical mapping", that is more accurate than prior analyses of signals from clinical catheters that can be misled by spurious signals or deflections that are discarded by our smart approach. Focal activity can be identified by a centrifugal spread of activation from a site. In theory, the net vector across the mapping catheter is zero if spread of activity is isotropic (uniform) in all directions and if the catheter is centered over the focal site. Rotational or reentrant activity can be identified as complete (one or more full rotations) or incomplete (less than a full rotation). Rapid activity can be identified with high accuracy (in which complex signal types or noise may artificially elevate rate or dominant frequency). Conduction slowing can also be identified accurately from reconstructed tissue signals (virtual action potential timings).

Other signal types include complex signal shapes that are characterized by a large number of deflections. Another signal feature is the presence of dispersion of electrograms within a small mapping field, in which signals span most of the cycle length or period of the rhythm disorder, and may indicate localized driver circuits. Another signal type of interest is repeating patterns within a region. Low voltage sites may indicate scar or ablated tissue, and can be identified at any site in the mapping field and can be a target for ablation to eliminate a gap. A gap in an ablated region or scar may be revealed by a localized region of recordable voltage above some threshold (typically 0.1-0.5 mV) in a midst of scar tissue. Borderline voltage may be observed adjacent to scar or ablated tissue, and can also be a target for ablation therapy.

Rhythm bar codes are an inventive approach to visualize rhythms, based on the onset and offset of tissue signals reconstructed by the invention (FIG. 13). Activity is indicated by a black bar between onset and offset (corresponding to activation, or 'systole'), with period between beats indicated by white (corresponding to rest or 'diastole'). Bar code patterns may represent stable reentry, in which staggered black bars within a region span most (typically over 75% of) the cycle length (period) of the rhythm disorder. Reentry in atrial flutter is spatially fixed in space, with white bars (diastole) present continuously indicating the so-called 'excitable gap'. In AF, reentry is very fast and may spatially meander. White bars will shrink and may even disappear (lack of diastolic intervals), indicating that tissue is activating at close to maximum rate as discussed above. These may be target sites for therapy. Focal activity will show bar codes in which tissue activity (black bars) indicate a small proportion of the cycle length (period) of the rhythm disorder (typically under 50%). Ideally, the mapping catheter will be moved so that the focal site is centered in the mapping field. Another region of interest is a user defined site as indicated in step 1450. These and other features are illustrated in FIG. 13.

Guidance logic 1560 may analyze the proportion of electrodes on the catheter 155 that match the anticipated feature of interest and determine if this is sufficient to make the diagnosis that the feature is present. One manner of calculating the ratio includes determining the area of the electrode array of the catheter 155 that covers the predicted region of interest. If the system 1560 shows that patterns match the desired feature, therapy can be considered in step 1570. If the ratio is below some threshold, the guidance logic model 1560 determines directional guidance 1580 to optimize the position of the catheter 155 overlaying the region of interest.

If the sensing array is not currently positioned at a critical region, directional logic 1580 is provided in some embodiments. Step 1580 Directional logic is analogous to a global positioning system that uses the current position to navigate to a desired location, without requiring the entire map of the globe or remote sites. Thus, this approach can identify location of, or towards, or away from, a site without first needing to map the whole of the chamber of interest (or both atria or both ventricles). This enables high resolution mapping from a small densely spaced array that is of higher resolution than available if the same number of electrodes were placed in a large wide-area, global or panoramic mapping array or basket catheter or noncontact system within the heart, or body surface mapping arrangement.

The guidance direction may be a vector comprising both a direction towards the critical region and a distance of the critical region. Directional guidance 1580 can include movement or 'translation' (up to two degrees of freedom on the surface of the tissue), 'rotation' (up to one degree of freedom, rotating about an axis perpendicular to the surface of the tissue) or moving towards tissue to improve contact or some combination of these spatial movements. Directional guidance takes into account the 3D properties of waves. This is possible because the invention can estimate rhythm properties on both sides of heart muscle (endocardial and epicardial). This can use logic summarized in FIGS. 3-6 and related text to adapt to the width of critical regions on the curved contour of the heart, or the 3D features including depth by assessing the opposite side of the heart (i.e. epicardial if the catheter is placed on the endocardial surface, or endocardial if the catheter is placed on the epicardial surface).

Directional information can take into account other features of the signal matrix acquired 1595 including in the temporal domain and first and second derivative, such as percentiles, number of local maxima or minima, features extracted from the autocorrelation, rhythm signatures, shape irregularities, etc. Other features could be extracted from the parametric or signature analysis.

The guidance model (shown in 1560-1590) may include a model that outputs information relating to an identified critical region. The guidance model may determine a type of critical region, a size and/or shape of the critical region, a strength of the critical region, any other characteristic, or some combination thereof. The information relation to the identified critical region may be provided to the device control module 195 of FIG. 1B to determine an ablation procedure based on the information. For example, the ablation procedure may comprise an ablation pattern that matches to the rotational activity in atrial fibrillation.

In some embodiments, guidance can be achieved by partitioning the electrophysiological signals into a plurality of subsets of electrophysiological signal, each subset of the electrophysiological signals corresponding to a window of sensing elements of the sensing array. The guidance mechanism can thus use all signals from the sensing array, or subsets of signals. In one embodiment, the guidance system first uses a subset of the electrophysiological signals to infer the probability that a feature (FIG. 14) is present in the area neighboring the subset electrodes, and then infers the guidance direction using the results from the different subset of electrodes. In another embodiment, the subset of electrophysiological signals that are on the perimeter of the catheter are used as input to the guidance model 1650 to determine a candidate guidance direction while the subset of inner electrodes are used as inputs to the driver identification model 1670 to infer whether a source is present in the current location of the catheter.

The guidance model (shown in 1560-1590) may include a deep learning, machine learning, or statistical model such as described in 810, classified by or trained to a specific output label such as termination of biological rhythm disorder by ablation or long-term freedom from said biological rhythm disorder. In these models, the invention does not need to calculate specific (deterministic) patterns such as rotation, focal or conduction slowing, but instead the previously trained model will 'recognize' said features. In some embodiments, the guidance model may provide features of the critical region without need for strict classification. The approach has several advantages over the prior art. One advantage is that machine learning internally calculates a best-match without the need for hard-coded cutpoints. For instance, partial, nearly continuous or continuous rotations in AF will result in progressively higher pattern matches against adjudicated rotational features in training, eliminating the need to specify 270 degree, 300 degree or other cutpoints. Another advantage is that the invention has been trained on features whose therapy was associated with positive results. This may greatly reduce the detection of 'false positive' features, such as rotational elements in AF that are of secondary importance or false positives.

The guidance model 1560 may further output a personal clinical arrhythmia prediction, that can identify the specific phenotype of the patient disease such as a likely PV based AF, or AF from sites that arise away from the PVs, or VT that arises from sites common in patients with that phenotype. In some embodiments, the device can perform directional navigation using the EGM information, their activation times and other features. For example, the system can identify whether waves sensed by each edge or side of the catheter are coming towards or moving away from a region of interest or source, and hence calculate a probability of reaching a feature based on movement in a particular direction. The wave sensed vector or features used for this determination vary with the region of interest type, such as one or more sources of high priority for the biological rhythm disorder, one or more sources of lower priority for the rhythm disorder, a region of high frequency activity or rate, a region of scar, a region of complex activity, a region where electrical information shows dispersion. The system then calculates a direction or vector in which the catheter may be moved to reach a critical region for ablation.

In some embodiments, the guidance model prioritizes which of multiple identified sites is used to guide guidance direction. The invention ranks multiple sites by combining algorithms based on clinical features or based on 'theoretical' features. Ranking based on clinical features will often assign highest priority to sites with features similar to the sites where therapy terminated the rhythm disorder in training populations of patients. The next priority is all identified sites in patients in whom therapy terminated the rhythm disorder in training populations. The next priority may be all identified sites in a specified patient population. This ranking order can be modified in different embodiments, and with user input. Ranking can be achieved using machine learning trained on recordings at the appropriate resolution and ground truth labels in patients with successful or unsuccessful therapy. Training data can be obtained at a prior time in other patients, who may be similar to different to the current patient, or from this patient in a prior successful or unsuccessful procedure. The guidance model can thus use past experience to predict a new potential target site.

In some embodiments, ranking of critical sites can be performed based on features of theoretical and predicted importance, such as rotational activation, focal activation, repetition of other activation patterns, sites of complex fractionated electrograms, activation surrounding a region of scar or fibrosis, or other patterns which will be familiar to one skilled in the art. Such features may be continuous or intermittent with a certain threshold minimum number of cycles or occurrences.

Some embodiments of the invention combine these methods to prioritize multiple sites for directionality guidance and to guide therapy. This is performed because features predicted from animal or computational experiments may not arise in patients in this exact theoretical form. For instance, localized\rotational activation patterns in atrial fibrillation are a predominant mechanism in experimental work, but may appear in modified form in patients due for example to to noisy clinical recordings or co-existing diseases. An algorithm requiring theoretical parameters to be fulfilled may miss such features in patients. Conversely, sites of clinical importance may not have a clear theoretical basis, such as the feature of complex fractionated signals in atrial fibrillation. By combining approaches, the invention is able to rank a primary critical site for directional guidance, a second critical site for directional guidance and so on. If one or more sites are equidistant, or of equal priority, the operator is given the option of choosing which one to move to. Learning algorithms based on prior data of multiple concurrent critical regions in similar patients can also be used to suggest a choice to the operator.

This process may be repeated in one or more embodiments (module 1590) depending on the success of the ablation procedure. This is elaborated in the Ablation Treatment (Ablation Procedure) steps below.

FIG. 16 indicates specific logic architectures that can be used in different embodiments for guidance direction. Machine learning on advanced directionality information can be performed using multichannel EGM information. Models for rhythm directionality prediction 1650 and driver proximity prediction 1670 can be trained from datasets previously labeled for procedural success such as acute termination by ablation, or long-term success (i.e. freedom from recurrence).

While the ultimate result of directional guidance is a vector, several approaches can be used to calculate this result. This includes machine learning, vectorial mathematics, correlation analysis, frequency analysis, phase transform, comparison to recordings in this patient at a different time, comparison to recordings from a different patient.

Step 1651 indicates important components of the model 1650 in some embodiments. In step 1655 datasets with features relevant to directionality calculation are used as inputs. These features may include wave-front directions, activation onset times, activations from reconstructed action potentials (e.g. output from ML model 810), gradients in activation rate, electrogram shapes with varying degrees of similarity to a template, propagation patterns, and other features that will be apparent to one skilled in the art. The next step of preprocessing 1657 may include activation detection, band-pass filtering or other characterization methods. Datasets 1655 can also feed directly into ML model 1660. These EGM or derived characteristics can be then used to train a machine learning model 1660 to predict wavefront directionality 1665. In one embodiment, output of the ML model 1660 can be 2D or 3D vector or vectors representing the electrical propagation at the recorded region. In one embodiment, output of the ML model 1660 can be the probability of each spline or set of electrodes of the recording catheter 610 to be close to a therapeutic target outside the catheter recording region.

Step 1671 indicates important components of the model 1670 in some embodiments. 1675 and 1677 include datasets with features relevant to detection of driver proximity and presence. Datasets 1675 are labeled with a critical region for an arrhythmia (also termed a driver or source) and ML model 1680 can be trained to detect if the critical region is present or in proximity or further away. This can be characterized with preprocessing techniques 1677 as activation detection, band-pass filtering or other characterization methods. In one embodiment, features may include wave-front directions, activation onset times, activations from reconstructed action potentials (e.g. output from ML model 810), gradients in activation rate, electrogram shapes that are more or less similar to a template, propagation patterns, and other features that will be apparent to one skilled in the art. 1675 can also feed directly to ML model 1680. These EGM characteristics can then be used to train a machine learning model 1680 able to determine if a specific set of signal patterns are in proximity to a driver or not, and to determine if the critical region is present in the recorded region 1685. In one embodiment, output of the ML model 1680 can be the probability of the recorded intracardiac region to be a therapeutic target, defined as an AF driver, a site of AF termination or other electrophysiological or clinical feature.

In one embodiment, output of the ML model 1680 can be the relative distance of the recording catheter 610 to a therapeutic target outside the catheter recording area, or the probability to find a therapeutic target outside the catheter recording area closer than a defined distance.

ML models 1660 and 1680 can be trained with previous clinical or computational data in which clinical characteristics, such as presence of AF driver or ablation termination site, direction to AF driver or ablation termination site, electrical propagation information or distance to AF driver or ablation termination site, is identified.

In one embodiment, the personalized ML models 1660 and 1680 take as input signals and derived features 900 to 965 in FIG. 9 (4 seconds sampled at 500 Hz, i.e. 2000 samples) as well as their activation times identified by the prior ML model 810. In one embodiment, the ML models architecture 1660 and 1680 can be a sequential deep learning model comprised of several 1D or 2D convolution layer (N=2, filters=16, kernel size=8, and ReLU activation function), followed by 1D max pooling layer (pool size=8, strides=8), followed by a recurrent layer (units=4), followed by several 1D or 2D convolution layer (N=2, filters=16, kernel size=8, and ReLU activation function), followed by a dense layer (united=16, ReLU activation function), followed by a Dense layer (units=1, sigmoid activation function). The model can be trained with a binary cross entropy loss function and an optimization algorithm such as the Adam algorithm. Some embodiments can also consider mixed architectures, including other inputs as images 1110 (MRI/CT), demographics 1120 (age, gender, heart size, etc.), electrode configuration 1130 (size, area, etc.), temporal aspects 1140 (time of day, etc.) and spatial personalization 1150 (atrium, ventricle, etc.). Moreover, different parameters values (e.g. filters, kernel size, activation functions), optimization functions, or loss functions can also be used to fine tune the ML models 1660 and 1680. In some embodiments the architecture can be used with different number or order of convolutional, recurrent, or other layers or adding different connections (e.g. residual connections).

In one embodiment, the ML models 1660 and 1680 can be rule-based algorithms based on the input signals and derived features 900 to 965 in FIG. 9 (4 seconds sampled at 500 Hz, i.e. 2000 samples) as well as their activation times identified by the prior ML model 810. These rule-based algorithms can be based on the analysis of activation time sequence by fitting to individual or multiple planar propagations; identification of centrifugal activations by vectorial divergence analysis, phase analysis or fitting to centrifugal activation patterns; identification of reentrant patterns by vectorial rotation analysis, phase analysis or fitting to rotational patterns; identification of repeated patterns by correlation and vectorial similarity analysis; and other rule-based techniques for directionality and proximity prediction.

During the navigation and mapping procedure, electrical recordings 1595 and activations from reconstructed action potentials (e.g. output from ML model 810) can be introduced in this trained machine learning models 1650 and 1670 in order to obtain a prediction of the local propagation vector 1625 and the driver proximity 1630. The prediction of the local propagation vector can be then used to guide the catheter navigation 1640, suggesting directions to move towards or probabilities of wave-front incoming directions. Driver proximity information 1645 can be used to suggest ablation 1570.

Referring back to FIG. 1, the guidance direction is used to guide movement of the catheter 155 of the heart treatment device 105 to the critical region of interest, e.g., a source or target region of the arrhythmia. In some embodiments, the physician guides movement of the catheter 155 inside the patient. In such embodiments, the guidance direction can be displayed on the input/output device 125. In other embodiments the heart treatment device 105 may be motorized and automated, such that the guidance direction informs actuation of the motor to move the catheter 155 of the heart treatment device 105. The location algorithm is able to identify the position of the catheter 155 relative to the region of interest in the heart, and guide the catheter 155 to the region of interest.

In some embodiments, the device can perform directional navigation from the body surface. For example, a body surface ECG may identify the location of critical regions for the heart rhythm disorder (FIG. 15-16). The system then calculates the guidance direction or vector in which the electrode array catheter must be moved to reach each critical region for ablation. Directional navigation greatly advances over conventional systems where the entire organ had to be mapped to identify a potentially small region of interest. One analogy is a satellite navigational system which computes directional guidance to enable a user to get from position A to B. The prior art required the user to identify the location of site A within the organ, and then site B within the organ, and infer or estimate a course between these positions. The current invention provides directionality information directly from A to B without requiring that the physician infer this themselves, which is subjective, and without requiring use of a separate mapping apparatus which may introduce inaccuracies and inefficiencies into the procedure. The analogy is a modern satellite global positioning system that can give directions left and right without requiring the user to examine and interpret a map of the city or country.

In some embodiments, directional guidance is tailored by patient data beyond recorded signals. These data may include clinical, pathophysiological, laboratory, genetic or cellular elements. As an example, critical regions for AF may lie near the pulmonary veins in patients with early stage disease, yet lie away from the pulmonary veins in patients with advanced disease, heart failure or obstructive sleep apnea. Several other profiles can be defined. Similarly, critical regions for ventricular tachycardia may reside in the left ventricle in patients with heart failure from coronary disease, yet in the right ventricle in patients with arrhythmogenic cardiomyopathy or advanced lung disease.

The directional guidance system 1580 guides the catheter 155 according to the determined guidance direction. Guiding the catheter 155 may be accomplished autonomously by the treatment system 100. In other embodiments, the treatment system 100 displays the guidance direction (e.g., via the input/output device 125) to the physician. The physician may manually guide the catheter and/or provide control inputs (via the input/output device 125) to control movement of the catheter according to the guidance direction.

Ablation Treatment Model

The ablation treatment model 1570-1590 determines parameter for ablation to be delivered by the treatment device 105. The ablation treatment model 1570 inputs at least the electrical signals measured by the electrode array of the catheter 155. The ablation treatment model 1570 determines the parameters to ablate a region of interest that the catheter 155 of the treatment device 105 is in contact with. The parameters of the ablation procedure include select electrodes of the electrode array of the catheter 155 to actuate to deliver the ablation energy, the frequency of the ablation energy per electrode, the waveform of the ablation energy per electrode, the duration of the ablation energy per electrode, the irrigant to be delivered to the treatment site, the rate of irrigant flow, etc. The ablation procedure is provided to other components of the treatment system 100 for performing the ablation procedure.

The treatment system 100 performs the ablation procedure 1570. Referring to FIGS. 1, 2, the generator 115 may deliver the electrical energy to the electrode array of the catheter 155. The interposer 140 may selectively switch the determined electrodes to be used for ablation to an ablation configuration, and may switch the remaining electrodes into a ground configuration. The energy source 135 provides the ablation energy according to the parameters determined at step 1570 to each electrode configured for ablation. The irrigation pump 120 pumps irrigant to the irrigation pores of the catheter 155, which vents the irrigant to the tissue during delivery of the ablation energy.

The treatment system 100 performs confirmation sensing at the region of interest in step 1570. Some or all electrodes of the electrode array perform the confirmation sensing. The interposer 140 may switch some or all of the electrodes into the sensing configuration. The electrical signals sensed at the region of interest are provided to the control system 110 to analyze. In some embodiments, the catheter 155 and the electrode array are moved to regions surrounding the ablated region of interest to measure confirmation sensing signals.

In one or more embodiments, a non-invasive sensing device is used to perform the confirmation sensing 1570.

In FIG. 15 the treatment assessment model 1590 verifies success of an ablation procedure at a particular region of interest. The treatment assessment model 1590 may be one of the models 190. The treatment assessment model collects signals measured by the heart treatment device 105 after the ablation procedure has been performed. The electrical signals may be analyzed to determine whether the source region is still contributing to or affecting the heart rhythm disorder. Several metrics are used to verify the success of an ablation procedure. One embodiment may use a reduction in signals amplitude to reflect destruction of tissue. Another embodiment may use elimination of the targeted spatial feature (see FIG. 14). Yet another embodiment may observe to see if the rhythm pattern has changed, such as AF converting to another rhythm such as atrial tachycardia or sinus rhythm (acute termination of AF). These and other metrics can be used and can be assessed immediately from the same catheter without the need to replace the catheter with another tool or another mapping system.

In one or more embodiments, the verification process includes movement of the catheter 155 to one or more adjacent positions to the ablated region to sense and analyze electrical signals. In response to determining that the treatment was not successful 1590, the treatment system 100 determines whether to continue treatment at the current critical region of interest (ROI) which includes a driver or source region. For example, the treatment system 100 (or more specifically the treatment assessment model 1580 of the control system 110) determines whether the current critical region is still contributing to the heart rhythm disorder.

In response to determining to continue at the current region of interest, the treatment system 1570 determines another ablation procedure at the current region of interest. The additional ablation procedure may have similar parameters to the prior ablation procedure or may have different parameters. For example, a second ablation procedure may have a different ablation pattern, a different duration for delivery of the ablation energy, one or more pauses between periods of delivery ablation energy, or a different waveform for the ablation energy, when compared to a first ablation procedure. The treatment system 100 may repeat steps 1560 to 1590 in a loop, e.g., until the current region of interest no longer contributes to the heart rhythm disorder. Other stop conditions may be implemented, e.g., a hard stop of 3 ablation procedures.

In response to determining to not continue at the current region of interest, the treatment system 1570 determines directional guidance 1580 for steering the catheter to another region of interest. The treatment system 100 may repeat steps to arrive at the next region of interest for ablation treatment.

FIG. 15 further includes a method for classifying a heart rhythm disorder of the patient. The method implements one or more models, such as a classification model (all of which may be one or more of the models 190), to determine a type of heart rhythm disorder that is present in a given patient. The classification model inputs raw electrical signals, i.e., the recordings, the reconstructed recordings, other data described herein this disclosure, or some combination thereof. The parameters of the reconstructions or features used in the method can further serve as parametric information to inform training of the classification model. The classification model outputs a heart rhythm disorder classification which identifies a particular type of heart rhythm disorder. The heart rhythm classification may inform which patterns to look out for in the electrical signals, as each heart rhythm disorder may have unique patterns.

Example Computing System

Figure 17:
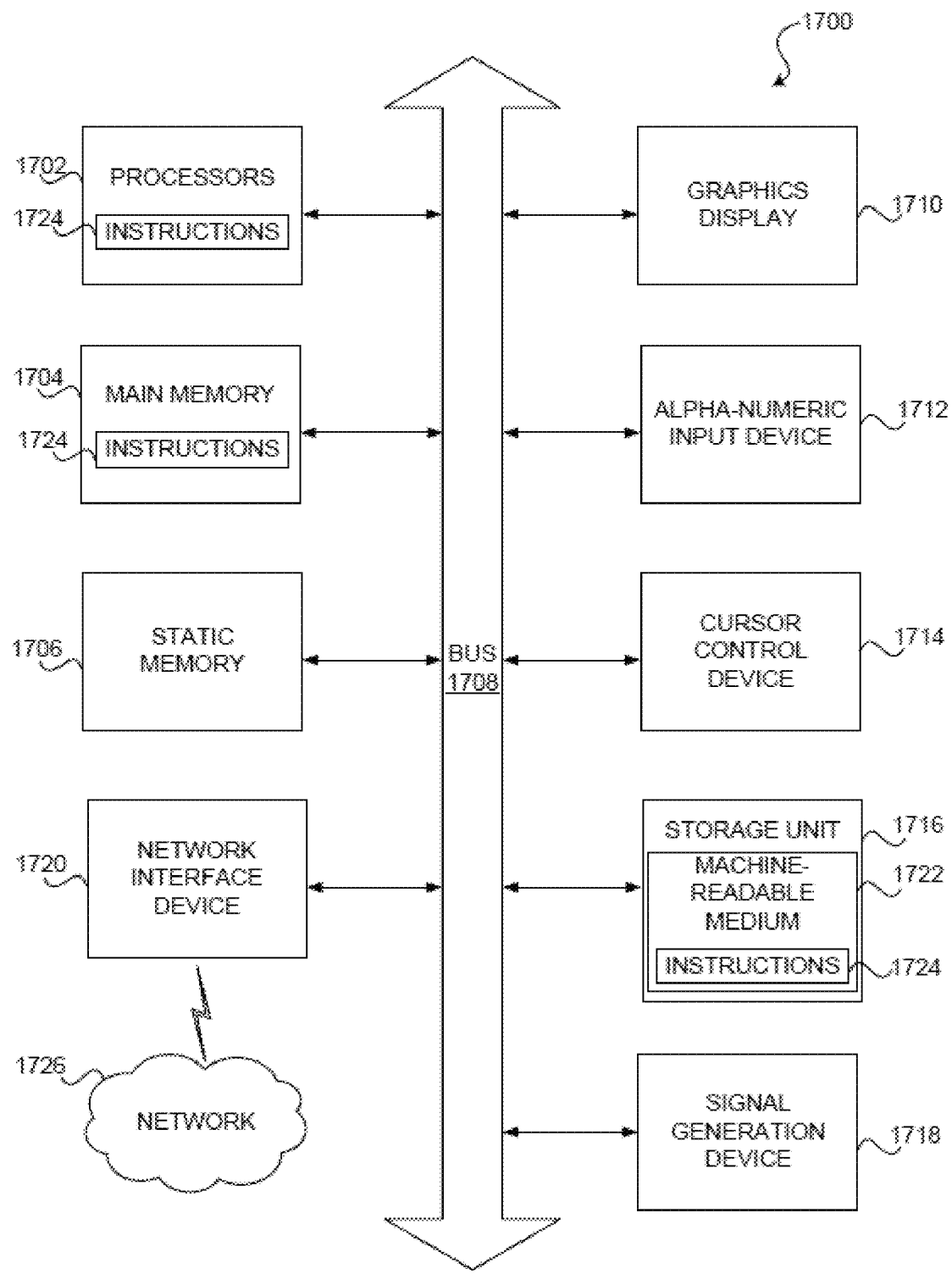
FIG. 17 illustrates a block diagram of a general computing system, according to one or more embodiments.

FIG. 17 illustrates a block diagram of a general computing system, according to one or more embodiments. A computer described herein may include a single computing machine shown in FIG. 17, a virtual machine, a distributed computing system that includes multiples nodes of computing machines shown in FIG. 17, or any other suitable arrangement of computing devices.

In some embodiments, a system may include a processor and a memory storing instructions that, when executed by the processor, perform operations including detecting bodily signals associated with one or more bodily functions at one or more sensors associated with the human body, processing the bodily signals to create one or more sensed signatures, processing the signatures using the digital object to determine an effector response, delivering one or more effector responses to control a bodily task and monitoring said response.

The data store 115 stores all the various data of the control system 110. The data store 115 may be one or more computing devices that include memories or other storage media for data related to the patients, e.g., in patient profiles such as data measured by the heart treatment device 105. Some of the data may take the form of personal digital records. The data may be routed by the control system 110. The data store 115 may be a network-based storage server (e.g., a cloud server). The data store 115 may be part of the computing server or may be a third-party storage system such as AMAZON AWS, AMAZON S3, DROPBOX, RACKSPACE CLOUD FILES, AZURE BLOB STORAGE, GOOGLE CLOUD STORAGE or ENGINE, etc.

By way of example, FIG. 17 shows a diagrammatic representation of a computing machine in the example form of a computer system 1700 within which instructions 1724 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 17 may correspond to any software, hardware, or combined components shown in FIG. 1, including but not limited to, the control system 110, and various engines, interfaces, terminals, and machines in this disclosure. While FIG. 17 shows various hardware and software elements, each of the components described in FIG. 1 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1724 that specify actions to be taken by that machine. Further, while only a single machine is illustrated, the term "machine" and "computer" may also be taken to include any collection of machines that individually or jointly execute instructions 1724 to perform any one or more of the methodologies discussed herein.

The example computer system 1700 includes one or more processors 1702 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1700 may also include a memory 1704 that store computer code including instructions 1724 that may cause the processors 1702 to perform certain actions when the instructions are executed, directly or indirectly by the processors 1702. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 1702 and reduces the space required for the memory 1704. For example, the signal processing techniques and machine learning methods described herein reduce the complexity of the computation of the processors 1702 by applying one or more techniques that simplify the steps in training, reaching convergence, and generating results of the processors 1702. The algorithms described herein also reduces the size of the models and datasets to reduce the storage space requirement for memory 1704.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1700 may include a main memory 1704, and a static memory 1706, which are configured to communicate with each other via a bus 1708. The computer system 1700 may further include a graphics display unit 1710 (e.g., a plasma display panel (personal digital record), a liquid crystal display (LCD), a projector, or a cathode ray tube (CRT)). The graphics display unit 1710, controlled by the processors 1702, displays a graphical user interface (GUI) to display one or more results and data generated by the processes described herein. The computer system 1700 may also include alphanumeric input device 1712 (e.g., a keyboard), a cursor control device 1714 (e.g., a mouse, a trackball, a joystick, a motion sensor, or other pointing instrument), a storage unit 1716 (a hard drive, a solid state drive, a hybrid drive, a memory disk, etc.), a signal generation device 1718 (e.g., a speaker), and a network interface device 1720, which also are configured to communicate via the bus 1708.

The storage unit 1716 includes a computer-readable medium 1722 on which is stored instructions 1724 embodying any one or more of the methodologies or functions described herein. The instructions 1724 may also reside, completely or at least partially, within the main memory 1704 or within the processor 1702 (e.g., within a processor's cache memory) during execution thereof by the computer system 1700, the main memory 1704 and the processor 1702 also constituting computer-readable media. The instructions 1724 may be transmitted or received over a network 1726 via the network interface device 1720.

While computer-readable medium 1722 is shown in an example embodiment to be a single medium, the term "computer-readable medium" should be taken to include a single medium or multiple media (e.g., a centralized or distributed database, or associated caches and servers) able to store instructions (e.g., instructions 1724). The computer-readable medium may include any medium that is capable of storing instructions (e.g., instructions 1724) for execution by the processors (e.g., processors 1702) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Embodiments

Additional embodiments include but are not limited to:

A non-transitory computer-readable storage medium storing instruction that, when executed by a processor, causes the processor to perform operations comprising: receiving a set of electrical signals of a human heart measured by a sensing array on a catheter coupled to a surface of the human heart, wherein each electrical signal of the set of electrical signals is measured by a sensing element of the sensing array; recreating an action potential signal from each electrical signal; inputting the reconstructed action potential signals into a guidance model to determine a guidance direction towards a critical region, wherein the guidance model is a machine-learned model that is trained using a plurality of training samples, each training sample comprising reconstructed action potential signals of one or more other human hearts measured by another sensing array and the respective directions towards the critical region; and providing the guidance direction to guide the catheter to provide therapy to treat the heart rhythm disorder.

The non-transitory computer-readable storage medium, wherein a reconstruction model recreates the action potential signal from each electrical signal, wherein the reconstruction model is a machine-learned model that is trained by: obtaining a plurality of training samples, each training sample comprising: a set of electrical signals measured by another sensing array of another catheter coupled to surface of another human heart, and a set of ground truth action potential signals, wherein each electrical signal corresponds to a ground truth action potential signal; training the reconstruction model based on the set of electrical signals and the set of ground truth action potential signals.

The non-transitory computer-readable storage medium, wherein recreating the action potential signal from each electrical signal comprises one or more of: filtering noise from the electrical signal with a low-pass filter; filtering noise from the electrical signal with a high-pass filter; filtering with a narrow-band-pass filter to identify a spectral band in the electrical signal; smoothing the electrical signal with a smoothing filter; performing spectral analysis to determine a spectral contribution to the electrical signal; and performing phase analysis to determine a phase of the electrical signal.

The non-transitory computer-readable storage medium, wherein the guidance model further determines whether the catheter is located at a critical region.

The non-transitory computer-readable storage medium, wherein the guidance model comprises a first sub-model and a second sub-model, wherein the first sub-model determines whether the catheter is located at the critical region, and wherein the second sub-model, responsive to determining that the catheter is not located at the critical region, determines the guidance direction.

The non-transitory computer-readable storage medium, wherein the guidance model further predicts a distance of the critical region from a current location of the catheter.

The non-transitory computer-readable storage medium, wherein the distance is one or more of: an absolute distance between the current location of the catheter and a location of the critical region; and a distance range between the current location of the catheter and the location of the critical region.

The non-transitory computer-readable storage medium, wherein the guidance model is trained by: obtaining the plurality of training samples, each training sample comprising a set of action potential signals, wherein each action potential signal is measured by a sensing element of another sensing array, and wherein a direction of a critical region is known at each sensing element of the sensing array; and training the guidance model based on the action potential signals and the directions of the critical region.

The non-transitory computer-readable storage medium, wherein a distance of the critical region is known for each action potential signal, and wherein the guidance model is further trained based on the distances of the critical region.

The non-transitory computer-readable storage medium, wherein the guidance model is further trained by: obtaining the plurality of training samples, each training sample comprising: a set of action potential electrical signals measured at another time, and a set of ground truth labels indicating that therapy at this or another known region was effective or not effective; and training the guidance model based on the action potential signals and the directions of the critical region.

The non-transitory computer-readable storage medium, wherein the guidance model determines the guidance direction by: partitioning the action potential signals into a plurality of subsets of action potential signal, each subset of the action potential signals corresponding to a window of sensing elements of the sensing array; inputting each subset of the action potential signals into the guidance model to determine a candidate guidance direction; and aggregating or selecting the candidate guidance directions over the plurality of subsets of action potential signals to generate the guidance direction.

The non-transitory computer-readable storage medium, wherein the window is a grid of sensing elements in a density of at least: 2-by-2 sensing elements in each area of 25 $mm^2$.

The non-transitory computer-readable storage medium, wherein the guidance model further determines a second guidance direction towards a second critical region.

The non-transitory computer-readable storage medium, wherein the guidance model further ranks the first critical region and the second critical region based on successful or unsuccessful therapy in the plurality of training samples.

The non-transitory computer-readable storage medium, wherein the guidance model is one of: a neural network, a Naïve Bayes classifier, a linear regression, a logistic regression, a K-nearest neighbor, a support vector machine, a decision tree, and a random forest.

The non-transitory computer-readable storage medium, wherein the critical region is one or more of: a focal activity, a rotational activity, a curvilinear activity, a complex signal shape activity, a low amplitude signal, a repeating pattern, and electrical activity surrounding a region of low amplitude signal.

The non-transitory computer-readable storage medium, wherein the operations further comprising: recreating from the set of electrical signals one or more of: activation onset times, activation offset times, spatial features, temporal features, and spectral features; wherein the one or more of activation onset times, activation offset times, spatial features, temporal features, and spectral features is input into the guidance model to determine the guidance direction towards the critical region.

A method comprising: receiving a set of electrical signals of a human heart measured by a sensing array on a catheter coupled to a surface of the human heart, wherein each electrical signal of the set of electrical signals is measured by a sensing element of the sensing array; recreating an action potential signal from each electrical signal; inputting the reconstructed action potential signals into a guidance model to determine a guidance direction towards a critical region, wherein the guidance model is a machine-learned model that is trained using a plurality of training samples, each training sample comprising reconstructed action potential signals of one or more other human hearts measured by another sensing array and the respective directions towards the critical region; and providing the guidance direction to guide the catheter to provide therapy to treat the heart rhythm disorder.

The method, wherein a reconstruction model recreates the action potential signal from each electrical signal, wherein the reconstruction model is a machine-learned model that is trained by: obtaining a plurality of training samples, each training sample comprising: a set of electrical signals measured by another sensing array of another catheter coupled to surface of another human heart, and a set of ground truth action potential signals, wherein each electrical signal corresponds to a ground truth action potential signal; training the reconstruction model based on the set of electrical signals and the set of ground truth action potential signals.

The method, wherein the guidance model further determines whether the catheter is located at a critical region.

The method, wherein the guidance model comprises a first sub-model and a second sub-model, wherein the first sub-model determines whether the catheter is located at the critical region, and wherein the second sub-model, responsive to determining that the catheter is not located at the critical region, determines the guidance direction.

The method, wherein the guidance model further predicts a distance of the critical region from a current location of the catheter.

The method, wherein the distance is one or more of: an absolute distance between the current location of the catheter and a location of the critical region; and a distance range between the current location of the catheter and the location of the critical region.

The method, wherein the guidance model is trained by: obtaining the plurality of training samples, each training sample comprising a set of action potential signals, wherein each action potential signal is measured by a sensing element of another sensing array, and wherein a direction of a critical region is known at each sensing element of the sensing array; and training the guidance model based on the action potential signals and the directions of the critical region.

The method, wherein a distance of the critical region is known for each action potential signal, and wherein the guidance model is further trained based on the distances of the critical region.

The method, wherein the guidance model is further trained by: obtaining the plurality of training samples, each training sample comprising: a set of action potential electrical signals measured at another time, and a set of ground truth labels indicating that therapy at this or another known region was effective or not effective; and training the guidance model based on the electrophysiological action potential signals and the directions of the critical region.

The method, wherein the guidance model determines the guidance direction by: partitioning the action potential signals into a plurality of subsets of action potential signal, each subset of the action potential signals corresponding to a window of sensing elements of the sensing array; inputting each subset of the action potential signals into the guidance model to determine a candidate guidance direction; and aggregating or selecting the candidate guidance directions over the plurality of subsets of action potential signals to generate the guidance direction.

The method, wherein the window is a grid of sensing elements in a density of at least: 2-by-2 sensing elements in each area of 25 $mm^2$.

The method, wherein the guidance model further determines a second guidance direction towards a second critical region.

The method, wherein the guidance model is one of: a neural network, a Naïve Bayes classifier, a linear regression, a logistic regression, a K-nearest neighbor, a support vector machine, a decision tree, and a random forest.

The method, wherein the critical region is one or more of: a focal activity, a rotational activity, a curvilinear activity, a complex signal shape activity, a low amplitude signal, a repeating pattern, and electrical activity surrounding a region of low amplitude signal.

The method, further comprising: recreating from the set of electrical signals one or more of: activation onset times, activation offset times, spatial features, temporal features, and spectral features; wherein the one or more of activation onset times, activation offset times, spatial features, temporal features, and spectral features is input into the guidance model to determine the guidance direction towards the critical region.

A method for training a reconstruction model to recreate an action potential signal from an electrical signal, the method comprising: obtaining a plurality of training samples, each training sample comprising: a set of electrical signals measured by a sensing array of a catheter coupled to a surface of a human heart, and a set of ground truth action potential signals, wherein each electrical signal corresponds to a ground truth action potential signal; training the reconstruction model based on the set of electrical signals and the set of ground truth action potential signals.

The method for training the reconstruction model, wherein the set of ground truth action potential signals are measured by another sensing array coupled to an exterior surface of a human body.

The method for training the reconstruction model, further comprising: filtering the set of electrical signals with one or more filters to remove artifacts.

The method for training the reconstruction model, wherein the filters comprise one or more of: a high-pass filter to exclude signals above a first threshold frequency; a low-pass filter to exclude signals below a second threshold frequency that is lower than the first threshold frequency; a smoothing filter to average the electrical signal; a normalization filter to normalize the set of electrical signals; and a ventricular activity cancellation filter to exclude signals attributable to ventricular activity.

The method for training the reconstruction model, further comprising: for each electrical signal, determining one or more features based on spectral analysis, wherein training of the reconstruction model is further based on the one or more features.

The method for training the reconstruction model, wherein the spectral analysis comprises one or more of: fast Fourier transform; Welch periodogram; discrete cosine transform; Hilbert transformations; principal component analysis; convolutional-based transform; and continuous wavelet transform.

The method for training the reconstruction model, further comprising: determining one or more derivative signals from the set of electrical signals, wherein training of the reconstruction model is further based on the derivative signals.

The method for training the reconstruction model, wherein the reconstruction model is a machine-learned model which is one of: a neural network, a Naïve Bayes classifier, a linear regression, a logistic regression, a K-nearest neighbor, a support vector machine, a decision tree, and a random forest.

A non-transitory computer-readable storage medium storing instructions for training a reconstruction model to recreate an action potential signal from an electrical signal, the instructions that, when executed by a processor, cause the processor to perform operations comprising: obtaining a plurality of training samples, each training sample comprising: a set of electrical signals measured by a sensing array of a catheter coupled to a surface of a human heart, and a set of ground truth action potential signals, wherein each electrical signal corresponds to a ground truth action potential signal; training the reconstruction model based on the set of electrical signals and the set of ground truth action potential signals.

A non-transitory computer-readable storage medium storing instructions for executing a reconstruction model to recreate an action potential signal from an electrical signal, the reconstruction model trained by: obtaining a plurality of training samples, each training sample comprising: a set of electrical signals measured by a sensing array of a catheter coupled to a surface of a human heart, and a set of ground truth action potential signals, wherein each electrical signal corresponds to a ground truth action potential signal; training the reconstruction model based on the set of electrical signals and the set of ground truth action potential signals.

A method for training a guidance model to determine a guidance direction of a catheter towards a critical region for a biological rhythm disorder, the method comprising: obtaining a plurality of training samples, each training sample comprising a set of action potential signals, wherein each action potential signal is measured by a sensing element of a sensing array, and wherein a direction of a critical region is known at each sensing element of the sensing array; and training the guidance model based on the action potential signals and the directions of the critical region.

The method for training the guidance model, wherein for an additional set of training samples, each comprising a set of electrical signals, the sensing array is located at the critical region, and wherein training the guidance model further comprises training the guidance model to determine whether the catheter is located at a critical region.

The method for training the guidance model, wherein the guidance model comprises a first sub-model and a second sub-model, wherein the first sub-model determines whether the catheter is located at the critical region, and wherein the second sub-model, responsive to determining that the catheter is not located at the critical region, determines the guidance direction.

The method for training the guidance model, wherein training the guidance model comprises: in a first training stage, training the first sub-model using the additional set of training samples; and in a second training stage, training the second sub-model using the plurality of training samples.

The method for training the guidance model, wherein training the guidance model further comprises training the guidance model to predict a distance of the critical region from a current location of the catheter.

The method for training the guidance model, wherein the distance is one or more of: an absolute distance between the current location of the catheter and a location of the critical region; and a distance range between the current location of the catheter and the location of the critical region.

The method for training the guidance model, wherein a distance of the critical region is known for each sensing element, and wherein the guidance model is further trained based on the distances of the critical region.

The method for training the guidance model, wherein each training sample includes a ground truth label indicating that therapy at this or another known region was effective or not effective; and wherein training the guidance model comprises training based on the ground truth labels.

The method for training the guidance model, wherein training the guidance model further comprises training the guidance model to determine a second guidance direction towards a second critical region.

The method for training the guidance model, wherein the guidance model is machine-learned model and one of: a neural network, a Naïve Bayes classifier, a linear regression, a logistic regression, a K-nearest neighbor, a support vector machine, a decision tree, and a random forest.

The method for training the guidance model, wherein training of the guidance model comprises training the guidance model to predict a type of critical region.

The method for training the guidance model, wherein a type of critical region for each training sample is one or more of: focal biological activity, rotational biological activity, curvilinear biological activity, complex activation pattern of biological activity, low amplitude signals, repeating patterns, and electrical activity surrounding a region of low amplitude signals, and wherein training of the guidance model is based on the types of critical region for the plurality of training samples.

The method for training the guidance model, wherein the set of action potential signals of each training sample are reconstructed from electrical signals measured by the sensing element of the sensing array.

A non-transitory computer-readable storage medium storing instructions for training a guidance model to determine a guidance direction of a catheter towards a critical region for a biological rhythm disorder, the instructions that, when executed by a processor, cause the processor to perform operations comprising: obtaining a plurality of training samples, each training sample comprising a set of action potential signals, wherein each action potential signal is measured by a sensing element of a sensing array, and wherein a direction of a critical region is known at each sensing element of the sensing array; and training the guidance model based on the action potential signals and the directions of the critical region.

A non-transitory computer-readable storage medium storing instructions for executing a guidance model to determine a guidance direction of a catheter towards a critical region for a biological rhythm disorder, the guidance model trained by: obtaining a plurality of training samples, each training sample comprising a set of action potential signals, wherein each action potential signal is measured by a sensing element of a sensing array, and wherein a direction of a critical region is known at each sensing element of the sensing array; and training the guidance model based on the action potential signals and the directions of the critical region.

A treatment system for providing therapy to treat a heart rhythm disorder, the treatment system comprising: a control system; and a heart treatment device comprising a catheter and a sensing array; wherein: the sensing array is arranged on the catheter and configured to be coupled to a human heart; the sensing array is configured to generate data in dependence on the measurement of a set of electrical signals of the human heart, wherein each electrical signal of the set of electrical signals is measured by a sensing element of the sensing array; the heart treatment device is configured to transmit the generated data to the control system; the control system is configured to recreate, in dependence on the data received from the heart treatment device, an action potential signal for each of the electrical signals; the control system is configured to input the action potential signals into a guidance model to determine a guidance direction of a catheter of the heart treatment device towards a critical region, wherein the guidance model is a machine-learned model that is trained using a plurality of training samples, each training sample comprising reconstructed action potential signals of one or more other human hearts measured by another sensing array and the respective directions towards the critical region; the control system is configured to generate instructions for the heart treatment device, wherein the instructions provide a guidance direction to the catheter such that the catheter is guided towards a critical region for receiving therapy; and the heart treatment device is configured to receive the generated instructions, from the control system, such that the catheter is guided towards the critical region for receiving therapy.

The treatment system, wherein a reconstruction model is configured to recreate an action potential signal from each electrical signal, wherein the reconstruction model is a machine-learned model that is trained by: obtaining a plurality of training samples, each training sample comprising: a set of electrical signals measured by another sensing array of another catheter coupled to surface of another human heart, and a set of ground truth action potential signals, wherein each electrical signal corresponds to a ground truth action potential signal; training the reconstruction model based on the set of electrical signals and the set of ground truth action potential signals.

The treatment system, wherein the guidance model is configured to further determine whether the catheter is located at a critical region.

The treatment system, wherein the guidance model comprises a first sub-model and a second sub-model, wherein the first sub-model is configured to determine whether the catheter is located at the critical region, and wherein the second sub-model, responsive to determining that the catheter is not located at the critical region, is configured to determine the guidance direction.

The treatment system, wherein the guidance model is configured to further predict a distance of the critical region from a current location of the catheter.

The treatment system, wherein the distance is one or more of: an absolute distance between the current location of the catheter and a location of the critical region; and a distance range between the current location of the catheter and the location of the critical region.

The treatment system, wherein the guidance model is trained by: obtaining the plurality of training samples, each training sample comprising a set of reconstructed action potential signals, wherein each reconstructed action potential signal is processed from electrical signals measured by a sensing element of another sensing array, and wherein a direction of a critical region is known at each sensing element of the sensing array; and training the guidance model based on the reconstructed action potential signals and the directions of the critical region.

The treatment system, wherein a distance of the critical region is known for each reconstructed action potential signal, and wherein the guidance model is further trained based on the distances of the critical region.

The treatment system, wherein the guidance model is further trained by: obtaining the plurality of training samples, each training sample comprising: a set of electrical signals measured at another time, and a set of ground truth labels indicating that therapy at this or other known region was effective or not effective; and training the guidance model based on the reconstructed action potential signals and the directions of the critical region.

The treatment system, wherein the guidance model is configured to determine the guidance direction by: partitioning the reconstructed action potential signals into a plurality of subsets of action potential signal, each subset of the reconstructed action potential signals corresponding to a window of sensing elements of the sensing array; inputting each subset of the reconstructed action potential signals into the guidance model to determine a candidate guidance direction; and aggregating or selecting the candidate guidance directions over the plurality of subsets of reconstructed action potential signals to generate the guidance direction.

The treatment system, wherein the window is a grid of sensing elements in a density of at least: 2-by-2 sensing elements in each area of 25 mm$^2$.

The treatment system, wherein the guidance model is configured to further determine a second guidance direction towards a second critical region.

The treatment system, wherein the guidance model is one of: a neural network, a Naïve Bayes classifier, a linear regression, a logistic regression, a K-nearest neighbor, a support vector machine, a decision tree, and a random forest.

The treatment system, wherein the critical region is one or more of: focal biological activity, rotational biological activity, curvilinear patterns of biological activity, complex patterns of biological activity, low amplitude signals, repeating patterns, and electrical activity surrounding a region of low amplitude signals.

The treatment system, wherein the control system is further configured to: recreate from the set of electrical signals one or more of: activation onset times, activation offset times, spatial features, temporal features, and spectral features; wherein the one or more of activation onset times, activation offset times, spatial features, temporal features, and spectral features is input into the guidance model to determine the guidance direction towards the critical region.

A heart treatment device for providing therapy to treat a heart rhythm disorder, wherein: the heart treatment device comprises a catheter and a sensing array; the sensing array is arranged on the catheter and configured to be coupled to a human heart; the sensing array is configured to generate data in dependence on the measurement of a set of electrical signals of the human heart, wherein each electrical signal of the set of electrical signals is measured by a sensing element of the sensing array; the heart treatment device is configured to transmit the generated data to a control system; and the heart treatment device is configured to receive instructions, from the control system, that provide a guidance direction to the catheter such that the catheter is guided towards a critical region for receiving therapy.

The heart treatment device, wherein the heart treatment device is automatically controlled by the control system.

A control system for treating a heart rhythm disorder by a heart treatment device, wherein: the control system is configured to receive data from a heart treatment device, wherein the received data comprises measurement data of a set of electrical signals of the human heart, and the heart treatment device comprises a sensing array configured to generate the measurement data; the control system is configured to recreate an action potential signal for each of the electrical signals; the control system is configured to input the reconstructed action potential signals into a guidance model to determine a guidance direction of a catheter of the heart treatment device towards a critical region, wherein the guidance model is a machine-learned model that is trained using a plurality of training samples, each training sample comprising reconstructed action potential signals of one or more other human hearts measured by another sensing array and the respective directions towards the critical region; the control system is configured to generate instructions for the heart treatment device, wherein the instructions provide a guidance direction to the catheter such that the catheter is guided towards the critical region for receiving therapy; and the control system is configured to transmit the generate instructions to the heart treatment device.

ADDITIONAL CONSIDERATIONS

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, or others. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. A treatment system for providing therapy to treat a heart rhythm disorder, the treatment system comprising:
    a control system; and a heart treatment device comprising a catheter and a sensing array;

wherein:
the sensing array is arranged on the catheter and configured to be coupled to a human heart;
the sensing array is configured to generate data in dependence on measurement of a set of electrical signals of the human heart, wherein each electrical signal of the set of electrical signals is measured by a sensing element of the sensing array;
the heart treatment device is configured to transmit the generated data to the control system;
the control system is configured to recreate, in dependence on the data received from the heart treatment device, an action potential signal for each of the electrical signals;
the control system is configured to input the action potential signals into a guidance model to determine a guidance direction of a catheter of the heart treatment device towards a critical region, wherein the guidance model is a machine-learned model that is trained using a plurality of training samples, each training sample comprising reconstructed action potential signals of one or more other human hearts measured by another sensing array and the respective directions towards the critical region;
the control system is configured to generate instructions for the heart treatment device, wherein the instructions provide a guidance direction to the catheter such that the catheter is guided towards a critical region for receiving therapy; and
the heart treatment device is configured to receive the generated instructions, from the control system, such that the catheter is guided towards the critical region for receiving therapy.

2. The treatment system of claim 1, wherein a reconstruction model is configured to recreate an action potential signal from each electrical signal, wherein the reconstruction model is a machine-learned model that is trained by:
obtaining a plurality of training samples, each training sample comprising:
a set of electrical signals measured by another sensing array of another catheter coupled to surface of another human heart, and
a set of ground truth action potential signals, wherein each electrical signal corresponds to a ground truth action potential signal;
training the reconstruction model based on the set of electrical signals and the set of ground truth action potential signals.

3. The treatment system of claim 1, wherein the guidance model is configured to further determine whether the catheter is located at a critical region.

4. The treatment system of claim 2, wherein the guidance model comprises a first sub-model and a second sub-model, wherein the first sub-model is configured to determine whether the catheter is located at the critical region, and wherein the second sub-model, responsive to determining that the catheter is not located at the critical region, is configured to determine the guidance direction.

5. The treatment system of claim 1, wherein the guidance model is configured to further predict a distance of the critical region from a current location of the catheter.

6. The treatment system of claim 5, wherein the distance is one or more of:
an absolute distance between the current location of the catheter and a location of the critical region; and
a distance range between the current location of the catheter and the location of the critical region.

7. The treatment system of claim 1, wherein the guidance model is trained by:
obtaining the plurality of training samples, each training sample comprising a set of action potential signals,
wherein each action potential signal is measured by a sensing element of another sensing array, and
wherein a direction of a critical region is known at each sensing element of the sensing array; and
training the guidance model based on the action potential signals and the directions of the critical region.

8. The treatment system of claim 7, wherein a distance of the critical region is known for each action potential signal, and wherein the guidance model is further trained based on the distances of the critical region.

9. The treatment system of claim 8, wherein the guidance model is further trained by:
obtaining the plurality of training samples, each training sample comprising:
a set of electrical signals measured at another time, and
a set of ground truth labels indicating that therapy at this or other known region was effective or not effective; and
training the guidance model based on the action potential signals and the directions of the critical region.

10. The treatment system of claim 1, wherein the guidance model is configured to determine the guidance direction by:
partitioning the action potential signals into a plurality of subsets of action potential signal, each subset of the action potential signals corresponding to a window of sensing elements of the sensing array;
inputting each subset of the action potential signals into the guidance model to determine a candidate guidance direction; and
aggregating or selecting the candidate guidance directions over the plurality of subsets of action potential signals to generate the guidance direction.

11. The treatment system of claim 10, wherein the window is a grid of sensing elements in a density of at least: 2-by-2 sensing elements in each area of 25 mm$^2$.

12. The treatment system of claim 1, wherein the guidance model is configured to further determine a second guidance direction towards a second critical region.

13. The treatment system of claim 1, wherein the guidance model is one of: a neural network, a Naïve Bayes classifier, a linear regression, a logistic regression, a K-nearest neighbor, a support vector machine, a decision tree, and a random forest.

14. The treatment system of claim 1, wherein the critical region is one or more of: a focal activity, a rotational activity, a curvilinear activity, a complex signal shape activity, a low amplitude signal, a repeating pattern, and electrical activity surrounding a region of low amplitude signal.

15. The treatment system of claim 1, wherein the control system is further configured to:
recreate from the set of electrical signals one or more of: activation onset times, activation offset times, spatial features, temporal features, and spectral features;
wherein the one or more of activation onset times, activation offset times, spatial features, temporal features, and spectral features is input into the guidance model to determine the guidance direction towards the critical region.

16. A heart treatment device for providing therapy to treat a heart rhythm disorder, wherein:

the heart treatment device comprises a catheter and a sensing array;

the sensing array is arranged on the catheter and configured to be coupled to a human heart;

the sensing array is configured to generate data in dependence on measurement of a set of electrical signals of the human heart, wherein each electrical signal of the set of electrical signals is measured by a sensing element of the sensing array;

the heart treatment device is configured to transmit the generated data to a control system; and the heart treatment device is configured to receive instructions, from the control system, that provide a guidance direction to the catheter such that the catheter is guided towards a critical region for receiving therapy.

17. The heart treatment device of claim 16, wherein the heart treatment device is automatically controlled by the control system.

18. The heart treatment device of claim 16, wherein the heart treatment device is further configured to navigate the catheter according to the instructions received from the control system.

19. The heart treatment device of claim 16, wherein the instructions further performing an ablation procedure by the heart treatment device.

20. The heart treatment device of claim 19, wherein the heart treatment device is further configured to perform the ablation procedure at the critical region using one or more ablating elements arranged on the catheter.

21. A control system for treating a heart rhythm disorder by a heart treatment device, wherein:

the control system is configured to receive data from a heart treatment device, wherein the received data comprises measurement data of a set of electrical signals of a human heart, and the heart treatment device comprises a sensing array configured to generate the measurement data;

the control system is configured to recreate an action potential signal for each of the electrical signals;

the control system is configured to input the action potential signals into a guidance model to determine a guidance direction of a catheter of the heart treatment device towards a critical region, wherein the guidance model is a machine-learned model that is trained using a plurality of training samples, each training sample comprising reconstructed action potential signals of one or more other human hearts measured by another sensing array and the respective directions towards the critical region;

the control system is configured to generate instructions for the heart treatment device, wherein the instructions provide a guidance direction to the catheter such that the catheter is guided towards the critical region for receiving therapy; and the control system is configured to transmit the generated instructions to the heart treatment device.

* * * * *